US012773462B2

(12) United States Patent
Deverman et al.

(10) Patent No.: US 12,773,462 B2
(45) Date of Patent: Oct. 27, 2026

(54) SYSTEMS FOR EVOLVED ADENO-ASSOCIATED VIRUSES (AAVs) FOR TARGETED DELIVERY

(71) Applicant: The Broad Institute, Inc., Cambridge, MA (US)

(72) Inventors: Benjamin E. Deverman, Cambridge, MA (US); Qin Huang, Cambridge, MA (US); Ken Y. Chan, Cambridge, MA (US)

(73) Assignee: The Broad Institute, Inc., Cambridge, MA (US)

( * ) Notice: Subject to any disclaimer, the term of this patent is extended or adjusted under 35 U.S.C. 154(b) by 1398 days.

(21) Appl. No.: 17/427,213

(22) PCT Filed: Jan. 30, 2020

(86) PCT No.: PCT/US2020/015972

§ 371 (c)(1),
(2) Date: Jul. 30, 2021

(87) PCT Pub. No.: WO2020/160337

PCT Pub. Date: Aug. 6, 2020

(65) Prior Publication Data

US 2022/0143214 A1 May 12, 2022

Related U.S. Application Data

(60) Provisional application No. 62/798,961, filed on Jan. 30, 2019.

(51) Int. Cl.
*C12N 15/86* (2006.01)
*A61K 48/00* (2006.01)
(Continued)

(52) U.S. Cl.
CPC ............ *A61K 48/005* (2013.01); *C12N 15/86* (2013.01); *C12N 2750/14122* (2013.01);
(Continued)

(58) Field of Classification Search
CPC .......... C12N 15/86; C12N 2750/14122; C12N 2750/14143; G01N 33/566; C07K 14/005
See application file for complete search history.

(56) References Cited

U.S. PATENT DOCUMENTS 5,552,157 A 9/1996 Yagi et al.
5,565,213 A 10/1996 Nakamori et al.
(Continued)

FOREIGN PATENT DOCUMENTS

WO WO 2008/103962 A2 8/2008
WO WO 2015/038958 A1 3/2015
(Continued)

OTHER PUBLICATIONS

Huang Q, Chan KY, Tobey IG, Chan YA, Poterba T, Boutros CL, Balazs AB, Daneman R, Bloom JM, Seed C, Deverman BE. Delivering genes across the blood-brain barrier: LY6A, a novel cellular receptor for AAV-PHP.B capsids. PLoS One. Nov. 14, 2019; 14(11):e0225206. PMID: 31725765; (Year: 2019).*
(Continued)

*Primary Examiner* — Gregory S Emch
*Assistant Examiner* — Michael Cameron Sveiven
(74) *Attorney, Agent, or Firm* — Wolf, Greenfield & Sacks, P.C.

(57) ABSTRACT

Methods for screening for an adeno-associated virus (AAV) capsid protein that can bind to a target protein (e.g., Ly6 protein) and related compositions are provided in aspects of the disclosure.

11 Claims, 32 Drawing Sheets

Specification includes a Sequence Listing.

(51) Int. Cl.
*C07K 14/005* (2006.01)
*G01N 33/566* (2006.01)

(52) U.S. Cl.
CPC .............. *C12N 2750/14143* (2013.01); *C12N 2750/14145* (2013.01); *C12N 2810/6027* (2013.01)

(56) References Cited

U.S. PATENT DOCUMENTS

| | | | |
|---|---|---|---|
| 5,567,434 | A | 10/1996 | Szoka, Jr. |
| 5,738,868 | A | 4/1998 | Shinkarenko |
| 5,741,516 | A | 4/1998 | Webb et al. |
| 5,795,587 | A | 8/1998 | Gao et al. |
| 7,198,951 | B2 | 4/2007 | Gao et al. |
| 9,585,971 | B2 | 3/2017 | Deverman et al. |
| 2017/0166926 | A1 | 6/2017 | Deverman et al. |
| 2021/0403946 | A1 | 12/2021 | Deverman et al. |

FOREIGN PATENT DOCUMENTS

| | | | | |
|---|---|---|---|---|
| WO | WO-2017100671 | A1 * | 6/2017 | ................ A61P 9/00 |
| WO | WO2018017754 | A1 * | 1/2018 | ............. A61K 38/46 |
| WO | WO 2019/211401 | A1 | 11/2019 | |
| WO | WO 2020/014471 | A1 | 1/2020 | |
| WO | WO 2020/028751 | A3 | 2/2020 | |
| WO | WO 2020/068990 | A1 | 4/2020 | |
| WO | WO 2020/160337 | A1 | 8/2020 | |

OTHER PUBLICATIONS

Invitrogen TRIzol Reagent Product Page (https://www.thermofisher.com/order/catalog/product/15596026) (Year: 2025).*

B Sivasankar, RM Donev, MP Longhi, TR Hughes, R Davies, DS Cole, BP Morgan, KJ Marchbank, CD59a deficient mice display reduced B cell activity and antibody production in response to T-dependent antigens, Molecular Immunology, vol. 44, Issue 11, 2007, pp. 2978-2987 (Year: 2007).*

Partial European Search Report for Application No. 20747933.8, mailed Oct. 10, 2022.

Extended European Search Report for Application No. 20747933.8, mailed Jan. 11, 2023.

Invitation to Pay Additional Fees for Application No. PCT/US2020/015972, mailed Mar. 18, 2020.

International Search Report and Written Opinion for Application No. PCT/US2020/015972, mailed May 21, 2020.

International Preliminary Report on Patentability for Application No. PCT/US2020/015972, mailed Aug. 12, 2021.

[No Author Listed], Genbank Submission; NCBI, Accession No. XP_001381054.1; Predicted: similar to olfactory receptor Olr218 [Monodelphis domestica]; Feb. 27, 2007.

Akache et al., The 37/67-kilodalton laminin receptor is a receptor for adeno-associated virus serotypes 8, 2, 3, and 9. J Virol. Oct. 2006;80(19):9831-6. doi: 10.1128/JVI.00878-06.

Albright et al., Discovery of a Neurotropic Footprint That Enables AAV Transport Across the Blood-Brain Barrier. Mol Ther. 2017; 25(5): 230-231.

Allen et al., Global Representations of Goal-Directed Behavior in Distinct Cell Types of Mouse Neocortex. Neuron. May 17, 2017;94(4):891-907.e6. doi: 10.1016/j.neuron.2017.04.017.

Aurnhammer et al., Universal real-time PCR for the detection and quantification of adeno-associated virus serotype 2-derived inverted terminal repeat sequences. Hum Gene Ther Methods. Feb. 2012;23(1):18-28. doi: 10.1089/hgtb.2011.034.

Aurnhammer et al., Universal real-time PCR for the detection and quantification of adeno-associated virus serotype 2-derived inverted terminal repeat sequences. Hum Gene Ther Methods. Feb. 2012;23(1):18-28. Supplementary Information. 2 pages.

Bedbrook et al., Machine learning-guided channelrhodopsin engineering enables minimally invasive optogenetics. Nat Methods. Nov. 2019;16(11):1176-1184. doi: 10.1038/s41592-019-0583-8. Epub Oct. 14, 2019.

Bedbrook et al., Viral Strategies for Targeting the Central and Peripheral Nervous Systems. Annu Rev Neurosci. Jul. 8, 2018;41:323-348. doi: 10.1146/annurev-neuro-080317-062048. Epub Apr. 25, 2018.

Bell et al., Identification of the galactose binding domain of the adeno-associated virus serotype 9 capsid. J Virol. Jul. 2012;86(13):7326-33. doi: 10.1128/JVI.00448-12. Epub Apr. 18, 2012.

Biswas et al., Toward machine-guided design of proteins. bioRxiv. Jun. 2, 2018; 1; 1-10. DOI: 10.1101/337154.

Bogan et al., Anatomy of hot spots in protein interfaces. J Mol Biol. Jul. 3, 1998;280(1):1-9. doi: 10.1006/jmbi.1998.1843.

Börner et al., Pre-arrayed Pan-AAV Peptide Display Libraries for Rapid Single-Round Screening. Mol Ther. Apr. 8, 2020;28(4):1016-1032. doi: 10.1016/j.ymthe.2020.02.009. Epub Feb. 13, 2020.

Brass et al., Identification of host proteins required for HIV infection through a functional genomic screen. Science. Feb. 15, 2008;319(5865):921-6. doi: 10.1126/science.1152725. Epub Jan. 10, 2008.

Bryant et al., Deep diversification of an AAV capsid protein by machine learning. Nat Biotechnol. Jun. 2021;39(6):691-696. doi: 10.1038/s41587-020-00793-4. Epub Feb. 11, 2021.

Chan et al., Engineered AAVs for efficient noninvasive gene delivery to the central and peripheral nervous systems. Nat Neurosci. Aug. 2017;20(8):1172-1179. doi: 10.1038/nn.4593. Epub Jun. 26, 2017.

Chao et al., Isolating and engineering human antibodies using yeast surface display. Nat Protoc. 2006;1(2):755-68. doi: 10.1038/nprot.2006.94.

Chinni et al., CXCL12/CXCR4 transactivates HER2 in lipid rafts of prostate cancer cells and promotes growth of metastatic deposits in bone. Mol Cancer Res. Mar. 2008;6(3):446-57. doi: 10.1158/1541-7786.MCR-07-0117.

Cray et al., Regulation and selective expression of Ly-6A/E, a lymphocyte activation molecule, in the central nervous system. Brain Res Mol Brain Res. Jun. 1990;8(1):9-15. doi: 10.1016/0169-328x(90)90003-v.

Dalkara et al., In vivo-directed evolution of a new adeno-associated virus for therapeutic outer retinal gene delivery from the vitreous. Sci Transl Med. Jun. 12, 2013;5(189):189ra76. doi: 10.1126/scitranslmed.3005708.

Danecek et al., Twelve years of SAMtools and BCFtools. Gigascience. Feb. 16, 2021;10(2):giab008. doi: 10.1093/gigascience/giab008.

Davis et al., Rational design and engineering of a modified adeno-associated virus (AAV1)-based vector system for enhanced retrograde gene delivery. Neurosurgery. Feb. 2015;76(2):216-25; discussion 225. doi: 10.1227/NEU.0000000000000589.

Dayton et al., More expansive gene transfer to the rat CNS: AAV PHP.EB vector dose-response and comparison to AAV PHP.B. Gene Ther. Aug. 2018;25(5):392-400. doi: 10.1038/s41434-018-0028-5. Epub Jul. 16, 2018.

Deutscher et al., Mechanism of galactosylation in the Golgi apparatus. A Chinese hamster ovary cell mutant deficient in translocation of UDP-galactose across Golgi vesicle membranes. J Biol Chem. Jan. 5, 1986;261(1):96-100.

Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.

Eichhoff, Nanobodies as tools for optimizing adeno-associated viruses for gene and tumor therapy. Dissertation, University of Hamburg. May 4, 2018. URL: https://ediss.sub.uni-hamburg.de/volltexte/2018/9158/.

Excoffon et al., Directed evolution of adeno-associated virus to an infectious respiratory virus. Proc Natl Acad Sci U S A. Mar. 10, 2009;106(10):3865-70. doi: 10.1073/pnas.0813365106. Epub Feb. 23, 2009.

Flytzanis et al., Broad gene expression throughout the mouse and marmoset brain after intravenous delivery of engineered AAV capsids. bioRxiv. 2020;1:1-21.

Fu et al., Crossing the blood-brain-barrier with viral vectors. Curr Opin Virol. Dec. 2016;21:87-92. doi: 10.1016/j.coviro.2016.08.006. Epub Sep. 1, 2016.

(56) References Cited

OTHER PUBLICATIONS

Fujimura et al., A lipid raft-associated 67kDa laminin receptor mediates suppressive effect of epigallocatechin-3-O-gallate on FcepsilonRI expression. Biochem Biophys Res Commun. Oct. 21, 2005;336(2):674-81. doi: 10.1016/j.bbrc.2005.08.146.
Gao et al., Clades of Adeno-associated viruses are widely disseminated in human tissues. J Virol. Jun. 2004;78(12):6381-8. doi: 10.1128/JVI.78.12.6381-6388.2004.
Gao et al., Therapeutic Delivery of Butyrylcholinesterase by Brain-Wide Viral Gene Transfer to Mice. Molecules. Jul. 8, 2017;22(7):1145. doi: 10.3390/molecules22071145.
Gibson et al., Adeno-Associated Viral Gene Therapy Using PHP. B:NPC1 Ameliorates Disease Phenotype in Mouse Model of Niemann-Pick C 1 Disease (conference paper). American Society of Gene and Cell Therapy Annual Meeting. Washington, DC, USA. (May 10-13, 2017).
Girod et al., Genetic capsid modifications allow efficient re-targeting of adeno-associated virus type 2. Nat Med. Sep. 1999;5(9):1052-6. doi: 10.1038/12491.
Guida et al., Mouse adenovirus type 1 causes a fatal hemorrhagic encephalomyelitis in adult C57BL/6 but not BALB/c mice. J Virol. Dec. 1995;69(12):7674-81. doi: 10.1128/JVI.69.12.7674-7681. 1995.
Hanlon et al., Selection of an Efficient AAV Vector for Robust CNS Transgene Expression. Mol Ther Methods Clin Dev. Oct. 23, 2019;15:320-332. doi: 10.1016/j.omtm.2019.10.007. eCollection Dec. 13, 2019.
Hillier et al., Causal evidence for retina-dependent and -independent visual motion computations in mouse cortex. Nat Neurosci. Jul. 2017;20(7):960-968. doi: 10.1038/nn.4566. Epub May 22, 2017.
Hochreiter et al., Long short-term memory. Neural Comput. Nov. 15, 1997;9(8):1735-80. doi: 10.1162/neco.1997.9.8.1735.
Hordeaux et al., The Neurotropic Properties of AAV-PHP.B Are Limited to C57BL/6J Mice. Mol Ther. Mar. 7, 2018;26(3):664-668. doi: 10.1016/j.ymthe.2018.01.018. Epub Feb. 2, 2018.
Huang et al., Delivering genes across the blood-brain barrier: LY6A, a novel cellular receptor for AAV-PHP.B capsids. PLoS One. Nov. 14, 2019;14(11):e0225206. doi: 10.1371/journal.pone.0225206. eCollection 2019.
Huang et al., Parvovirus glycan interactions. Curr Opin Virol. Aug. 2014;7:108-18. doi: 10.1016/j.coviro.2014.05.007. Epub Jul. 19, 2014.
Jackson et al., Better Targeting, Better Efficiency for Wide-Scale Neuronal Transduction with the Synapsin Promoter and AAV-PHP. B. Front Mol Neurosci. Nov. 4, 2016;9:116. doi: 10.3389/fnmol. 2016.00116. eCollection 2016.
Jarvinen et al., Systemically Administered, Target Organ-Specific Therapies for Regenerative Medicine. Int J Mol Sci. Sep. 30, 2015;16(10):23556-71. doi: 10.3390/ijms161023556.
Kariolis et al., Brain delivery of therapeutic proteins using an Fc fragment blood-brain barrier transport vehicle in mice and monkeys. Sci Transl Med. May 27, 2020;12(545):eaay1359. doi: 10.1126/scitranslmed.aay1359.
Keane et al., Mouse genomic variation and its effect on phenotypes and gene regulation. Nature. Sep. 14, 2011;477(7364):289-94. doi: 10.1038/nature10413.
Kikkert et al., Binding of Tomato Spotted Wilt Virus to a 94-kDa Thrips Protein. Phytopathology. Jan. 1998;88(1):63-9. doi: 10.1094/PHYTO.1998.88.1.63.
Körbelin et al., A brain microvasculature endothelial cell-specific viral vector with the potential to treat neurovascular and neurological diseases. EMBO Mol Med. Jun. 1, 2016;8(6):609-25. doi: 10.15252/emmm.201506078. Print Jun. 2016.
Kotterman et al., Engineered AAV vectors for improved central nervous system gene delivery. Neurogenesis. Dec. 3, 2015;2(1):e1122700. doi: 10.1080/23262133.2015.1122700. eCollection 2015.
Krishnan et al., RNA interference screen for human genes associated with West Nile virus infection. Nature. Sep. 11, 2008;455(7210):242-5. doi: 10.1038/nature07207.
Kumar et al., Multiplexed Cre-dependent selection yields systemic AAVs for targeting distinct brain cell types. Nat Methods. May 2020;17(5):541-550. doi: 10.1038/s41592-020-0799-7. Epub Apr. 20, 2020.
Langmead et al., Fast gapped-read alignment with Bowtie 2. Nat Methods. Mar. 4, 2012;9(4):357-9. doi: 10.1038/nmeth.1923.
Li et al., Single amino acid modification of adeno-associated virus capsid changes transduction and humoral immune profiles. J Virol. Aug. 2012;86(15):7752-9. doi: 10.1128/JVI.00675-12. Epub May 16, 2012.
Li et al., The Sequence Alignment/Map format and SAMtools. Bioinformatics. Aug. 15, 2009;25(16):2078-9. doi: 10.1093/bioinformatics/btp352. Epub Jun. 8, 2009.
Lisowski et al., Selection and evaluation of clinically relevant AAV variants in a xenograft liver model. Nature. Feb. 20, 2014;506(7488):382-6. doi: 10.1038/nature12875. Epub Dec. 25, 2013.
Liu et al., Identification of chicken lymphocyte antigen 6 complex, locus E (LY6E, alias SCA2) as a putative Marek's disease resistance gene via a virus-host protein interaction screen. Cytogenet Genome Res. 2003;102(1-4):304-8. doi: 10.1159/000075767.
Loeuillet et al., In vitro whole-genome analysis identifies a susceptibility locus for HIV-1. PLoS Biol. Feb. 2008;6(2):e32. doi: 10.1371/journal.pbio.0060032.
Loughner et al., Organization, evolution and functions of the human and mouse Ly6/uPAR family genes. Hum Genomics 10, 10, doi:10.1186/s40246-016-0074-2.
Malek et al., Role of Ly-6 in lymphocyte activation. II. Induction of T cell activation by monoclonal anti-Ly-6 antibodies. J Exp Med. Sep. 1, 1986;164(3):709-22. doi: 10.1084/jem.164.3.709.
Mar et al., LY6E mediates an evolutionarily conserved enhancement of virus infection by targeting a late entry step. Nat Commun. Sep. 6, 2018;9(1):3603. doi: 10.1038/s41467-018-06000-y.
Marques et al., Applying machine learning to predict viral assembly for adeno-associated virus capsid libraries. Mol Ther Methods Clin Dev. Dec. 3, 2020;20:276-286. doi: 10.1016/j.omtm.2020.11.017. eCollection Mar. 12, 2021.
Mason et al., Deep learning enables therapeutic antibody optimization in mammalian cells by deciphering high-dimensional protein sequence space. bioRxiv. 2019;1:1-25.
Matochko et al., Deep sequencing analysis of phage libraries using Illumina platform. Methods. Sep. 2012;58(1):47-55. doi: 10.1016/j.ymeth.2012.07.006. Epub Jul. 20, 2012.
Matsuzaki et al., Intravenous administration of the adeno-associated virus-PHP.B capsid fails to upregulate transduction efficiency in the marmoset brain. Neurosci Lett. Feb. 5, 2018;665:182-188. doi: 10.1016/j.neulet.2017.11.049. Epub Nov. 24, 2017.
Mattheakis et al., An in vitro polysome display system for identifying ligands from very large peptide libraries. Proc Natl Acad Sci U S A. Sep. 13, 1994;91(19):9022-6. doi: 10.1073/pnas.91.19.9022.
Mayor et al., Sorting GPI-anchored proteins. Nat Rev Mol Cell Biol. Feb. 2004;5(2):110-20. doi: 10.1038/nrm1309.
Mccafferty et al., Phage antibodies: filamentous phage displaying antibody variable domains. Nature. Dec. 6, 1990;348(6301):552-4. doi: 10.1038/348552a0.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Morabito et al., AAV-PHP.B-Mediated Global-Scale Expression in the Mouse Nervous System Enables GBA1 Gene Therapy for Wide Protection from Synucleinopathy. Mol Ther. Dec. 6, 2017;25(12):2727-2742. doi: 10.1016/j.ymthe.2017.08.004. Epub Aug. 10, 2017.
Müller et al., Random peptide libraries displayed on adeno-associated virus to select for targeted gene therapy vectors. Nat Biotechnol. Sep. 2003;21(9):1040-6. doi: 10.1038/nbt856. Epub Aug. 3, 2003.
Münch et al., Off-target-free gene delivery by affinity-purified receptor-targeted viral vectors. Nat Commun. Feb. 10, 2015;6:6246. doi: 10.1038/ncomms7246.
Nathwani et al., Advances in Gene Therapy for Hemophilia. Hum Gene Ther. Nov. 2017;28(11):1004-1012. doi: 10.1089/hum.2017. 167.

(56) References Cited

OTHER PUBLICATIONS

Nonnenmacher et al., Adeno-Associated Virus 2 Infection Requires Endocytosis through the CLIC/GEEC Pathway. Cell Host Microbe. Dec. 15, 2011; 10(6): 563-76.
Nonnenmacher et al., Rapid evolution of blood-brain-barrier-penetrating AAV capsids by RNA-driven biopanning. Mol Ther Methods Clin Dev. Dec. 23, 2020;20:366-378. doi: 10.1016/j.omtm.2020.12.006. eCollection Mar. 12, 2021.
Ogden et al., Comprehensive AAV capsid fitness landscape reveals a viral gene and enables machine-guided design. Science. Nov. 29, 2019;366(6469):1139-1143. doi: 10.1126/science.aaw2900.
Ojala et al., In Vivo Selection of a Computationally Designed Schema AAV Library Yields a Novel Variant for Infection of Adult Neural Stem Cells in the SVZ. Mol Ther. Jan. 3, 2018;26(1):304-319. doi: 10.1016/j.ymthe.2017.09.006. Epub Sep. 8, 2017.
Ortega et al., Role of Ly-6 in lymphocyte activation. I. Characterization of a monoclonal antibody to a nonpolymorphic Ly-6 specificity. J Immunol. Nov. 15, 1986;137(10):3240-6.
Paulk et al., Bioengineered Viral Platform for Intramuscular Passive Vaccine Delivery to Human Skeletal Muscle. Mol Ther Methods Clin Dev. Jul. 24, 2018;10:144-155. doi: 10.1016/j.omtm.2018.06.001. eCollection Sep. 21, 2018.
Pierleoni et al., PredGPI: a GPI-anchor predictor. BMC Bioinformatics. Sep. 23, 2008;9:392. doi: 10.1186/1471-2105-9-392.
Pillay et al., AAV serotypes have distinctive interactions with domains of the cellular receptor AAVR. J Virol. Aug. 24, 2017;91(18):e00391-17. doi: 10.1128/JVI.00391-17. Print Sep. 15, 2017.
Pillay et al., An essential receptor for adeno-associated virus infection. Nature. Feb. 4, 2016;530(7588):108-12. doi: 10.1038/nature16465. Epub Jan. 27, 2016.
Pulicherla et al., Engineering liver-detargeted AAV9 vectors for cardiac and musculoskeletal gene transfer. Mol Ther. Jun. 2011;19(6):1070-8. doi: 10.1038/mt.2011.22. Epub Mar. 1, 2011.
Qian et al., Directed Evolution of AAV Serotype 5 for Increased Hepatocyte Transduction and Retained Low Humoral Seroreactivity. Mol Ther Methods Clin Dev. Oct. 20, 2020;20:122-132. doi: 10.1016/j.omtm.2020.10.010. eCollection Mar. 12, 2021.
Ran et al., In vivo genome editing using *Staphylococcus aureus* Cas9. Nature. Apr. 9, 2015;520(7546):186-91. doi: 10.1038/nature14299. Epub Apr. 1, 2015.
Ravina et al., Intraputaminal AADC gene therapy for advanced Parkinson's disease: interim results of a phase 1b Trial [abstract]. Human Gene Therapy. Dec 1, 2017; 28(12): A6. Accessed at: https://doi.org/10.1089/hum.2017.29055.abstracts.
Ravn et al., By-passing in vitro screening—next generation sequencing technologies applied to antibody display and in silico candidate selection. Nucleic Acids Res. Nov. 2010;38(21):e193. doi: 10.1093/nar/gkq789. Epub Sep. 15, 2010.
Riesselman et al., Accelerating Protein Design Using Autoregressive Generative Models. BioRxiv. 2019; 1: 1-7.
Rolnick et al., Deep Learning is Robust to Massive Label Noise. ArXiv. 2018; 3: 1-10.
Sago et al., High-throughput in vivo screen of functional mRNA delivery identifies nanoparticles for endothelial cell gene editing. Proc Natl Acad Sci U S A. Oct. 16, 2018;115(42):E9944-E9952. doi: 10.1073/pnas.1811276115. Epub Oct. 1, 2018.
Sago et al., Nanoparticles That Deliver RNA to Bone Marrow Identified by in Vivo Directed Evolution. J Am Chem Soc. Dec. 12, 2018;140(49):17095-17105. doi: 10.1021/jacs.8b08976. Epub Nov. 16, 2018.
Sah, Safety and Increased Transduction Efficiency in the Adult Nonhuman Primate Central Nervous System with Intravenous Delivery of Two Novel Adeno-Associated Virus Capsids [abstract 0661]. American Society of Gene and Cell Therapy Annual Meeting. Chicago, IL, USA. Molecular Therapy. (May 16-19, 2018).
Saha et al., GPI-anchored protein organization and dynamics at the cell surface. J Lipid Res. Feb. 2016;57(2):159-75. doi: 10.1194/jlr.R062885. Epub Sep. 22, 2015.
Shen et al., Terminal N-Linked Galactose Is the Primary Receptor for Adeno-associated Virus 9. J Biol Chem. Apr. 15, 2011;286(15):13532-40. doi: 10.1074/jbc.M110.210922. Epub Feb. 17, 2011.
Simon et al., Epithelial cell adhesion molecule-targeted drug delivery for cancer therapy. Expert Opin Drug Deliv. Apr. 2013;10(4):451-68. doi: 10.1517/17425247.2013.759938. Epub Jan. 14, 2013.
Sinai et al., A primer on model-guided exploration of fitness landscapes for biological sequence design. ArXiv. Oct. 23, 2020; 2:1-43.
Smith, Filamentous fusion phage: novel expression vectors that display cloned antigens on the virion surface. Science. Jun. 14, 1985;228(4705):1315-7. doi: 10.1126/science.4001944.
Spindler et al., The major locus for mouse adenovirus susceptibility maps to genes of the hematopoietic cell surface-expressed LY6 family. J Immunol. Mar. 15, 2010;184(6):3055-62. doi: 10.4049/jimmunol.0903363. Epub Feb. 17, 2010.
Summerford et al., AAVR: A Multi-Serotype Receptor for AAV. Mol Ther. Apr. 2016;24(4):663-6. doi: 10.1038/mt.2016.49.
Tabuchi et al., Multi-line split DNA synthesis: a novel combinatorial method to make high quality peptide libraries. BMC Biotechnol. Sep. 1, 2004:4:19. doi: 10.1186/1472-6750-4-19.
Tervo et al., A Designer AAV Variant Permits Efficient Retrograde Access to Projection Neurons. Neuron. Oct. 19, 2016;92(2):372-382. doi: 10.1016/j.neuron.2016.09.021. Epub Oct. 6, 2016.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. doi: 10.1074/jbc.M116.741314. Epub Aug. 30, 2016.
Tse et al., Structure-guided evolution of antigenically distinct adeno-associated virus variants for immune evasion. Proc Natl Acad Sci U S A. Jun. 13, 2017;114(24):E4812-E4821. doi: 10.1073/pnas.1704766114. Epub May 30, 2017.
Van De Rijn et al., Mouse hematopoietic stem-cell antigen Sca-1 is a member of the Ly-6 antigen family. Proc Natl Acad Sci U S A. Jun. 1989;86(12):4634-8. doi: 10.1073/pnas.86.12.4634.
Weinmann et al., Identification of a myotropic AAV by massively parallel in vivo evaluation of barcoded capsid variants. Nat Commun. Oct. 28, 2020;11(1):5432. doi: 10.1038/s41467-020-19230-w.
Whitehead et al., Optimization of affinity, specificity and function of designed influenza inhibitors using deep sequencing. Nat Biotechnol. May 27, 2012;30(6):543-8. doi: 10.1038/nbt.2214.
Yalcin et al., Sequence-based characterization of structural variation in the mouse genome. Nature. Sep. 14, 2011;477(7364):326-9. doi: 10.1038/nature10432.
Yang et al., Machine-learning-guided directed evolution for protein engineering. Nat Methods. Aug. 2019;16(8):687-694. doi: 10.1038/s41592-019-0496-6. Epub Jul. 15, 2019.
Zelikowsky et al., The Neuropeptide Tac2 Controls a Distributed Brain State Induced by Chronic Social Isolation Stress. Cell. May 17, 2018;173(5):1265-1279.e19. doi: 10.1016/j.cell.2018.03.037.
Zhang et al., An RN A-sequencing transcriptome and splicing database of glia, neurons, and vascular cells of the cerebral cortex. J Neurosci. Sep. 3, 2014;34(36):11929-47. doi: 10.1523/JNEUROSCI.1860-14.2014.
Zhang et al., Protein structure and sequence re-analysis of 2019-nCoV genome does not indicate snakes as its intermediate host or the unique similarity between its spike protein insertions and HIV-1. bioRxiv. Feb. 8, 2020;2020.02.04.933135. doi: 10.1101/2020.02.04.933135. Preprint.
Zurzolo et al., Glycosylphosphatidylinositol-anchored proteins: Membrane organization and transport. Biochim Biophys Acta. Apr. 2016;1858(4):632-9. doi: 10.1016/j.bbamem.2015.12.018. Epub Dec. 17, 2015.

* cited by examiner

FIG. 5E
Selected on cells expressing Ly6c1 ($10^{11}$ vg/mouse)
AAV(Ly6c1-C1)
AAV(Ly6c1-C2)
AAV(Ly6c1-C5)
NLS-GFP
C57BL/6J
BALB/cJ

| Approved gene symbol (NCBI accession #) | Gene name | Alias(es) | Genomic location | Number of | |
|---|---|---|---|---|---|
| | | | | Exons | LU Domains |
| *ACRV1* (NP_001603.1) | Acrosomal vesicle protein 1 | *SP-10; SPACA2; D11S4365* | 11q24.2 | 5 | 1 |
| *CD177* (BAE93254.1) | CD177 molecule (Human Neutrophil Alloantigen 2A) | *NB1; PRV1; HNA2A; PRV-1; HNA-2a; NB1 GP* | 19q13.2 | 9 | 2 |
| *CD59* (CAG46523.1) | CD59 molecule, complement regulatory protein | *1 F5; EJ16; EJ30; EL32; G344; MIN1; MIN2; MIN3; MIRL; HRF20; MACIF; MEM43; MIC11; MSK21; 16.3A5; HRF-20; MAC-IP; p18-20* | 11p13 | 5 | 1 |
| *GML* (EAW82296.1) | Glycosylphosphatidylinositol anchored molecule like | *LY6DL* | 8q24.3 | 5 | 1 |
| *GPIHBP1* (AAH35810.2) | Glycosylphosphatidylinositol anchored high density lipoprotein-binding protein 1 | *HYPL1D; GPI-HBP1* | 8q24.3 | 4 | 1 |
| *LY6D* (AAH31330.1) | Lymphocyte antigen 6 complex, locus D | *E48; Ly-6D* | 8q24 | 3 | 1 |
| *LY6E* (AAH03392.1) | Lymphocyte antigen 6 complex, locus E | *RIGE; SCA2; RIG-E; SCA-2; TSA-1* | 8q24.3 | 4 | 1 |
| *LY6G5B* (CAC85543.1) | Lymphocyte antigen 6 complex, locus G5B | *G5b; C6orf19* | 6p21.3 | 3 | 1 |
| *LY6G5C* (CAC85542.1) | Lymphocyte antigen 6 complex, locus G5C | *G5C; NG33; C6orf20; LY6G5CA; LY6G5CB* | 6p21 | 3 | 1 |
| *LY6G6C* (EAX03491.1) | Lymphocyte antigen 6 complex, locus G6C | *G6c; NG24; C6orf24* | 6p21 | 3 | 1 |
| *LY6G6D* (CAC85540.1) | Lymphocyte antigen 6 complex, locus G6D | *G6D; NG25; LY6-D; MEGT1; C6orf23* | 6p21.3 | 3 | 1 |
| *LY6G6F* (AAI37213.1) | Lymphocyte antigen 6 complex, locus G6F | *G6f; NG32; LY6G6D; C6orf21* | 6p21.33 | 6 | 1 |
| *LY6H* (BAA34115.1) | Lymphocyte antigen 6 complex, locus H | *NMLY6* | 8q24.3 | 4 | 1 |
| *LY6K* (AAI17145.1) | Lymphocyte antigen 6 complex, locus K | *CT97; ly-6 K; URLC10; HSJ001348* | 8q24.3 | 3 | 1 |
| *LY6L*[a] (XP_011544859.1) | Lymphocyte antigen 6 complex, locus L | *LOC101928108* | 8q24.3 | 5 | 1 |
| *LYNX1* (NP_803429.1) | Ly6/neurotoxin 1 8q24.3 4 | | 8q24.3 | 4 | 1 |
| *LYPD1* (EAX11675.1) | Ly6/PLAUR domain containing 1 | *PHTS; LYPDC1; LYNX2* | 2q21.2 | 3 | 1 |
| *LYPD2* (EAW82307.1) | Ly6/PLAUR domain containing 2 | *LYPDC2; UNQ430* | 8q24.3 | 3 | 1 |
| *LYPD3* (EAW57190.1) | Ly6/PLAUR domain containing 3 | *C4.4A* | 19q13.31 | 5 | 2 |

FIG. 12A

| **Approved gene symbol (NCBI accession #)** | **Gene name** | **Alias(es)** | **Genomic location** | **Number of** | |
|---|---|---|---|---|---|
| | | | | Exons | LU Domains |
| *LYPD4* (AAH34629.1) | Ly6/PLAUR domain containing 4 | *Sperm Membrane Receptor* | 19q13.2 | 5 | 1 |
| *LYPD5* (EAW57232.1) | Ly6/PLAUR domain containing 5 | *PRO4356* | 19q13.31 | 5 | 1 |
| *LYPD6* (AAH47013.1) | Ly6/PLAUR domain containing 6 | | 2q23.2 | 5 | 1 |
| *LYPD6B* (AAH18203.1) | Ly6/PLAUR domain containing 6B | *CT116; LYPD7* | 2q23.2 | 7 | 1 |
| *LYPD8* (NP_001278212.1) | Ly6/PLAUR domain containing 8 | | 1q44 | 7 | 1 |
| *PATE1* (AAI07045.1) | Prostate and testis expressed 1 | *PATE* | 11q24.2 | 5 | 1 |
| *PATE2* (AAI44527.1) | Prostate and testis expressed 2 | *PATE-M; UNQ3112; C11orf38* | 11q24.2 | 6 | 1 |
| *PATE3* (NP_001123355.3) | Prostate and testis expressed 3 | *HEL-127; PATE-DJ* | 11q24.2 | 3 | 3 |
| *PATE4* (NP_001138346.1) | Prostate and testis expressed 4 | *PATE-B* | 11q24.2 | 3 | 1 |
| *PINLYP* (NP_001180550.1) | Phospholipase A2 inhibitor and Ly6/PLAUR domain containing | | 19q13.31 | 6 | 1 |
| *PLAUR* (CAG33233.1) | Plasminogen activator, urokinase receptor | *CD87; UPAR; URKR; U-PAR* | 19q13 | 7 | 3 |
| *PSCA* (AAH65183.1) | Prostate stem cell antigen | *PRO232* | 8q24.2 | 3 | 1 |
| *SLURP1* (AAT01436.1) | Secreted Ly6/PLAUR domain containing 1 | *ARS; MDM; ANUP; ArsB; LY6LS* | 8q24.3 | 3 | 1 |
| *SLURP2* (NP_803253.1) | Secreted Ly6/PLAUR domain containing 2 | *LYNX1, isoform B precursor* | 8q24.3 | 4 | 1 |
| *SPACA4* (AAQ88753.1) | Sperm acrosome associated 4 | *SAMP14* | 19q13.33 | 1 | 1 |
| *TEX101* (EAW57189.1) | Testis expressed 101 | *SGRG; CT131; GTPR867; NYD-SP8; PRO1884; SPATA44; TES101RP* | 19q13.31 | 9 | 1 |

[a] Novel gene named in Loughner et al. Human Genomic (2016) 10:10

FIG. 12B

SYSTEMS FOR EVOLVED ADENO-ASSOCIATED VIRUSES (AAVs) FOR TARGETED DELIVERY

CROSS REFERENCE TO RELATED APPLICATIONS

This application is a national stage filing under 35 U.S.C. § 371 of International PCT Application No. PCT/US2020/015972, filed Jan. 30, 2020, which was published under PCT Article 21 (2) in English, and which claims priority to and the benefit of U.S. Provisional Application No. 62/798,961, filed Jan. 30, 2019, the entire disclosure of each of which is hereby incorporated by reference.

FEDERALLY SPONSORED RESEARCH

This invention was made with government support under Grant No. NINDS UG3 NS111689-01 awarded by the National Institutes of Health Somatic Cell Genome Editing Consortium. The government has certain rights in the invention.

DESCRIPTION OF THE TEXT FILE SUBMITTED ELECTRONICALLY

The instant application contains a Sequence Listing which has been submitted in ASCII format via EFS-Web and is hereby incorporated by reference in its entirety. The ASCII file, created on Jul. 27, 2021, is named B119570068US01-SEQ-SXT.txt and is 5,473,462 bytes in size.

BACKGROUND OF THE INVENTION

AAV vectors provide a safe and versatile platform for gene therapy. For example, an AAV2 vector carrying the RPE65 gene is now an approved drug for the treatment of Leber's congenital amaurosis. Additionally, data from ongoing clinical trials supports the continued evaluation of AAV-based treatments for additional indications including hemophilia types A and B, Parkinson's disease, spinal muscular atrophy, and MPS I and II. Despite these encouraging results, expanding the use of in vivo gene therapy, especially in difficult to target organs such as the brain, is still hindered by delivery challenges.

SUMMARY OF THE INVENTION

The present disclosure is based, at least in part, on the identification of target proteins (e.g., Ly6 proteins) that enhance transcytosis of AAV capsids across the blood-brain barrier. The present disclosure provides, in some embodiments, methods for identifying AAV capsid proteins capable of crossing the blood-brain barrier, and compositions comprising such.

Some aspects of the present disclosure provide an AAV vector comprising an amino acid sequence that comprises at least 4 contiguous amino acids from a sequence listed in Table 4, 5, 6, 7, 8, 9, 10, 11, 12, 13, 14, 15, 16, 17, 18, or 19. Some aspects of the present disclosure provide an AAV vector comprising an amino acid sequence that is encoded by a nucleic acid sequence listed in any of the Tables included herein.

In some embodiments, the amino acid sequence is part of a capsid protein of the AAV vector. In some embodiments, the amino acid sequence is inserted at a position corresponding to the position between amino acids 586-592 of the sequence provided in SEQ ID NO: 730 or 731. In some embodiments, the amino acid sequence is inserted at a position corresponding to the position between amino acids 588-589 of the sequence provided in SEQ ID NO: 730 or 731.

In some embodiments, the AAV vector comprises at least 4 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV vector comprises a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204.

In some embodiments, the AAV vector comprises at least 4 contiguous amino acids of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the AAV vector comprises at least 4 contiguous amino acids of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482), RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522).

In some embodiments, the AAV vector comprises at least 4 contiguous amino acids of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSKLGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

In some embodiments, the AAV is an AAV9 vector. In some embodiments, the AAV vector is an AAV1, AAV2, AAV3, AAV4, AAV5, AAV6, AAV7, AAV8, AAV10 or AAV11 vector.

In some embodiments, the AAV vector comprises at least 5 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV vector comprises at least 6 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV vector comprises a sequence that is at least 80% identical to a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204.

In some embodiments, the the AAV vector comprises a sequence that contains a single amino acid substitution compared to a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204, and wherein the amino acid substitution is a conservative amino acid substitution In some embodiments, the AAV vector comprises at least 4 contiguous amino acids of: NSKTVVR (SEQ ID NO: 331), QRIQGQK (SEQ ID NO: 367), RGTRTEN (SEQ ID NO: 369), KLDKRMG (SEQ ID NO: 397), TRRDSLF (SEQ ID NO: 403), STKTVKL (SEQ ID NO: 420), LNNKQVR (SEQ ID NO: 454), RNTRTEA (SEQ ID NO: 479), GERSPRL (SEQ ID NO: 507), TPTNPRW (SEQ ID NO: 508), or SADRKHI (SEQ ID NO: 516).

In some embodiments, the amino acid sequence binds to a Ly6/uPAR protein. In some embodiments, the amino acid sequence specifically binds to a human Ly6/uPAR protein. In some embodiments, the amino acid sequence binds to a human Ly6/uPAR protein and binds to a non-human primate Ly6/uPAR protein. In some embodiments, the amino acid sequence binds to a human Ly6/uPAR protein, binds to a non-human primate Ly6/uPAR protein, and binds to a rodent Ly6/uPAR protein. In some embodiments, the Ly6/uPAR protein is CD59.

Some aspects of the present disclosure provide an AAV capsid protein comprising an amino acid sequence that comprises at least 4 contiguous amino acids from a sequence listed in Table 4, 5.6, 7, 8, 9, 10, 11, 12, 13, 14, 15, 16, 17, 18 or 19.

In some embodiments, the AAV capsid protein comprises at least 4 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV capsid protein comprises a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204.

In some embodiments, the AAV capsid protein comprises at least 4 contiguous amino acids of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the AAV capsid protein comprises at least 4 contiguous amino acids of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482), RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522).

In some embodiments, the AAV capsid protein comprises at least 4 contiguous amino acids of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSK-LGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

In some embodiments, the AAV capsid protein comprises at least 4 contiguous amino acids of: NSKTVVR (SEQ ID NO: 331), QRIQGQK (SEQ ID NO: 367), RGTRTEN (SEQ ID NO: 369), KLDKRMG (SEQ ID NO: 397), TRRDSLF (SEQ ID NO: 403), STKTVKL (SEQ ID NO: 420), LNNKQVR (SEQ ID NO: 454), RNTRTEA (SEQ ID NO: 479), GERSPRL (SEQ ID NO: 507), TPTNPRW (SEQ ID NO: 508), or SADRKHI (SEQ ID NO: 516).

In some embodiments, the AAV capsid protein further comprises a nanoparticle or second molecule to which said AAV capsid protein is conjugated. In some embodiments, the AAV capsid protein is part of an AAV. In some embodiments, the AAV capsid protein is part of an AAV9.

In some embodiments, the AAV capsid protein comprises the amino acid sequence inserted at a position corresponding to the position between amino acids 586-592 of the sequence provided in SEQ ID NO: 730 or 731. In some embodiments, the AAV capsid protein comprises the amino acid sequence inserted at a position corresponding to the position between amino acids 588-589 of the sequence provided in SEQ ID NO: 730 or 731.

In some embodiments, the AAV capsid protein is part of an AAV1, AAV2, AAV3, AAV4, AAV5, AAV6, AAV7, AAV8, AAV10 or AAV11.

In some embodiments, the AAV capsid protein comprises at least 5 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV capsid protein comprises at least 6 contiguous amino acids from a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the AAV capsid protein comprises a sequence that is at least 80% identical to a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204.

In some embodiments, the AAV capsid protein comprises a sequence that contains a single amino acid substitution compared to a sequence selected from SEQ ID NOs: 316-522, 732-1909, 3088-3199, 3312-6429, 9548-10086, 10626-10688, 10690-11520, 12481-12683, 12952-20446, 27942-

28880, 29819-29983, 30149-30166 and 30185-30204, and wherein the amino acid substitution is a conservative amino acid substitution.

In some embodiments, the AAV capsid protein comprises the amino acid sequence that binds to a Ly6/uPAR protein. In some embodiments, the AAV capsid protein comprises the amino acid sequence that specifically binds to a human Ly6/uPAR protein. In some embodiments, the AAV capsid protein comprises the amino acid sequence that binds to a human Ly6/uPAR protein and binds to a non-human primate Ly6/uPAR protein. In some embodiments, the AAV capsid protein comprises the amino acid sequence that binds to a human Ly6/uPAR protein, binds to a non-human primate Ly6/uPAR protein, and binds to a rodent Ly6/uPAR protein. In some embodiments, the AAV capsid protein comprises the amino acid sequence that binds to CD59.

Some aspects of the present disclosure provide a library of AAV9 capsid proteins comprising an AAV9 capsid protein as described herein.

Some aspects of the present disclosure provide a nucleic acid sequence encoding an AAV capsid protein as described herein.

Some aspects of the present disclosure provide a pharmaceutical composition comprising an AAV capsid protein as described herein and one or more pharmaceutical acceptable carriers.

Some aspects of the present disclosure provide a peptide comprising an amino acid sequence set forth in SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the peptide further comprises a nanoparticle or second molecule to which said peptide is conjugated.

Some aspects of the present disclosure provide a method of delivering a nucleic acid to a target environment of a subject in need, comprising providing a composition comprising an AAV vector, wherein the AAV vector comprises a capsid protein that comprises an amino acid sequence that comprises at least 4 contiguous amino acids of a sequence selected from a sequence listed in Table 4, 5, 6, 78, 9, 10, 11, 12, 13, 14, 15, 16, 17, 18, or 19, and wherein the AAV vector comprises a nucleic acid to be delivered to the target environment of the subject; and administering the composition to the subject.

In some embodiments, a method of delivering a nucleic acid to a target environment of a subject in need comprises providing a composition comprising any AAV vector described herein, and administering the composition to the subject.

In some embodiments, the target environment is the central nervous system, liver, muscle, heart, lungs, stomach, adrenal gland, adipose, intestine, or immune cells. In some embodiments, the target environment is neurons, astrocytes, cardiomyocytes, or a combination thereof.

In some embodiments, the nucleic acid to be delivered comprises one or more of: a) a nucleic acid sequence encoding a trophic factor, a growth factor, or a soluble protein; b) a cDNA that restores protein function to humans or animals harboring a genetic mutation(s) in that gene; c) a cDNA that encodes a protein that can be used to control or alter the activity or state of a cell; d) a cDNA that encodes a protein or a nucleic acid used for assessing the state of a cell; e) a cDNA and/or associated guide RNA for performing genomic engineering; f) a sequence for genome editing via homologous recombination; g) a DNA sequence encoding a therapeutic RNA; h) a shRNA or an artificial miRNA delivery system; and i) a DNA sequence that influences the splicing of an endogenous gene.

In some embodiments, the subject in need is a subject suffering from or at a risk to develop one or more of chronic pain, cardiac failure, cardiac arrhythmias, Friedreich's ataxia, Huntington's disease (HD), Alzheimer's disease (AD), Parkinson's disease (PD), Amyotrophic lateral sclerosis (ALS), spinal muscular atrophy types I and II (SMA I and II), Friedreich's Ataxia (FA), Spinocerebellar ataxia, lysosomal storage disorders that involve cells within the CNS.

In some embodiments, the AAV vector is administered to the subject via intravenous administration or systemic administration. In some embodiments, the nucleic acid is delivered to dorsal root ganglia, visceral organs, astrocytes, neurons, or a combination thereof of the subject.

Some aspects of the present disclosure provide a method comprising providing an AAV capsid protein; contacting the AAV capsid protein with a cell that expresses protein of Ly6/uPAR protein family attached to the surface of the cell; and selecting the AAV capsid protein if it specifically binds to the protein of the Ly6/uPAR protein family attached to the surface of the cell. In some embodiments, a method comprises any AAV capsid protein described herein.

In some embodiments, the protein of the Ly6/uPAR protein family is expressed recombinantly in the cell. In some embodiments, the protein of the Ly6/uPAR protein family is expressed endogenously in the cell. In some embodiments, the protein of the Ly6/uPAR protein family is a human protein. In some embodiments, the protein of the Ly6/uPAR protein family is expressed in the central nervous system. In some embodiments, the protein of the Ly6/uPAR protein family is LY6A, LY6C1, LY6E, CD59, Ly6H, LYNX1 or GPIHBP1. In some embodiments, the protein of the Ly6/uPAR protein family is ACRV1, CD177, CD59A, CD59B, GML, GML2, LY6A, LY6A2, LY6C1, LY6C2, LY6D, LY6E, LY6F, LY6G, LY6G2, LY6G5B, LY6G5C, LY6G6C, LY6G6D, LY6G6E, LY6G6F, LY6G6G, LY6I, LY6K, LY6L, LY6M, LYPD1, LYPD2, LYPD3, LYPD4, LYPD5, LYPD6, LYPD6B, LYPD8, LYPD9, LYPD10, LYPD11, PATE1, PATE2, PATE3, PATE4, PATE5, PATE6, PATE7, PATE8, PATE9, PATE10, PATE11, PATE12, PATE13, PATE14, PINLYP, PLAUR, PSCCA, SLURP1, SLURP2, SPACA4, or TEX101.

In some embodiments, the method comprises contacting the AAV capsid protein with a cell that expresses a GPI-anchored protein.

In some embodiments, the method is a method for identifying an AAV capsid protein that can cross the blood-brain barrier.

Some aspects of the present disclosure provide a method comprising providing a targeting peptide; incubating the targeting peptide with a protein of the Ly6/uPAR protein family; and selecting the targeting peptide if it specifically binds to the protein of the Ly6/uPAR protein family. In some embodiments, the protein of the Ly6/uPAR protein family is a fusion protein. In some embodiments, the protein of the Ly6/uPAR protein family is an Fc fusion. In some embodiments, the protein of the Ly6/uPAR protein family forms a dimer. In some embodiments, the protein of the Ly6/uPAR protein family is fused to a: AviTag, C-tag, Calmodulin-tag, E-tag, FLAG, HA, poly-HIS, MYC, NE, Rho1D4, S-tag, SBP, Softag, Spot-tag, T7-tag, TC, Ty, V5, VSV, Xpress, Isopeptag, SpyTag, SnoopTag, DogTag, SdyTag, BCCP, GST, GFP, Halo, SNAP, CLIP, Maltose binding protein (MBP), Nus-tag, Thioredoxin-tag, Fc-tag, CRDSAT, SUMO-tag, or B2M-tag. In some embodiment, the method as described herein is conducted in vitro.

In some embodiments, the targeting peptide is expressed within an AAV capsid protein. In some embodiments, the targeting peptide is expressed within an AAV9 capsid protein. In some embodiments, the targeting peptide is contained within an AAV capsid protein described herein. In some embodiments, the targeting peptide comprises at least 4 contiguous amino acids of an amino acid sequence set forth in SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, the targeting peptide comprises an amino acid sequence set forth in SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204.

Some aspects of the present disclosure provide a method comprising delivering a protein, RNA, or DNA to a target environment of a subject and administering an adeno-associated virus (AAV) vector to the target environment of the subject. In some embodiments, the AAV vector comprises a capsid protein comprising at least 4 contiguous amino acids from a sequence listed in Table 4, 5, 6, 7, 8, 9, 10, 11, 12, 13, 14, 15, 16, 17, 18, or 19. In some embodiments, the AAV vector comprises a nucleic acid molecule to be delivered to the target environment of the subject. In some embodiments, the protein that is delivered is a LY6/uPAR protein. In some embodiments, the DNA or RNA that is delivered encodes a Ly6/uPAR protein. In some embodiments, the method as described herein is a method of treating a disorder or defect in a subject. In some embodiments, the nucleic acid molecule to be delivered to the target environment of the subject encodes a therapeutic protein. In some embodiments, the nucleic acid molecule is a therapeutic. In some embodiments, the therapeutic protein is effective for treating the disorder or defect in the subject. In some embodiments, the nucleic acid molecule is effective for treating the disorder or defect in the subject. In some embodiments, the LY6/uPAR protein is LY6A. In some embodiments, the LY6/uPAR protein is LY6C1. In some embodiments, the LY6/uPAR protein is a murine protein. In some embodiments, the AAV is a murine AAV. In some embodiments, the AAV targets the Ly6/uPAR protein.

In some embodiments, the nucleic acid molecule to be delivered comprises one or more of: a) a nucleic acid sequence encoding a trophic factor, a growth factor, or a soluble protein; b) a cDNA that restores protein function to humans or animals harboring a genetic mutation(s) in that gene; c) a cDNA that encodes a protein that can be used to control or alter the activity or state of a cell; d) a cDNA that encodes a protein or a nucleic acid used for assessing the state of a cell; e) a cDNA and/or associated guide RNA for performing genomic engineering; f) a sequence for genome editing via homologous recombination; g) a DNA sequence encoding a therapeutic RNA; h) a shRNA or an artificial miRNA delivery system; and i) a DNA sequence that influences the splicing of an endogenous gene. In some embodiments, the method as disclosed herein is a diagnostic method.

In some embodiments, the disorder or defect is one or more of chronic pain, cardiac failure, cardiac arrhythmias, Friedreich's ataxia, Huntington's disease (HD), Alzheimer's disease (AD), Parkinson's disease (PD), Amyotrophic lateral sclerosis (ALS), spinal muscular atrophy types I and II (SMA I and II), Friedreich's Ataxia (FA), Spinocerebellar ataxia, and lysosomal storage disorders that involve cells within the CNS.

In some embodiments, the protein, RNA, or DNA is delivered to the subject via intravenous administration or systemic administration. In some embodiments, the AAV vector is administered to the subject via intravascular administration or systemic administration. In some embodiments, the protein, RNA, or DNA is delivered to the subject in trans. In some embodiments, the present method provides that the protein, RNA, or DNA is delivered to the subject via a nanoparticle. In some embodiments, the RNA or DNA is delivered to the subject via a viral vector. In some embodiments, the protein delivered to the subject is a purified protein.

In some embodiments, the method provides that the protein, RNA, or DNA is delivered to the target environment first, followed by the administration of the AAV vector. In some embodiments, the delivering of the protein or RNA to the target environment and the administering of the AAV vector occur simultaneously. In some embodiments, the protein, RNA, or DNA is delivered in a targeted fashion to a target organ, region of an organ, tumor, ganglia, or to the cerebral spinal fluid of the subject.

Some aspects of the present disclosure provide a method of providing an adeno-associated virus (AAV) capsid protein; contacting the AAV capsid protein with a cell that expresses a GPI-anchored protein attached to the surface of the cell; and selecting the AAV capsid protein if it specifically binds to the GPI-anchored protein attached to the surface of the cell. Some aspects of the present disclosure provide a method of providing an adeno-associated virus (AAV) capsid protein; contacting the AAV capsid protein with a cell that expresses a protein attached to the surface of the cell; and selecting the AAV capsid protein if it specifically binds to the protein attached to the surface of the cell.

In some embodiments, the protein attached to the surface of the cell is: i) a protein that exhibits luminal surface exposure on brain endothelium; ii) a protein that is localized within lipid micro-domains; and/or iii) a protein that exhibits recycling/intracellular trafficking capabilities.

Some aspects of the present disclosure provides a method of providing a targeting peptide; incubating the targeting peptide with a GPI-anchored protein; and selecting the targeting peptide if it specifically binds to the GPI-anchored protein. In some embodiments, the method provides that the targeting peptide is contained within an adeno-associated virus (AAV) capsid protein.

Some aspects of the present disclosure provide a method of providing an adeno-associated virus (AAV) capsid protein; contacting the AAV capsid protein with a cell that expresses a surface protein; and selecting the AAV capsid protein if it specifically binds to the surface protein. In some embodiments, the surface protein is a GPI-anchored protein. In some embodiments, the GPI-anchored protein is a Ly6/uPAR protein. In some embodiments, the surface protein is a protein that traffics to the plasma membrane. In some embodiments the surface protein is expressed recombinantly in the cell. In some embodiments, next-generation sequencing is used to determine peptide disclosed herein. In some embodiments, targeting peptides disclosed herein do not have the sequence of SEQ ID NO: 10689 (YTLSQGW).

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIGS. 12A-B show name, chromosomal location, number of exons, and LU domains for human Ly6/uPAR family genes. (Adapted from Loughner et al. (2016) *Human Genomics* 10:10.)

DETAILED DESCRIPTION

Figure 1A:
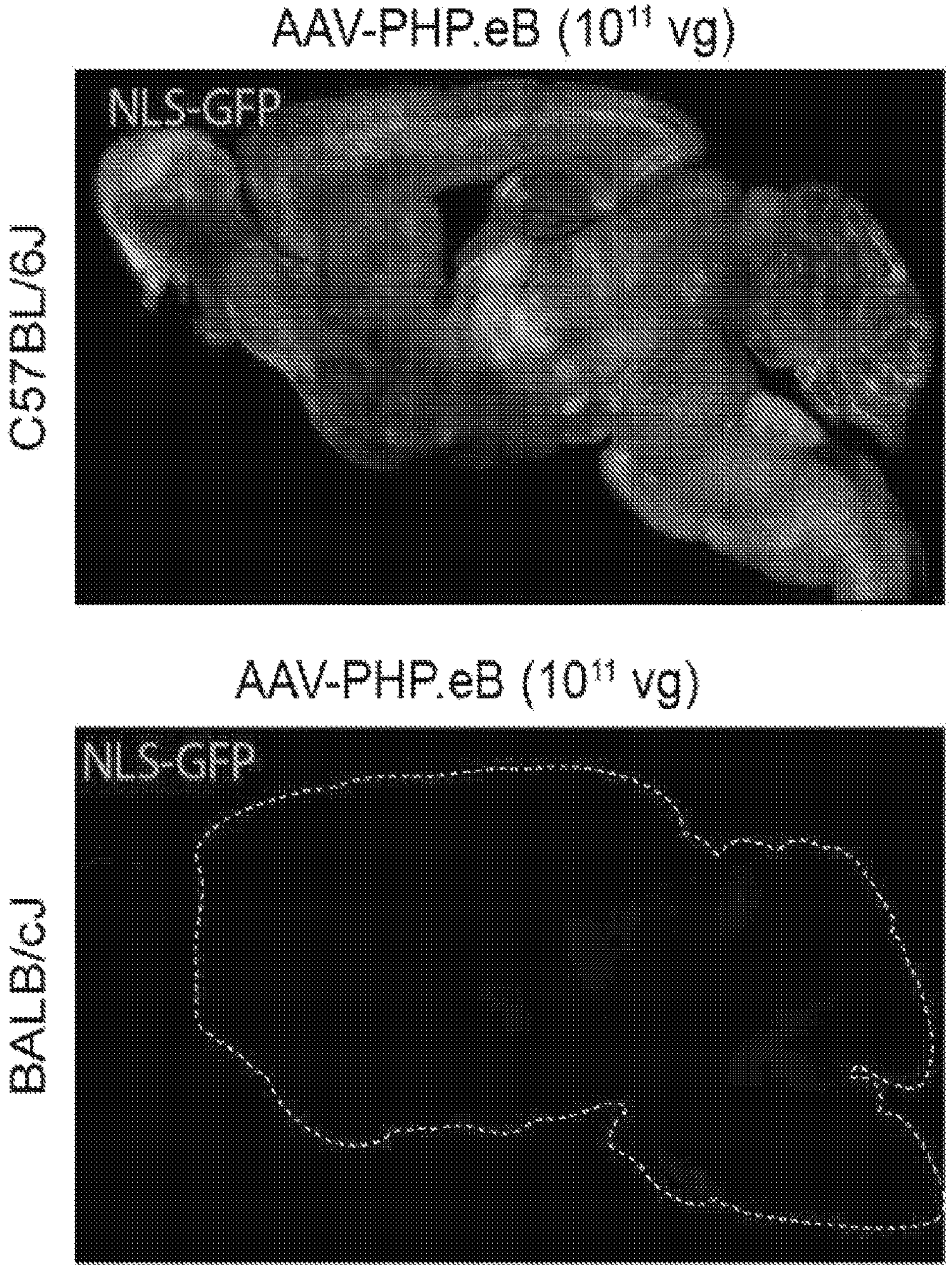
FIG. 1A shows images of GFP fluorescence within sagittal brain sections from C57BL/6J (top) or BALB/cJ (bottom) two weeks after intravenous administration of AAV-PHP.eB:CAG-NLS-GFP.

Aspects of the present disclosure relate to methods for identifying targeting peptides that enhance transcytosis of AAV capsids across the blood-brain barrier via binding to target proteins such as Ly6/uPAR proteins. Accordingly, methods and compositions described herein are useful, in some embodiments, for in vivo gene therapy.

Adeno-Associated Virus (AAV) Vectors

Aspects of the invention relate to adeno-associated virus (AAV) vectors and their use in gene therapy. AAV vectors described herein can be used to deliver a nucleic acid encoding a protein of interest to a subject, including delivery to the central nervous system (CNS) of a subject. AAV vectors are described further in U.S. Pat. No. 9,585,971 and US 2017/0166926, which are incorporated by reference herein in their entireties.

AAV refers to a replication-deficient Dependoparvovirus within the Parvoviridae genus of viruses. AAV can be derived from a naturally occurring virus or can be recombinant. AAV can be packaged into capsids, which can be derived from naturally occurring capsid proteins or recombinant capsid proteins. The single-stranded DNA genome of AAV includes inverted terminal repeat (ITRs), which are involved in integrating the AAV DNA into the host cell genome. In some embodiments, AAV integrates into a host cell genome, while in other embodiments, AAV is non-integrating. AAV vectors can comprise: one or more ITRs, including, for example a 5' ITR and/or a 3' ITR; one or more promoters; one or more nucleic acid sequences encoding one or more proteins of interest; and/or additional posttranscriptional regulator elements. AAV vectors described herein can be prepared using standard molecular biology techniques known to one of ordinary skill in the art, as described, for example, in Sambrook et al. (Molecular Cloning: A Laboratory Manual. Cold Spring Harbor Laboratory Press, N.Y. (2012)).

AAV vectors described herein can include sequences from any known organism and can include synthetic sequences. AAV vector sequences can be modified in any way known to one of ordinary skill in the art, such as by incorporating insertions, deletions or substitutions, and/or through the use of posttranscriptional regulatory elements, such as promoters, enhancers, and transcription and translation terminators, such as polyadenylation signals. AAV vectors can also include sequences related to replication and integration. In some embodiments, AAV vectors include a shuttle element for replication and integration.

AAV vectors can include any known AAV serotype, including, for example, AAV1, AAV2, AAV3, AAV4, AAV5, AAV6, AAV7, AAV8, AAV9, AAV10, and AAV11. In some embodiments, the AAV serotype is AAV9. Clades of AAV viruses are described in, and incorporated by reference, from Gao et al. (2004) J. Virol. 78(12):6381-6388.

AAV vectors of the present disclosure may comprise or be derived from any natural or recombinant AAV serotype. In some embodiments, the AAV vector may utilize or be based on an AAV serotype described in WO 2017/201258A1, the contents of which are incorporated herein by reference in its entirety, such as, but not limited to, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37. AAV114.3/hu.40, AAV127.2/hu.41, AAV127.5/hu.42, AAV128.3/hu.44, AAV130.4/hu.48. AAV145.1/hu.53, AAV145.5/hu.54, AAV145.6/hu.55, AAV161.10/hu.60, AAV161.6/hu.61.

AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4. AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2. AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4. AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11. AAVF12/HSC12, AAVF13/HSC13, AAVF14/HSC14, AAVF15/HSC15, AAVF16/HSC16. AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B (PHP.B), AAV-PHP.A (PHP.A), G2B-26, G2B-13, TH1.1-32 and/or TH1.1-35, and variants thereof.

AAV vectors disclosed herein comprise targeting sequences (e.g., 7-mer sequences) capable of directing the AAV vectors to specific environments within a subject, including, in some embodiments, directing the AAV vectors across the blood-brain barrier in a subject. In some embodiments, the targeting sequence is inserted into the capsid protein of the AAV vector. The targeting sequence can be inserted into any region of the capsid protein. In some embodiments, the targeting sequence is inserted at a position corresponding to the position between amino acids 588 and 589 of an AAV9 capsid protein, such as a capsid protein provided in SEQ ID NO: 730 or 731. In some embodiments, the targeting sequence is inserted at a position corresponding to a position between amino acids 586 and 592 of an AAV9 capsid protein, such as a capsid protein provided in SEQ ID NO: 730 or 731.

As used herein, a position (such as a nucleic acid residue or an amino acid residue) in sequence "X" is referred to as corresponding to a position or residue (such as a nucleic acid residue or an amino acid residue) "a" in sequence "Y" when the residue in sequence "X" is at the counterpart position of "a" in sequence "Y" when sequences X and Y are aligned using amino acid sequence alignment tools known in the art, such as, for example, Clustal Omega or BLAST®. One of ordinary skill in the art would be able to determine a position in a given protein that corresponds to the position between amino acids 588 and 589 of an AAV9 capsid protein, or a position between amino acids 586 and 592 of an AAV9 capsid protein, such as a capsid protein provided in SEQ ID NO: 730 or 731, using methods known in the art.

Aspects of the present disclosure, in some embodiments, provide an AAV vector comprising an amino acid sequence that comprises at least 4 contiguous amino acids from a sequence listed in Table 4, 5, 6, 78, 9, 10, 11, 12, 13, 14, 15, 16, 17, 18, or 19. In some embodiments, the AAV vector comprises at least 4 contiguous amino acids, at least 5 contiguous amino acids, or at least 6 contiguous amino acids of a sequence selected from SEQ ID NOs: 316-522, 732-1909, 3088-3199, 3312-6429, 9548-10086, 10626-10688, 10690-11520, 12481-12683, 12952-20446, 27942-28880, 29819-29983, 30149-30166 and 30185-30204. In some embodiments, an AAV vector comprises a sequence selected from SEQ ID NOs: 316-30,204. In some embodiments, any sequence selected from SEQ ID NOs: 316-30,204 is compatible with aspects of the disclosure, including in some embodiments insertion into AAV vectors as described herein.

In some embodiments, the AAV vector comprises at least 4 contiguous amino acids, at least 5 contiguous amino acids, or at least 6 contiguous amino acids of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the AAV vector comprises at least 4 contiguous amino acids, at least 5 contiguous amino acids, or at least 6 contiguous amino acids of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482), RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522). In some embodiments, the AAV vector comprises at least 4 contiguous amino acids, at least 5 contiguous amino acids, or at least 6 contiguous amino acids of any of sequences listed in Table 4, 5, 6, 7, 8, 9, 10, 11, 12, 13, 14, 15, 16, 17, 18, or 19.

In some embodiments, the AAV vector comprises at least 4 contiguous amino acids, at least 5 contiguous amino acids, or at least 6 contiguous amino acids of any one of: SEQ ID NO: 732-1909, SEQ ID NO: 3088-3199, SEQ ID NO: 3312-6429, SEQ ID NO: 9548-10086, 1 SEQ ID NO: 0626-10688, SEQ ID NO: 10690-11520, SEQ ID NO: 12481-12683, SEQ ID NO: 12952-20446, SEQ ID NO: 27942-28880, SEQ ID NO: 29819-29983, SEQ ID NO: 30149-30166, or SEQ ID NO: 30185-30204. In some embodiments, the AAV vector does not comprise SEQ ID NO: 10689 (YTLSQGW).

In some embodiments, the AAV vector comprises at least 4 contiguous amino acids, at least 5 contiguous amino acids, or at least 6 contiguous amino acids of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSKLGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

Aspects of the invention relate to AAV capsid proteins. AAV capsid proteins described herein may have a sequence that is different from the corresponding wild type AAV capsid protein sequence or is different from a reference AAV capsid protein sequence. An AAV capsid protein can include an insertion, deletion, or substitution of one or more nucleotides or one or more amino acids relative to the corresponding wild type AAV capsid protein sequence or relative to a reference AAV capsid protein sequence. The insertion, deletion, or substitution of one or more nucleotides or one or more amino acids can be at the 5' end, the 3' end and/or internally within the capsid sequence.

In some embodiments, the AAV capsid protein comprising at least 4, at least 5 contiguous amino acids, or at least 6 contiguous amino acids contiguous amino acids of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the AAV capsid protein comprises at least 4 contiguous amino acids, at least 5 contiguous amino acids, or at least 6 contiguous amino acids of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482). RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522).

In some embodiments, the AAV capsid protein comprises at least 4 contiguous amino acids, at least 5 contiguous amino acids, or at least 6 contiguous amino acids of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSKLGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

The nucleotide sequence of an AAV capsid protein can be at least about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more than 99%, inclusive of all ranges and subranges therebetween, identical to a wild type AAV capsid nucleotide sequence or a reference AAV capsid nucleotide sequence. The protein sequence of an AAV capsid protein can be at least about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more than 99%, inclusive of all ranges and subranges there between, identical to a wild type AAV capsid protein sequence or a reference AAV capsid protein sequence.

Also disclosed herein are libraries of AAV capsid proteins, such as AAV9 capsid proteins. As used herein, a "library" of AAV capsid proteins refers to a collection of at least two AAV capsid proteins. In some embodiments, at least one of the AAV capsid proteins within the library includes an insertion of a targeting sequence (e.g., a 7-mer). In some embodiments, at least one of the AAV capsid proteins within the library includes an insertion of a targeting sequence selected from the targeting sequences in Table 4, 5, 6, 7, 8, 9, 10, 11, 12, 13, 14, 15, 16, 17, 18, or 19.

The AAV capsid protein can, in some embodiments, include one or more amino acid substitutions relative to the corresponding wildtype AAV capsid protein provided in SEQ ID NO: 730, including but not limited to, a K449R substitution, a A587D substitution, a Q588G substitution, a A587G substitution, a Q588G substitution, a V592T substitution, a K595S substitution, a A595N substitution, a Q597P substitution, or any combination thereof. An example an AAV capsid protein comprising a K449R substitution is provided in SEQ ID NO: 731. Amino acid modifications of AAV capsid proteins are described further in, and incorporated by reference from Li et al. (2012) Journal of Virology 86(15): 7752-7759. Sequences of AAV9 capsid proteins are further described in, and incorporated by reference from U.S. Pat. No. 7,198,951, assigned to The Trustees of the University of Pennsylvania.

The targeting sequences disclosed herein, in some embodiments, can increase transduction efficiency of an AAV across the blood-brain barrier in a subject relative to an AAV that does not contain the targeting sequence. For example, the inclusion of one or more of the targeting sequences disclosed herein in an AAV can result in an increase in transduction efficiency by at least 5%, 10%, 20%, 30%, 40%, 50%, 60%, 70%, 80%, 90%, 100%, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 10-fold, 20-fold, 30-fold, 40-fold, 50-fold, 60-fold, 70-fold, 80-fold, 90-fold, 100-fold, or more than 100-fold, including all values in between, relative to an AAV that lacks the targeting sequence. In some embodiments, the transduction efficiency is increased for transducing AAV to the blood-brain barrier. In some embodiments, the transduction efficiency is increased for transducing AAV to the CNS. In some embodiments, the transduction efficiency is increased for transducing AAV to the PNS. In some embodiments, the transduction efficiency is increased for transducing AAV to the heart. In some embodiments, the transduction efficiency is increased for transducing AAV to cardiomyocytes, sensory neurons, dorsal root ganglia, visceral organs, or any combination thereof. In some embodiments, the transduction efficiency is increased for transducing AAV to any target environment suitable for the delivery of AAV vectors.

In some embodiments, an AAV9 capsid protein, or a library of AAV9 capsid proteins, is provided in which the AAV9 genome contains the viral replication gene (rep) and capsid gene (cap) that have been modified so as to not prevent the replication of the virus under conditions in which it could normally replicate. In some embodiments, an AAV9 capsid protein, or a library of AAV9 capsid proteins, is provided in which the AAV9 genome contains an engineered cap gene. In some embodiments, an AAV9 capsid protein, or a library of AAV9 capsid proteins, is provided in which the AAV9 genome contains the rep cap genes are flanked by ITRs. In some embodiments, an AAV genome contains the cap gene and contains rep gene sequences that are involved in regulating expression and/or splicing of the cap gene. In some embodiments, a capsid gene recombinase recognition sequence is provided, optionally with flanking ITRs.

Libraries of AAV capsid proteins, such as AAV9 capsid proteins, described herein, can be used to select for AAV capsid proteins that exhibit, e.g.: enhanced targeting to specific cells or organs; evasion of immunity; efficiency at homologous recombination; efficiency of conversion of the single stranded AAV genome to a double stranded DNA genome within a cell; and/or increased conversion of an AAV genome to a persistent, circularized form within the cell.

Targeting Peptides

Aspects of the invention relate to targeting peptides that can direct AAV, e.g., to a specific target environment. In some embodiments, the target environment is a cell (e.g., neuron). In some embodiments, the target environment is neurons, astrocytes, cardiomyocytes, or a combination thereof. In some embodiments, the target environment is an organ (e.g., heart, brain). In some embodiments, the targeting peptide directs AAV to the central nervous system (CNS) of a subject. The CNS includes, e.g., brain tissue, nerves (e.g., optic nerves or cranial nerves), and fluid (e.g., cerebrospinal fluid). In some embodiments, the targeting peptide directs AAV to the peripheral nervous system (PNS) of a subject. Targeting peptides can be conjugated to other components, such as a nanoparticle or a viral capsid protein.

In some embodiments, the targeting peptide comprises an amino acid consensus motif selected from the group consisting of (T/S)-(L/I/V/M)-(A/x)-(V/x)-P-F-K, (SIT)-(V/x)-(S/T/x)-(K/R)-P-F-(L/I/V/A), x-x-x-F-K-(D/N)-(I/V/P), x-(K/R/Y)-(x/R/K/Y/F)-(G/Y/K/R/x)-(Y/W/F/L/M)-(S/A)-(S/T/A/Q), S-X-X-G-W-(V/A/S/T/I/L)-(A/P), Y-X-X-X-X-(G/S)-W, K-X-X-G/X-S-(V/I/Y/F/M)-Y, R-(F/Y)-X-(G/S)-(D/E)-(S/A/P/N/G)(S/A/G/T/V/I/Q), X-X-X-G-(Y/F/W)-S-(Q/S/T/A/M), X-X-X-P-G-V-W, G-X-X-X-G-R-W, (D/E)-(V/G/D/P/L/N/A)-(G/P/A/T/D/N/L)-S-G-R-W, S-(P/UY/E/G/T/D/A)-(G/N/S/D/V/T/H)-(D/S/G/E/P/V/Y/I)-(G/A/S/N/V/A)-R-W, X-X-Y-X-G-S-(S/T/V/A/M/Q/I/H)R-(TVL)-(S/G)-(A/S)-(G/N/x)-(S/G/M/x)-(T/S), G-S-G-T-V-(K/R)-X, Q-N-R-X-X-Y-V, Y-H-P-(L/M)-D-(V/P/I/R/K/UM/W)-(T/S), and X-X-(F/W)-X-P-P-S, where x is any amino acid.

In some embodiments, the targeting peptide comprises an amino acid consensus motif selected from the group consisting of (T/S)-(L/I/V/M)-(A/x)-(V/x)-P-F-K, (SIT)-(V/x)-(S/T/x)-(K/R)-P-F-(L/I/V/A), x-x-x-F-K-(D/N)-(I/V/P), x-(K/R/Y)-(x/R/K/Y/F)-(G/Y/K/R/x)-(Y/W/F/L/M)-(S/A)-(S/T/A/Q), F-T-(hydrophobic)-x-x-P-K, (S/T/x)-x-x-x-P-F-(R/K), G-x-(F/W)-x-P-P-x, (T/S/X)-X-X-(R/K)-P-F-(I/L/V/Q/H/S/T/M/A), P-(S/T/X)-(S/T/X)-(S/T/X)-(S/T/X)-(S/T)-W, (S/G)-X-X-G-W-A-P, L-T-(hydrophobic)-x-T-S-(V/I/K/R), X-X-(K/R)-F-E-X-(I/V/M), X-X-(F/W)-X-P-P-S, S-X-X-G-W-(V/A/S/T/I/L)-(A/P), Y-X-X-X-X-(G/S)-W, K-X-X-G/X-S-(V/I/Y/F/M)-Y, R-(F/Y)-X-(G/S)-(D/E)-(S/A/P/N/G)(S/A/G/T/V/I/Q), X-X-X-G-(Y/F/W)-S-(Q/S/T/A/M), X-X-X-P-G-V-W, G-X-X-X-G-R-W, (D/E)-(V/G/D/P/L/N/A)-(G/P/A/T/D/N/L)-S-G-R-W, S-(P/L/Y/E/G/T/D/A)-(G/

N/S/D/V/T/H)-(D/S/G/E/P/V/Y/I)-(G/A/S/N/V/A)-R-W, X-X-Y-X-G-S-(S/T/V/A/M/Q/I/H), R-(TVL)-(S/G)-(A/S)-(G/N/x)-(S/G/M/x)-(T/S), G-S-G-T-V-(K/R)-X, Q-N-R-X-X-Y-V, and Y-H-P-(L/M)-D-(V/P/I/R/K/L/M/W)-(T/S), where x is any amino acid.

Targeting peptides, as described herein, may be various lengths. In some embodiments, the targeting peptide comprises 4 amino acids (e.g., 4-mer). In some embodiments, the targeting peptide comprises 5 amino acids (e.g., 5-mer). In some embodiments, the targeting peptide comprises 6 amino acids (e.g., 6-mer). In some embodiments, the targeting peptide comprises 7 amino acids (e.g., 7-mer). In some embodiments, the targeting peptide comprises 8 amino acids (e.g., 8-mer). In some embodiments, the targeting peptide comprises 9 amino acids (e.g., 9-mer). In some embodiments, the targeting peptide comprises 10 amino acids (e.g., 10-mer). In some embodiments, the targeting peptide comprises less than 4 or more than 10 amino acids. In some embodiments, the targeting peptide can be any length comprising any numbers of amino acids that are suitable for the incorporation into AAV vectors.

Targeting peptides, as described herein, may be charged or uncharged. In some embodiments, the targeting peptide is positively charged. In some embodiments, the targeting peptide is negatively charged. In some embodiments, the targeting peptide is neutrally charged. In some embodiments, the targeting peptide is uncharged.

Targeting peptides, as described herein, may comprise positively charged amino acids and negatively charged amino acids in various ratios. In some embodiments, the targeting peptide comprises positively charged amino acids and negatively charged amino acids in a 0:1 or 1:0 ratio. In some embodiments, the targeting peptide comprises positively charged amino acids and negatively charged amino acids in a 1:1, 2:1, 3:1, or 4:1 ratio. In some embodiments, the targeting peptide comprises positively charged amino acids and negatively charged amino acids in a 1:2, 1:3, or 1:4 ratio. In some embodiments, the targeting peptide comprises at least one negatively charged amino acids (e.g., arginine) and at least one hydrophobic amino acid residue (e.g., leucine). In some embodiments, the targeting peptide comprises two arginine residues and two leucine residues.

In some embodiments, the targeting peptide comprises an amino acid consensus motif consisting of (T/S)-(L/I/V/M)-(A/x-V/x-P-F-K) (SEQ ID NO: 30225), where x is any amino acid. In some embodiments, the targeting peptide comprises an amino acid sequence selected from the group consisting of SEQ ID NOs: 20-33. In some embodiments, the targeting peptide is encoded by a nucleic acid sequence selected from the group consisting of SEQ ID NOs: 34-47.

In some embodiments, the targeting peptide comprises an amino acid consensus motif consisting of (S/T)-(V/x)-(S/T/x)-(K/R)P-F-(L/I/V/A) (SEQ ID NO: 30226), where x is any amino acid. In some embodiments, the targeting peptide comprises an amino acid sequence selected from the group consisting of SEQ ID NOs: 48-77. In some embodiments, the targeting peptide is encoded by a nucleic acid sequence selected from the group consisting of SEQ ID NOs: 78-107.

In some embodiments, the targeting peptide comprises an amino acid consensus motif consisting of x-x-x-F-K-(D/N)-(I/V/P) (SEQ ID NO: 30227), where x is any amino acid. In some embodiments, the targeting peptide comprises an amino acid sequence selected from the group consisting of SEQ ID NOs: 108-119. In some embodiments, the targeting peptide is encoded by a nucleic acid sequence selected from the group consisting of SEQ ID NOs: 120-131.

In some embodiments, the targeting peptide comprises an amino acid consensus motif consisting of x-(K/R/Y)-(x/R/K/Y/F)-(G/Y/K/R/x)-(Y/W/F/L/M)-(S/A)-(S/T/A/Q) (SEQ ID NO: 30228), where x is any amino acid. In some embodiments, the targeting peptide comprises an amino acid sequence selected from the group consisting of SEQ ID NOs: 132-218. In some embodiments, the targeting peptide is encoded by a nucleic acid sequence selected from the group consisting of SEQ ID NOs: 219-305.

In some embodiments, the targeting peptide comprises an amino acid consensus motif consisting of R-(TVL)-(S/G)-(A/S)-(G/N/x)-(S/G/M/x)-(T/S) (SEQ ID NO: 30280), where x is any amino acid. In some embodiments, the targeting peptide comprises an amino acid sequence selected from the group consisting of SEQ ID NOs: 30149-30155.

In some embodiments, the targeting peptide comprises an amino acid consensus motif consisting of G-S-G-T-V-(K/R)-X (SEQ ID NO: 30281), where x is any amino acid. In some embodiments, the targeting peptide comprises an amino acid sequence selected from the group consisting of SEQ ID NOs: 30156-20160.

In some embodiments, the targeting peptide comprises an amino acid consensus motif consisting of Q-N-R-X-X-Y-V (SEQ ID NO: 30282), where x is any amino acid. In some embodiments, the targeting peptide comprises an amino acid sequence selected from the group consisting of SEQ ID NOs: 30161-30162.

In some embodiments, the targeting peptide comprises an amino acid consensus motif consisting of Y-H-P-(L/M)-D-(V/P/I/R/K/L/M/W)-(T/S) (SEQ ID NO: 30283), where x is any amino acid. In some embodiments, the targeting peptide comprises an amino acid sequence selected from the group consisting of SEQ ID NOs: 30185-30204.

In some embodiments, the targeting peptide comprises at least 4 contiguous amino acids, at least 5 contiguous amino acids, or at least 6 contiguous amino acids of a sequence selected from SEQ ID NOs: 306-310. In some embodiments, the targeting peptide is encoded by a nucleic acid sequence selected from the group consisting of SEQ ID NOs: 311-315.

In some embodiments, the targeting peptide comprises an amino acid sequence selected from the group consisting of SEQ ID NOs: 316-30204. In some embodiments, the targeting peptide is encoded by a nucleic acid sequence selected from the group consisting of SEQ ID NOs: 523-729.

In some embodiments, the targeting peptide comprises at least 4 contiguous amino acids, at least 5 contiguous amino acids, or at least 6 contiguous amino acids of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the targeting peptide comprises at least 4 contiguous amino acids, at least 5 contiguous amino acids, or at least 6 contiguous amino acids of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482), RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522).

In some embodiments, the targeting peptide comprises at least 4 contiguous amino acids, at least 5 contiguous amino acids, or at least 6 contiguous amino acids of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSK-LGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

In some embodiments, the targeting peptide comprises at least 4 contiguous amino acids, at least 5 contiguous amino acids, or at least 6 contiguous amino acids of any one of: SEQ ID NO: 732-1909, SEQ ID NO: 3088-3199, SEQ ID NO: 3312-6429, SEQ ID NO: 9548-10086, 1 SEQ ID NO: 0626-10688, SEQ ID NO: 10690-11520, SEQ ID NO: 12481-12683, SEQ ID NO: 12952-20446, SEQ ID NO: 27942-28880, SEQ ID NO: 29819-29983, SEQ ID NO: 30149-30166, or SEQ ID NO: 30185-30204.

In some embodiments, the targeting peptide comprises at least 4 contiguous amino acids, at least 5 contiguous amino acids, or at least 6 contiguous amino acids from a sequence selected from the group consisting of SEQ ID NOs: 20-33, SEQ ID NOs: 48-77, SEQ ID NOs: 108-119, SEQ ID NOs: 132-218. SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide comprises at least 5 contiguous amino acids from a sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide comprises at least 6 contiguous amino acids from a sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide comprises 7 contiguous amino acids from a sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204.

In some embodiments, the targeting peptide is at least 75% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide is at least 80% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide is at least 85% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522. SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide is at least 90% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide is at least 95% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide is at least 98% identical to an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204.

In some embodiments, the targeting peptide comprises at least 1 amino acid substitution in an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide comprises at least 2 amino acid substitutions in an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the targeting peptide comprises at least 3, at least 4, at least 5, or at least 6, or at least 7 amino acid substitutions in an amino acid sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204. In some embodiments, the at least one amino acid substitution is a conservative amino acid substitution.

In some embodiments, a targeting peptide contains one or more amino acid substitutions relative to a sequence disclosed in Table 4, 5, 6, 7, 8, 9, 10, 11, 12, 13, 14, 15, 16, 17, 18, or 19. In some embodiments, the amino acid substitution is a conservative amino acid substitution. As used herein, a "conservative amino acid substitution" refers to an amino acid substitution that does not alter the relative charge or size characteristics or functional activity of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Non-limiting examples of conservative amino acid substitutions are provided in Table 8.

TABLE 8

Non-limiting Examples of Conservative Amino Acid Substitutions

| Original Residue | R Group Type | Conservative Amino Acid Substitutions |
|---|---|---|
| Ala | nonpolar aliphatic R group | Cys, Gly, Ser |
| Arg | positively charged R group | His, Lys |
| Asn | polar uncharged R group | Asp, Gln, Glu |
| Asp | negatively charged R group | Asn, Gln, Glu |
| Cys | polar uncharged R group | Ala, Ser |
| Gln | polar uncharged R group | Asn, Asp, Glu |
| Glu | negatively charged R group | Asn, Asp, Gln |
| Gly | nonpolar aliphatic R group | Ala, Ser |
| His | positively charged R group | Arg, Tyr, Trp |
| Ile | nonpolar aliphatic R group | Leu, Met, Val |
| Leu | nonpolar aliphatic R group | Ile, Met, Val |
| Lys | positively charged R group | Arg, His |
| Met | nonpolar aliphatic R group | Ile, Leu, Phe, Val |
| Pro | polar uncharged R group | |
| Phe | nonpolar aromatic R group | Met, Trp, Tyr |
| Ser | polar uncharged R group | Ala, Gly, Thr |
| Thr | polar uncharged R group | Ala, Asn, Ser |
| Trp | nonpolar aromatic R group | His, Phe, Tyr, Met |
| Tyr | nonpolar aromatic R group | His, Phe, Trp |
| Val | nonpolar aliphatic R group | Ile, Leu, Met, Thr |

In some embodiments, a targeting peptide comprises one or more of the sequences disclosed herein. In other embodiments, a targeting peptide consists of one or more of the sequences disclosed herein. In other embodiments, a targeting peptide consists essentially of one or more of the sequences disclosed herein. Targeting peptides described herein can be fused to or inserted into longer peptides. In some embodiments, targeting peptides are isolated. In some embodiments, targeting peptides are not naturally occurring.

Also disclosed herein are nucleic acid sequences that encode one or more of the targeting peptides disclosed herein. In some embodiments, a nucleic acid sequence encoding a targeting peptide comprises or consists of a sequence selected from the group consisting of SEQ ID NOs: 20-33, SEQ ID NOs: 48-77, SEQ ID NOs: 108-119, SEQ ID NOs: 132-218, SEQ ID NOs: 306-310, SEQ ID NOs: 316-522, SEQ ID NOs: 732-1909, SEQ ID NOs: 3088-3199, SEQ ID NOs: 3312-6429, SEQ ID NOs: 9548-10086, SEQ ID NOs: SEQ ID NOs: 10626-10688, SEQ ID NOs: 10690-11520, SEQ ID NOs: 12481-12683, SEQ ID NOs: 12952-20446, SEQ ID NOs: 27942-28880, SEQ ID NOs: 29819-29983, SEQ ID NOs: 30149-30166 and SEQ ID NOs: 30185-30204.

In some embodiments, the nucleic acid sequence encoding a targeting peptide comprises an amino acid sequence of: PKMTLKI (SEQ ID NO: 320), LGKKTNS (SEQ ID NO: 325), LPKYKSS (SEQ ID NO: 396), GRGNSVL (SEQ ID NO: 465), RSPRVNA (SEQ ID NO: 466), IRNPRMA (SEQ ID NO: 467), ARRPNSE (SEQ ID NO: 480), IKMLNKP (SEQ ID NO: 484), or REVLQRI (SEQ ID NO: 506).

In some embodiments, the nucleic acid sequence encoding a targeting peptide comprises an amino acid sequence of: RKPRVHD (SEQ ID NO: 317), YADTNRR (SEQ ID NO: 321), TKSVRVV (SEQ ID NO: 327), TKSSMRP (SEQ ID NO: 336), RRHLAET (SEQ ID NO: 346), RRPPSMG (SEQ ID NO: 354), KDRKVPN (SEQ ID NO: 382), KVTNRHE (SEQ ID NO: 439), DMDLGMG (SEQ ID NO: 453), IEKPTYR (SEQ ID NO: 482), RGKMELY (SEQ ID NO: 505), SKDNHRM (SEQ ID NO: 511), DIHGANL (SEQ ID NO: 512), HSVGYLD (SEQ ID NO: 514), ASLADRP (SEQ ID NO: 515), SKNDHEY (SEQ ID NO: 517), or NLGAINK (SEQ ID NO: 522).

In some embodiments, the nucleic acid sequence encoding a targeting peptide comprises an amino acid sequence of: RSMKPNN (SEQ ID NO: 316), RKPRVHD (SEQ ID NO: 317), VRKMPDY (SEQ ID NO: 318), QKPIRIV (SEQ ID NO: 319), PKMTLKI (SEQ ID NO: 320), YADTNRR (SEQ ID NO: 321), RKQMNTT (SEQ ID NO: 322), ELYKLPT (SEQ ID NO: 323), GGQLRKP (SEQ ID NO: 324), LGKKTNS (SEQ ID NO: 325), NRQTVKG (SEQ ID NO: 326), TKSVRVV (SEQ ID NO: 327), GINVRPR (SEQ ID NO: 328), KKGSIGS (SEQ ID NO: 329), LRKNPNP (SEQ ID NO: 330), NSKTVVR (SEQ ID NO: 331), VRRTQLD (SEQ ID NO: 332), KKSTILA (SEQ ID NO: 333), RSKLGSG (SEQ ID NO: 334), DRRGHDR (SEQ ID NO: 335), TKSSMRP (SEQ ID NO: 336), NRITPNR (SEQ ID NO: 337), KIQNNKQ (SEQ ID NO: 338), KSRLTQP (SEQ ID NO: 339), SQKAGGR (SEQ ID NO: 340), ARKTPDY (SEQ ID NO: 341), TRKPVVI (SEQ ID NO: 342), NLKDKRT (SEQ ID NO: 343), KRDARMN (SEQ ID NO: 344), KGSMRQA (SEQ ID NO: 345), RRHLAET (SEQ ID NO: 346), VKTHRPV (SEQ ID NO: 347), or KRNNVAA (SEQ ID NO: 348).

In some embodiments, a targeting peptide does not comprise or consist of a sequence disclosed in WO2015/038958 or WO2017/100671, which are incorporated by reference herein in their entireties.

Target Proteins

Disclosed herein are targeting peptides capable of directing AAV to the central nervous system (CNS) via binding to at least one target protein. In some embodiments, an AAV capsid protein comprising a targeting peptide has increased transduction efficiency across the blood-brain barrier as compared to an AAV capsid protein lacking the targeting peptide. As used herein, the term "blood-brain barrier" or "BBB" refers to a network of blood vessels and tissue comprising closely spaced cells that regulate transport of substances between circulating blood from the brain and extracellular fluid in the CNS.

Target proteins that bind to targeting peptides described herein can include one or more of the following characteristics: expression in the CNS; capability of mediating transcytosis; capability of mediating endocytosis; capability of mediating intra-cellular trafficking; association with lipid rafts; and linkage to the cell surface, such as through a glycophosphatidylinositol (GPI) anchor. Characteristics of GPI-anchored proteins are described in, and incorporated by reference, from Zurzolo et al. (2016) *BBA*1858: 632-639; Saha et al. (2016) J. *Lipid Res.* 57: 159-175; Mayor et al. (2004) *Nat Rev Mol Cell Biol* 5, 110-120.

Target proteins, as described herein, can include, but are not limited to, members of the lymphocyte antigen-6 (Ly6)/urokinase-type plasminogen activator receptor (uPAR) protein family and GPI-anchored proteins. Notably, AAV2 has been shown to internalize in detergent-resistant GPI-anchored protein enriched endosomal compartment (GEEC), which is described in, and incorporated by reference, from: https://doi.org/10.1016/j.chom.2011.10.014. Ly6/uPAR proteins are cysteine-rich proteins characterized by a distinct disulfide bridge pattern that creates the three-finger Ly6/uPAR (LU) domain. As used herein, "Ly6/uPAR proteins" includes proteins that contain an LU domain regardless of whether they have been characterized as Ly6/uPAR proteins, and includes proteins that have been characterized as "Ly6-like" proteins, such as CD59. One of ordinary skill in the art would be able to recognize whether a protein sequence corresponds to a Ly6/uPAR protein, as used herein. For example, in some embodiments, a protein can be characterized as a Ly6/uPAR protein based on its level of homology to a protein that has been characterized as a Ly6/uPAR protein, or based on its level of homology to a protein that has been characterized as a Ly6-like protein. In other embodiments, a protein can be characterized as a Ly6/uPAR protein based on the presence of an LU domain.

The Ly6/uPAR protein family comprises at least 35 human and 61 mouse Ly6/uPAR proteins. Ly6/uPAR proteins are classified as glycophosphatidylinositol (GPI)-anchored proteins on the cell membrane or as secreted proteins based on their subcellular localization. The genes encoding Ly6/uPAR family proteins are conserved across different species and are clustered in syntenic regions on human chromosomes 8, 19, 6 and 11, and mouse Chromosomes 15, 7, 17, and 9, respectively. The Ly6/uPAR protein family is described further in Loughner et al. (2016) *Human Genomics* 10:10, which is incorporated by reference herein in its entirety.

Targeting peptides as described herein, in some embodiments, bind to a Ly6/uPAR protein. The Ly6/uPAR protein can be from any mammal, including humans and non-human primates. In some embodiments, the targeting peptide binds to a human Ly6 protein. In other embodiments, the targeting peptide binds to a non-human primate Ly6 protein. In other embodiments, the targeting peptide binds to a rodent Ly6/uPAR protein, such as a mouse Ly6/uPAR protein. Examples of Ly6/uPAR proteins include, but are not limited to, ACRV1, CD177, CD59A, CD59B, GML, GML2, GPIHBP1, LY6A, LY6A2, LY6C1, LY6C2, LY6D, LY6E, LY6F, LY6G, LY6G2, LY6G5B, LY6G5C, LY6G6C, LY6G6D, LY6G6E, LY6G6F, LY6G6G, LY6H, LY6I, LY6K, LY6L, LY6M, LYNX1, LYPD1, LYPD2, LYPD3, LYPD4, LYPD5, LYPD6, LYPD6B, LYPD8, LYPD9, LYPD10, LYPD11, PATE1, PATE2, PATE3, PATE4, PATE5, PATE6, PATE7, PATE8, PATE9, PATE10, PATE11, PATE12, PATE13, PATE14, PINLYP, PLAUR, PSCCA, SLURP1, SLURP2, SPACA4, and TEX101.

Human genes encoding Ly6/uPAR proteins include, but are not limited to, $ACRV_1$, $CD_{177}$, $CD_{59}$, GML, $GPIHBP_1$, LY6D, LY6E, LY6G5B, LY6G5C, LY6G6C, LY6G6D, LY6G6E, LY6G6F, LY6H, LY6K, LY6L, $LYNX_1$, $LYPD_1$, $LYPD_2$, $LYPD_3$, $LYPD_4$, $LYPD_5$, $LYPD_6$, LYPD6B, LYPD8, $PATE_1$, $PATE_2$, $PATE_3$, $PATE_4$, PINLYP, PLA UR, PSCA, $SLURP_1$, $SLURP_2$, $SPACA_4$, and $TEX_{101}$.

Mouse genes encoding Ly6/uPAR proteins include, but are not limited to, $Acrv_1$, $Cd_{177}$, $Cd_{59a}$, $Cd_{59b}$, Gml, $Gml_2$, $Gpihbp_1$, Ly6a, $Ly6a_2$, $Ly6c_1$, $Ly6c_2$, Ly6d, Ly6e, Ly6f, Ly6g, $Ly6g_2$, Ly6g5b, Ly6g5c, Ly6g6c, Ly6g6d, Ly6g6e, Ly6g6f, Ly6g6g, Ly6h, Ly6i, Ly6k, Ly6l, Ly6m, $Lynx_1$, $Lypd_1$, $Lypd_2$, $Lypd_3$, $Lypd_4$, $Lypd_5$, $Lypd_6$, $Lypd_{6b}$, $Lypd_8$, $Lypd_9$, $Lypd_{10}$, $Lypd_{11}$, $Pate_1$, $Pate_2$, $Pate_3$, $Pate_4$, $Pate_5$, $Pate_6$, $Pate_7$, $Pate_8$, $Pate_9$, $Pate_{10}$, $Pate_{11}$, $Pate_{12}$, $Pate_{13}$, $Pate_{14}$, Pinlyp, Plaur, Psca, $Slurp_1$, $Slurp_2$, $Spaca_4$, and $Tex_{101}$.

It should be appreciated that Ly6/uPAR proteins and their expression patterns are known in the art. Information regarding the sequences of Ly6/uPAR proteins and the tissues or cells in which they are expressed is available through public databases known to one of ordinary skill in the art.

In some embodiments, the targeting peptides described herein may bind to a target protein (e.g., Ly6/uPAR protein) with a dissociation constant (Kd) lower than 20 nM (e.g., 15 nM, 10 nM, 5 nm, 1 nm, or less than 1 nm). In some embodiments, the targeting peptides described herein may bind to a Ly6/uPAR protein (e.g., human Ly6) with a dissociation constant (Kd) lower than 20 nM (e.g., 15 nM, 10 nM, 5 nm, 1 nm, or less than 1 nm). The targeting peptide may specifically bind human Ly6. Alternatively, the targeting peptides may bind to Ly6 from different species (e.g., human, non-human primate, mouse, and/or rat). It should be appreciated that any method known in the art for measuring binding activity can be compatible with aspects of the disclosure.

Targeting peptides as described herein, in some embodiments, bind to a target protein expressed in the nervous system. In some embodiments, the targeting peptide binds to a target protein expressed in the CNS. In other embodiments, the targeting peptide binds to a target protein expressed in the PNS. In other embodiments, the targeting peptide binds to a target protein expressed in a hematopoietic lineage, such as an immune cell. Accordingly, in some embodiments, targeting peptides described herein mediate delivery of nucleic acids to the CNS or PNS. In other embodiments, targeting peptides described herein mediate delivery of nucleic acids to a hematopoietic lineage, such as an immune cell.

In some embodiments, targeting peptides described herein mediate delivery of nucleic acids. In other embodiments, targeting peptides described herein mediate delivery of other biologics, such as antibodies. In some embodiments, targeting peptides described herein mediate delivery of nucleic acids or other biologics, such as antibodies, across the blood brain barrier.

In some embodiments, the targeting peptide binds to a target protein involved in cell trafficking. In some embodiments, the targeting peptide binds to a target protein involved in endocytosis. In some embodiments, the targeting peptide binds to a target protein capable of being internalized or trafficked to certain organelles. In some embodiments, the targeting peptide binds to a target protein involved in trafficking to the Golgi. In some embodiments, the targeting peptide binds to a target protein involved in transcytosis in endothelial cells. In some embodiments, the targeting peptide binds to a target protein involved in transcytosis in epithelial cells.

In some embodiments, the targeting peptide binds to a target protein associated with a lipid raft. In some embodiments, the targeting peptide binds to a target protein comprising a GPI-anchor. In some embodiments, the targeting peptide binds to a target protein comprising a typical GPI-attachment signal, e.g., a polar segment that includes the GPI-attachment site followed by a hydrophobic segment located at the C-terminus of the protein.

In some embodiments, the targeting peptide binds to a CNS endothelium protein (e.g., CD59, Ly6E, GPIHBP1) and/or a cell surface protein (e.g., PRNP). In some embodiments, the targeting peptide binds to CD59. In some embodiments, the targeting peptide binds to Ly6E. In some embodiments, the targeting peptide binds to GPIHBP1. In some embodiments, the targeting peptide binds to PRNP.

In some embodiments, the targeting peptides bind to a GPI-anchored protein. In some embodiments, the genes encoding GPI-anchored proteins can include but are not limited to the genes listed in Table 20.

Targeting peptides as described herein, in some embodiments, bind to a target protein and one or more homologues of the target protein. In some embodiments, the target protein is selected from the group consisting of a human protein, a non-human primate protein (e.g., a marmoset protein), and a rodent protein (e.g., a mouse protein). In some embodiments, the homologous target protein is selected from the group consisting of a human protein, a non-human primate protein (e.g., a marmoset protein), and a rodent protein (e.g., a mouse protein).

In some embodiments, the targeting peptide binds to a target protein and at least one homologous target protein. For example, the targeting peptide binds a human target protein and a homolog of the target protein from a non-human primate (e.g., a marmoset). In some embodiments, the targeting peptide binds a human target protein and a homolog of the target protein from a rodent (e.g., a mouse). In some embodiments, the targeting peptide binds target protein from a non-human primate (e.g., a marmoset) and a homolog of the target protein from a rodent (e.g., a mouse).

In some embodiments, the targeting peptide binds to a target protein and at least two homologous target proteins. For example, the targeting peptide binds a human target protein, a homolog of the target protein from a non-human primate (e.g., marmoset), and a homolog of the target protein from a rodent (e.g., a mouse).

In some embodiments, the targeting peptide binds a human target protein and a homolog of the target protein from marmoset. In some embodiments, the targeting peptide binds a human target protein, a homolog of the target protein from marmoset, and a homolog of the target protein from mouse. In some embodiments, the targeting peptide binds a mouse target protein and a homolog of the target protein from marmoset.

Accordingly, aspects of the invention relate to recombinant AAV capsid proteins that bind to target proteins, such as Ly6/uPAR proteins, and that can be used to mediate transport of materials across the blood-brain barrier.

Methods for Selecting Targeting Peptides Based on Target Protein Binding

Methods provided herein, in some embodiments, are useful for identifying targeting peptides, or AAV capsid proteins harboring targeting peptides, that bind target proteins. In some embodiments, the target protein is ectopically expressed on cells. In some embodiments, the target protein is a recombinant protein. In some embodiments, the target protein is endogenously expressed in a cell. In some embodiments, methods provided herein are useful for identifying AAV capsids proteins that cross specific barriers (e.g., blood-brain barrier or gut epithelium). In some embodiments, methods provided herein are useful for identifying AAV9 capsids proteins.

Targeting peptides described herein can be identified by incubating a candidate targeting peptide (e.g., an AAV capsid protein containing a targeting peptide) with a Ly6/uPAR protein; and selecting the targeting peptide if it binds to the Ly6/uPAR protein. In some embodiments, the Ly6/uPAR protein is expressed in a cell, such as on the surface of the cell, and binding of the targeting peptide (e.g., an AAV capsid protein containing a targeting peptide) to the cell that expresses the target protein on the surface of the cell is detected. Such binding assays may be performed with purified target protein (e.g., a purified Ly6/uPAR protein), or with cells naturally expressing or transfected to express a target protein (e.g., a Ly6/uPAR protein). Binding assays may be performed in various formats, including in vitro, or in cell culture, and including high-throughput formats. In some embodiments, a targeting peptide (e.g., an AAV capsid protein containing a targeting peptide) described herein can be further evaluated by monitoring its ability to mediate transcytosis across the blood-brain barrier.

In some embodiments, the target protein (e.g., a Ly6/uPAR protein) is endogenously expressed in a cell. In some embodiments, a control cell does not express a Ly6/uPAR protein. For example, expression of a Ly6/uPAR protein in some embodiments is decreased in a control cell, such as by mutating or deleting expression of the gene encoding a Ly6/uPAR protein. In some embodiments, the level of binding between a targeting peptide and a target protein (e.g., a Ly6/uPAR protein) is compared between a cell that expresses a target protein (e.g., a Ly6/uPAR protein) and a cell that does not express a target protein (e.g., a Ly6/uPAR protein).

In some embodiments, the targeting peptide disclosed herein specifically binds to a target protein, such as a human Ly6/uPAR protein. Methods to determine such specific binding are well known in the art. A targeting peptide is said to exhibit "specific binding" or to "specifically bind to a target protein" if it reacts or associates more frequently, more rapidly, with greater duration and/or with greater affinity with a particular target protein than it does with alternative target proteins. A targeting peptide that specifically binds to a first target protein may or may not specifically or preferentially bind to a second target protein.

As such, "specific binding" or "preferential binding" does not necessarily require (although it can include) exclusive binding. Generally, but not necessarily, reference to binding means preferential binding.

An AAV capsid protein is said to exhibit "specific binding" or to "specifically bind" to a protein if it reacts or associates more frequently, more rapidly, with greater duration and/or with greater affinity with the protein than it does with alternative target proteins. An AAV capsid protein that specifically binds to a protein may or may not specifically or preferentially bind to the protein. In some embodiments, the protein is a protein of the Ly6/uPAR protein family attached to the surface of a cell. In some embodiments, the protein is a GPI-anchored protein attached to the surface of a cell. In some embodiments, the protein is i) a protein that exhibits luminal surface exposure on brain endothelium; ii) a protein that is localized within lipid micro-domains; and/or iii) a protein that exhibits recycling/intracellular trafficking capabilities. In some embodiments, specific binding is determined by comparison to a control. For example, a control may involve contacting an AAV capsid protein with a cell that does not express the protein or contacting an AAV capsid protein with a cell that expresses a different protein.

For example, methods disclosed herein can comprise providing an AAV capsid protein, incubating the AAV capsid protein with a cell that recombinantly expresses a target protein attached to the surface of the cell, and selecting the AAV capsid protein if it specifically binds to the target protein attached to the surface of the cell.

In some embodiments, methods disclosed herein can comprise providing an AAV capsid protein, incubating the AAV capsid protein with a target protein that was purified from cells expressing the target protein, and selecting the AAV capsid protein if it specifically binds to the target protein.

In some embodiments, methods comprise providing an AAV capsid protein, incubating the AAV capsid protein with a cell that recombinantly expresses a Ly6/uPAR protein attached to the surface of the cell, and selecting the AAV capsid protein if it specifically binds to the Ly6/uPAR protein attached to the surface of the cell.

In some embodiments, methods comprise providing an AAV capsid protein, incubating the AAV capsid protein with a Ly6/uPAR protein, and selecting the AAV capsid protein if it specifically binds to the Ly6/uPAR protein.

In some embodiments, methods comprise screening for an AAV capsid protein that can bind to a target protein, comprising providing a library of AAV capsid proteins, incubating the library of AAV capsid proteins with a cell that recombinantly expresses a target protein attached to the surface of the cell, isolating an AAV capsid protein that binds to the cells that recombinantly express the target protein on the cell surface, and identifying the sequence of the isolated AAV capsid protein.

In some embodiments, methods comprise screening for an AAV capsid protein that can bind to a target protein, comprising providing a library of AAV capsid proteins, incubating the library of AAV capsid proteins with a target protein (e.g., a recombinant target protein or a target protein purified from cells expressing the target protein), isolating an AAV capsid protein that binds to the target protein, and identifying the sequence of the isolated AAV capsid protein.

The sequence of the isolated AAV capsid proteins may be identified using any sequencing methods known in the art. In some embodiments, AAV capsid proteins are sequenced using short read sequencing technology. In some embodiments, AAV capsid proteins are sequenced using long read sequencing technology. In some embodiments, AAV capsid proteins are sequenced using next-generation sequencing (NGS) technology or whole genome sequencing (WGS) technology.

Methods provided herein may be performed using any type of cell. Examples of cells include, but are not limited to, mammalian cells, rodent cells, yeast cells, and bacterial cells. Examples of mammalian cells include, but are not limited to, CHO (Chinese Hamster Ovary), VERO, HeLa, CVI, COS, COS-7, BHK (baby hamster kidney), MDCK, CI 27, PC 12, HEK-293, PER C6, NSO, WI38, R1610, BALBC/3T3, HAK, SP2/0, P3x63-Ag3.653, BFA-1c1BPT, RAJI, and 293 cells.

Methods provided herein may be performed using purified endogenous proteins, tagged AviTag, C-tag, Calmodulin-tag, E-tag, FLAG, HA, poly-HIS, MYC, NE, Rho1D4, S-tag, SBP, Softag, Spot-tag, T7-tag, TC, Ty, V5, VSV, Xpress, Isopeptag, SpyTag, SnoopTag, DogTag, SdyTag, BCCP, GST, GFP, Halo, SNAP, CLIP, Maltose binding protein (MBP), Nus-tag, Thioredoxin-tag, Fc-tag, CRDSAT, SUMO-tag, B2M-tag. The recombinant proteins can be purified from any cell type. Examples of cells include, but are not limited to, mammalian cells, rodent cells, yeast cells, and bacterial cells. Examples of mammalian cells include, but are not limited to, CHO (Chinese Hamster Ovary), VERO, HeLa, CVI, COS, COS-7, BHK (baby hamster kidney), MDCK, CI 27, PC 12, HEK-293, PER C6, NSO, WI38, R1610, BALBC/3T3, HAK, SP2/0, P3x63-Ag3.653, BFA-1c1BPT, RAJI, and 293 cells Methods of Use Methods provided herein, in some embodiments, are useful for delivering a nucleic acid (or another biologic, such as an antibody) to a target environment (e.g., the heart, the nervous system, or a combination thereof) of a subject in need. In some embodiments, methods for delivering a nucleic acid (or another biologic, such as an antibody) to a target environment comprise delivering the nucleic acid (or another biologic, such as an antibody) to the heart, the nervous system, or a combination thereof. In some embodiments, methods for delivering a nucleic acid (or another biologic, such as an antibody) to a target environment comprise delivering the nucleic acid (or another biologic, such as an antibody) to neurons, astrocytes, cardiomyocytes, or a combination thereof. In some embodiments, methods for delivering a nucleic acid (or another biologic, such as an antibody) to a target environment comprise delivering the nucleic acid (or another biologic, such as an antibody) to a hematopoietic lineage, such as an immune cell. Methods of use of AAV vectors are described further in U.S. Pat. No.

9,585,971 and US 2017/0166926, which are incorporated by reference herein in their entireties.

In some embodiments, methods for delivering a nucleic acid to a target environment of a subject in need comprise providing a composition comprising an AAV as described herein, and administering the composition to the subject. In some embodiments, methods for delivering a nucleic acid to a target environment of a subject in need thereof comprise providing a composition comprising an AAV comprising (i) a capsid protein that comprises an amino acid sequence that comprises at least 4 contiguous amino acids of a sequence provided herein, and (ii) a nucleic acid (or another biologic, such as an antibody) to be delivered to the target environment of the subject, and administering the composition to the subject.

Methods provided herein, in some embodiments, are useful for treating a disorder or defect in a subject. In some embodiments, the methods as described herein comprise delivering a protein, RNA, or DNA to a target environment of the subject. In some embodiments, the methods as described herein comprise administering an adeno-associated virus (AAV) vector to a target environment of the subject. In some embodiments, the AAV vector comprises a nucleic acid molecule that encodes a therapeutic protein or therapeutic RNA effective in treating the disorder or defect. In some embodiments, the AAV vector comprises a capsid protein comprising at least 4 contiguous amino acids from a sequence listed in Table 4, 5, 6, 7, 8, 9, 10, 11, 12, 13, 14, 15, 16, 17, 18 or 19.

In some embodiments, the protein, RNA, or DNA can be a Ly6/uPAR protein or gene. In one embodiment, the Ly6/uPAR is LY6. In some embodiments, the LY6/uPAR is LY6A. In some embodiments, the LY6/uPAR is LY6C1. In some embodiments, the LY6/uPAR can be any protein that is suitable to be delivered to a target environment. In some embodiments, the LY6/uPAR receptor is a murine receptor. In some embodiments, the AAV targets the Ly6/uPAR protein. In some embodiments, the AAV targets any protein that are characterized as "Ly6-like" proteins.

In some embodiments, the protein, RNA, or DNA is delivered to the subject via intravenous administration or systemic administration. In some embodiments, the protein, RNA, or DNA is delivered in trans. In some embodiments, the protein, RNA, or DNA is delivered to the subject via a nanoparticle. In some embodiments, the RNA is delivered to the subject via a viral vector. In some embodiments, the RNA is delivered to the subject via any carriers suitable for delivering nucleic acid materials. In some embodiments, the protein is a purified protein. In some embodiments, the Ly6/uPAR gene is delivered to the subject via a viral vector.

In some embodiments, the protein or RNA is delivered prior to the administration of the AAV vector. The protein or RNA (e.g. Ly6a or Ly6c1), or an ectopic receptor can be expressed in the target environment transiently. In some embodiments, the AAV vector can be administered to the subjects 12 hours, 1 day, 2 days, 3 days, 4 days, 5 days, 6 days, 7 days, 8 days, 9 days, 10 days, inclusive of all ranges and subranges therebetween, after the protein or RNA is delivered to the target environment. In some embodiments, the AAV vector can then specifically interact with the ectopic receptor (e.g. Ly6a or Ly6c1) during the timeframe of expression of the delivered ectopic receptor. "Transiently," "transient expression," or "transient gene expression" as described herein refers to the temporary expression of proteins or genes that are expressed for a short time after a protein or a nucleic acid (e.g., plasmid DNA encoding an expression cassette), has been introduced into the target environment.

In some embodiments, the protein or RNA can be delivered to the target environment simultaneously with the AAV vector. In some embodiments, the protein or RNA can be delivered to the target environment with the AAV vector in any order or timeframe that is suitable for treating a disorder or defect in the subject as described herein. For example, the AAV vector can be administered a few minutes after the delivery of the protein or RNA.

Any nucleic acid may be delivered to a target environment of a subject according to methods described herein. In some embodiments, a nucleic acid to be delivered to a target environment of a subject comprises one or more sequences that would be of some use of benefit to the subject. In some embodiments, the nucleic acid is delivered to dorsal root ganglia, visceral organs, astrocytes, neurons, or a combination thereof of the subject.

In a non-limiting example, the nucleic acid or nucleic acid molecule to be delivered can comprise one or more of (a) a nucleic acid sequence encoding a trophic factor, a growth factor, or a soluble protein; (b) a cDNA that restores protein function to humans or animals harboring a genetic mutation (s) in that gene; (c) a cDNA that encodes a protein that can be used to control or alter the activity or state of a cell; (d) a cDNA that encodes a protein or a nucleic acid used for assessing the state of a cell; (e) a cDNA and/or associated guide RNA for performing genomic engineering; (f) a sequence for genome editing via homologous recombination; (g) a DNA sequence encoding a therapeutic RNA; (h) a shRNA or an artificial miRNA delivery system; and (i) a DNA sequence that influences the splicing of an endogenous gene.

Any subject in need may be administered a composition comprising an AAV according to methods described herein. In some embodiments, a subject in need or a subject having a disorder or defect is a subject suffering from or at a risk to develop one or more diseases. In some embodiments, the subject in need is a subject suffering from or at a risk to develop one or more of chronic pain, cardiac failure, cardiac arrhythmias, Friedreich's ataxia, Huntington's disease (HD), Alzheimer's disease (AD), Parkinson's disease (PD), Amyotrophic lateral sclerosis (ALS), spinal muscular atrophy types I and II (SMA I and II), Friedreich's Ataxia (FA), Spinocerebellar ataxia, lysosomal storage disorders that involve cells within the CNS.

Any suitable method may be used for administering a composition comprising an AAV described herein. In some embodiments, the composition comprising the AAV is administered to the subject via intravenous administration. In some embodiments, the composition comprising the AAV is administered to the subject via or systemic administration.

Pharmaceutical Compositions

Aspects of the present disclosure provide, in some embodiments, a pharmaceutical composition comprising an AAV vector as described herein and a pharmaceutically acceptable carrier. Suitable carriers may be readily selected by one of skill in the art in view of the indication for which the AAV vector is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure. Pharmaceutical compositions comprising AAV vectors are described further in U.S.

Pat. No. 9,585,971 and US 2017/0166926, which are incorporated by reference herein in their entireties.

In some embodiments, the pharmaceutical composition comprising an AAV vector comprises other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Methods described herein comprise administering AAV vector in sufficient amounts to transfect the cells of a desired tissue (e.g., heart, brain) and to provide sufficient levels of gene transfer and expression without undue adverse effects. Examples of pharmaceutically acceptable routes of administration include, but are not limited to, direct delivery to the selected organ, oral, inhalation, intraocular, intravenous, intramuscular, subcutaneous, intradermal, intratumoral, and other parental routes of administration. Routes of administration may be combined, if desired.

The dose of AAV required to achieve a particular "therapeutic effect," e.g., the units of dose in genome copies/per kilogram of body weight (GC/kg), will vary based on several factors including, but not limited to: the route of AAV administration, the level of gene or RNA expression required to achieve a therapeutic effect, the specific disease or disorder being treated, and the stability of the gene or RNA product. One of skill in the art can readily determine a AAV dose range to treat a patient having a particular disease or disorder based on the aforementioned factors, as well as other factors.

An effective amount of AAV vector is an amount sufficient to infect an animal or target a desired tissue. The effective amount will depend primarily on factors such as the species, age, weight, health of the subject, and the tissue to be targeted, and may thus vary among animal and tissue. For example, an effective amount of AAV is generally in the range of from about 1 ml to about 100 ml of solution containing from about $10^9$ to $10^{16}$ genome copies. In some cases, a dosage between about $10^{11}$ to $10^{13}$ AAV genome copies is appropriate. In some embodiments, an effective amount is produced by multiple doses of AAV.

In some embodiments, a dose of AAV is administered to a subject no more than once per calendar day (e.g., a 24-hour period). In some embodiments, a dose of AAV is administered to a subject no more than once per 2, 3, 4, 5, 6, or 7 calendar days. In some embodiments, a dose of AAV is administered to a subject no more than once per calendar week (e.g., 7 calendar days). In some embodiments, a dose of AAV is administered to a subject no more than bi-weekly (e.g., once in a two calendar week period). In some embodiments, a dose of AAV is administered to a subject no more than once per calendar month (e.g., once in 30 calendar days). In some embodiments, a dose of AAV is administered to a subject no more than once per six calendar months. In some embodiments, a dose of AAV is administered to a subject no more than once per calendar year (e.g., 365 days or 366 days in a leap year). In some embodiments, a dose of rAAV is administered to a subject no more than once per two calendar years (e.g., 730 days or 731 days in a leap year). In some embodiments, a dose of AAV is administered to a subject no more than once per three calendar years (e.g., 1095 days or 1096 days in a leap year).

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The AAV vector compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable"

refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the AAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the AAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the AAV vector may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

EXAMPLES

The number of diseases that are potentially treatable by gene therapy is rapidly expanding. AAV vectors are proving to be safe, versatile vehicles for in vivo gene therapy applications (1-3). However, delivery challenges impede the application of gene therapy, particularly in the context of the brain, which is protected by the blood-brain barrier (BBB). To improve gene delivery across the central nervous system (CNS), AAV capsids have been engineered using in vivo selection and directed evolution (4-11). Previously engineered AAV9 variants include AAV-PHP.B (5) and its further evolved, more efficient variant, AAV-PHP.eB (4), that cross the adult BBB and enable efficient gene transfer to the mouse CNS. Since then, AAV-PHP.B and AAV-PHP.eB have been applied across a wide range of neuroscience experiments in mice (4, 12, 13), including genetic deficit correction (14, 15) and neurological disease modeling (16).

One critical question has been whether AAV-PHP.B and AAV-PHP.eB can facilitate efficient CNS gene transfer in other species. The enhanced CNS tropism of AAV-PHP.B and AAV-PHP.eB appears to extend to rats (17, 18), whereas studies testing AAV-PHP.B or related capsids in nonhuman primates (NHPs) have yielded differing outcomes (19-21). Surprisingly, the enhanced CNS tropism of AAV-PHP.B (5, 12, 15-18, 22, 23) was starkly absent in BALB/cJ mice (19). These findings indicate that the ability of AAV-PHP.B to cross the BBB is affected by genetic factors that vary by species and mouse line. Studies described herein leverage this strain-dependence to identify LY6A as the cellular receptor responsible for the enhanced CNS tropism exhibited by the AAV-PHP.B capsid family. It was demonstrated that the LY6A-mediated mechanism of transduction is independent of known AAV9 receptors and is a unique means for AAV-PHP.B capsids to cross the mouse BBB. This has widespread implications for guiding the selection of disease models in studies utilizing AAV-PHP.B capsids, as well as ongoing efforts to rationally engineer AAVs that cross the BBB in other species.

Example 1: Materials and Methods

Mouse Strain Permutation Analysis

Access to whole-genome sequencing data for 36 commercially available mouse lines made it possible to estimate the number of lines necessary to produce an adequately short list of candidate variants. Starting from the known permissive C57BL/6J non-permissive BALB/cJ strains, the Hail software library was used to simulate permissivity phenotypes among other mouse lines and compute the number of candidate variants in both the high and high-and-medium predicted functional impact classes. First, a permissivity frequency was sampled from a Beta(2, 2) distribution based on the two known mouse phenotypes. Second, one or more additional mouse lines were sampled from 26 commercially available lines (Table 1). Third, phenotypes for these mice were simulated using the generated permissivity frequency. Finally, the number of variants with perfect allelic segregation between simulated permissive and non-permissive lines was calculated and recorded. This simulation model ran for 500 iterations for 3 mice up to 12 mice, providing a distribution over the number of candidate variants at each mouse sample size, and enabling an informed decision about how many mouse lines to order and test in parallel.

TABLE 1

Permissive or nonpermissive AAV-PHP.eB CNS transduction phenotypes for inbred mouse lines with available whole genome sequencing (WGS) data. The lines highlighted in bolded text were used in the analysis presented in FIG. 2A.

| Strain | Enhanced CNS tropism | References |
|---|---|---|
| **AKR/J** | Present | This study |
| **BTBR/T+/Itpr3tf/J** | Present | Predicted |
| **C57BL/6J** | Present, previously reported | (2, 6-8) |
| **C57BL/6N** | Present, previously reported | (9) |
| **C57BL/10J** | Present | Predicted |
| **C57BR/cdJ** | Present | Predicted |
| **C57L/J** | Present | This study |
| C58/J | Present | Predicted |
| **DBA/1J** | Present | Predicted |
| **DBA/2J** | Present | This study |
| **FVB/NJ** | Present | This study |
| I/LnJ | Present | Predicted |
| KK/HiJ | Present | Predicted |
| **LP/J** | Present | This study |
| **NZW/LacJ** | Present | Predicted |
| RF/J | Present | Predicted |
| **MOLF/EiJ** | Present | This study |
| 129P2/OlaHsd | Present | Predicted |
| **129S1/SvImJ** | Present | Predicted |
| 129S5SvEvBrd | Present | Predicted |
| **A/J** | Absent | Predicted |
| **BALB/cJ** | Absent, previously reported | (10); this study |
| BUB/BnJ | Absent | Predicted |
| **CAST/EiJ** | Absent | This study |
| **CBA/J** | Absent | This study |
| C3H/HeH | Absent | Predicted |
| **C3H/HeJ** | Absent | Predicted |
| **LEWES/EiJ** | Absent | Predicted |

TABLE 1-continued

Permissive or nonpermissive AAV-PHP.eB CNS transduction phenotypes for inbred mouse lines with available whole genome sequencing (WGS) data. The lines highlighted in bolded text were used in the analysis presented in FIG. 2A.

| Strain | Enhanced CNS tropism | References |
|---|---|---|
| **NOD/ShiLtJ** | Absent | This study |
| **NZB/B1NJ** | Absent | This study |
| **NZO/HlLtJ** | Absent | Predicted |
| **PWK/PhJ** | Absent | This study |
| SEA/GnJ | Absent | Predicted |
| **SPRET/EiJ** | Absent | Predicted |
| SEA/GnJ | Absent | Predicted |
| ST/bJ | Absent | Predicted |
| **WSB/EiJ** | Absent | Predicted |
| ZALENDE/EiJ | Absent | Predicted |

Plasmids and Primers

The AAV-PHP.eB Rep-Cap trans plasmid was generated by gene synthesis (GenScript). AAV9, AAV-PHP.B, AAV-PHP.B2, and AAV-PHP.B3 were generated by replacing the AAV-PHP.eB variant region with that of AAV9, AAV-PHP.B, B2, or B3 using isothermal HiFi DNA Assembly (NEB). AAV-CAG-NLS-GFP and AAV-CAG-NLS-mScarlet vectors were synthesized using the N-terminal SV40 NLS sequence present in the Addgene plasmid #99130 as a gBlock (IDT) and GFP was subcloned in place of mScarlet to produce the NLS-GFP cassette. Ly6a and Ly6c1 (splice variant 1) cDNAs were synthesized as gBlocks (IDT). Reporter and Ly6 expression vectors were cloned into an AAV-CAG-WPRE-hGH pA backbone obtained from Addgene (#99122). The CMV-SaCAS9 vector (AAV-CMV::NLS-SaCas9-NLS-3xHA-bGHpA; U6::BsaI-sgRNA) was obtained from Dr. Feng Zhang through Addgene (#61591). sgRNAs specifically targeting Ly6a or Ly6c1 were cloned after the U6 promoter using a single bridge oligo for each reaction as recommended (HiFi DNA Asssembly, NEB). The Broad GPP sgRNA tool for SaCAS9 was used to identify suitable SaCAS9 target sites (1).

The following primers were used for Ly6a sgRNA cloning:

(SEQ ID NO: 1)
5'-CTTGTGGAAAGGACGAAACACCGAATTACCTGCCCCTACCCTGAGT
TTTAGTACTCTGGAAACAG (SEQ ID NO: 2)
5'-CTTGTGGAAAGGACGAAACACCGCTTTCAATATTAGGAGGGCAGGT
TTTAGTACTCTGGAAACAG (SEQ ID NO: 3)
5'-CTTGTGGAAAGGACGAAACACCGAATATTGAAAGTATGGAGATCGT
TTTAGTACTCTGGAAACAG

The following primers were used for Ly6c1 sgRNAs cloning:

(SEQ ID NO: 4)
5'-CTTGTGGAAAGGACGAAACACCGACTGCAGTGCTACGAGTGCTAGT
TTTAGTACTCTGGAAACAG (SEQ ID NO: 5)
5'-CTTGTGGAAAGGACGAAACACCGCAGTTACCTGCCGCGCCTCTGGT
TTTAGTACTCTGGAAACAG (SEQ ID NO: 6)
5'-CTTGTGGAAAGGACGAAACACCGGATTCTGCATTGCTCAAAACAGT
TTTAGTACTCTGGAAACAG qPCR primers used for biodistribution and in vitro binding:

GFP:
(SEQ ID NO: 7)
5'-TACCCCGACCACATGAAGCAG (SEQ ID NO: 8)
5'-CTTGTAGTTGCCGTCGTCCTTG

Mouse glucagon:
(SEQ ID NO: 9)
5'-AAGGGACCTTTACCAGTGATGTG (SEQ ID NO: 10)
5'-ACTTACTCTCGCCTTCCTCGG Human glucagon:
(SEQ ID NO: 11)
5'-ATGCTGAAGGGACCTTTACCAG (SEQ ID NO: 12)
5'-ACTTACTCTCGCCTTCCTCGG CHO glucagon:
(SEQ ID NO: 13)
5'-ATGCTGAAGGGACCTTTACCAG (SEQ ID NO: 14)
5'-CTCGCCTTCCTCTGCCTTT CRISPR/SaCas9 KO Experiments AAV-PHP.eB vectors with sgRNA sequences target Ly6a and Ly6c1 were generated and purified to knockout respective gene in C57BL/6 mouse primary brain microvascular endothelial cells (CellBiologics, Cat.# C57-6023). AAV vectors ($1\times10^6$ vg per cell) were used to transduce cells every 3 days for 3 times to achieve higher knockout efficiency. Cells were passaged as necessary.

Cell Lines and Primary Cultures

HEK293T/17 (CRL-11268), Pro5 (CRL-1781), Lec2 (CRL-1736), and Lec8 (CRL-1737) were obtained from ATCC. BMVEC cells were obtained from Cell Biologics (C57-6023) and cultured as directed by the manufacturer.

Virus Production and Purification

Recombinant AAVs were generated by triple transfection of HEK293T cells (ATCC CRL-11268) using polyethylenimine (PEI) and purified by ultracentrifugation over iodixanol gradients as previously described (2).

Western Blotting and Virus Overlay Assays

The virus overlay assay was performed as previously reported (3) with some modifications. Briefly, protein lysates were separated on Bolt 4-12% Bis-Tris Plus gels and transferred onto nitrocellulose membranes. After incubation with AAV9 or PHP.eB at 5e11 vg/ml, the membranes were fixed with 4% PFA at room temperature for 20 minutes to cross-link the interaction between capsid and its target protein followed by 2M HCl treatment at 37 °C for 7 minutes to expose the internal capsid epitope for detection. The blots were then rinsed and incubated with anti-AAV VP1/VP2/VP3 (1:20; American research products, Inc. cat#03-65158) followed by incubation with a horseradish peroxidase (HRP)-conjugated secondary antibody at 1:5000. The detection of binding was by SuperSignal West Femo Maximum Sensitivity Substrate under a Bio-Rad ChemiDoc TM MP system #1708280.

Animals

All procedures were performed as approved by the Broad Institute IACUC or Massachusetts General Hospital IACUC (AAVR experiments). AKR/J (000648), BALB/cJ (000651), CBA/J (000656), CAST/EiJ (000928), C57Bl/6J (000664), C57BL/J (000668), DBA/2J (000671), FVB/NJ (001800), LP/J (000676), MOLF/EiJ (000550), NOD/ShiLtJ (001976), NZB/B1NJ (000684), and PWK/PhJ (003715) were obtained from The Jackson Laboratory (JAX). AAVR mice were a generous gift from Dr. J.E. Carette (Stanford) to Dr. Balazs. Recombinant AAV vectors were administered intravenously via the retro-orbital sinus in young adult male or female mice. Mice were randomly assigned to groups based on predetermined sample sizes. No mice were excluded from the analyses. Experimenters were not blinded to sample groups.

Tissue Processing, Immunohistochemistry and Imaging

Mice were anesthetized with Euthasol (Broad) or ketamine (MGH) and transcardially perfused with phosphate buffered saline (PBS) at room temperature followed by 4% paraformaldehyde (PFA) in PBS. Tissues were post-fixed overnight in 4% PFA in PBS and sectioned by vibratome. IHC was performed on floating sections with antibodies diluted in PBS containing 10% donkey serum, 0.1% Triton X-100, and 0.05% sodium azide. Primary antibodies were incubated at room temperature overnight. The sections were then washed and stained with secondary (Alexa-conjugated antibodies, 1:1000) for 4 hours or overnight. Primary antibodies used were mouse anti-AAV capsid (1:20; American Research Products, 03-65158, clone B1), LY6A (1:250; BD Bioscience, 553333 or ThermoFisher, 701919), LY6C1 (1:250; Millipore-Sigmam MABN668), Glut1 (Millipore Sigma, 07-1401). To expose the internal B1 Capsid epitope in intact capsids, tissue sections or cells on coverslips were treated for 15 or 7 minutes, respectively, with 2M HCl at 37 °C. The treated samples were then washed extensively prior to addition of the primary antibody.

In Vivo Vector and Capsid Biodistribution 5- to 6-week-old C57Bl/6J mice, BALB/cJ mice AAVR WT or AAVR KO mice (FVB/NJ background) were injected intravenously with $10^{11}$ vg of AAV vector packaged into the indicated capsid. One or two hours after injection, the mice were perfused with PBS and tissues were collected and frozen at −80 °C. Samples were processed for AAV genome biodistribution analysis and normalized to the number of copies of mouse genomes using qPCR for the GFP element and mouse glucagon by qPCR as previously described (2). To visualize the capsid distribution, mice were perfused with 4% PFA after dosing with AAV vector and brain were section into 100 micrometer and labeled with indicated antibodies.

Microscopy

Images were taken on an Axio Imager.Z2 Basis Zeiss 880 laser scanning confocal microscope fitted with the following objectives: PApo 10×/0.45 M27, Plan-Apochromat 20×/0.8 M27, or Plan-APO 40×/1.4 oil DIC (UV) VIS-IR. All images compared within an experiment were acquired and processed under identical conditions.

In Vitro Binding Assays

Ly6 family members (0.5 μg/well) were transfected into HEK293T cells ($3\times10^5$/well) using PEI or into CHO cells ($1.5\times10^5$/well) with lipofectamine 3000 reagent (ThermoFisher, L3000001) in 24-well plates. 48 hours later, the cells were chilled to 4 °C and the media was exchanged with fresh cold media containing the indicated recombinant AAV ($10^5$ copies per cell). One hour later, cells were washed with cold PBS for 3 times, then fixed with 4% PFA for IHC or lysed for genomic DNA extraction and qPCR analyses.

For BMVECs, $2\times10^4$ cells/well were seeded in 12 well plate the day before exposure to virus. The assay was performed as above except AAV vectors were added at $10^6$ copies/cell.

HEK293T/17 cells were seeded at $2\times10^7$ per T75 flask 12-24 hours prior to being transfected with 20 μs of cDNA encoding eGFP, Ly6a, or Ly6c1. At 24-48 hours post transfection, the cells were incubated with an AAV9 K449R library (7-mer insertion between amino acids 588 and 589) at $10^{11}$ vg/T75 at 4 °C for 2 hours. Afterwards, the media was exchanged with PBS for 3 times in order to wash away unbound viruses. The viruses that remained bound to the cells were extracted with TRIzol (Invitrogen) or with whole genomic DNA isolation reagents (DNeasy, Qiagen) in order to isolate their viral genomes. The viral genomes were then prepared for next generation sequencing (NGS) to quantify the enrichment of peptides that conferred increased capsid ability to bind cells expressing the target protein.

Luciferase Transduction Assay

Figure 3A:
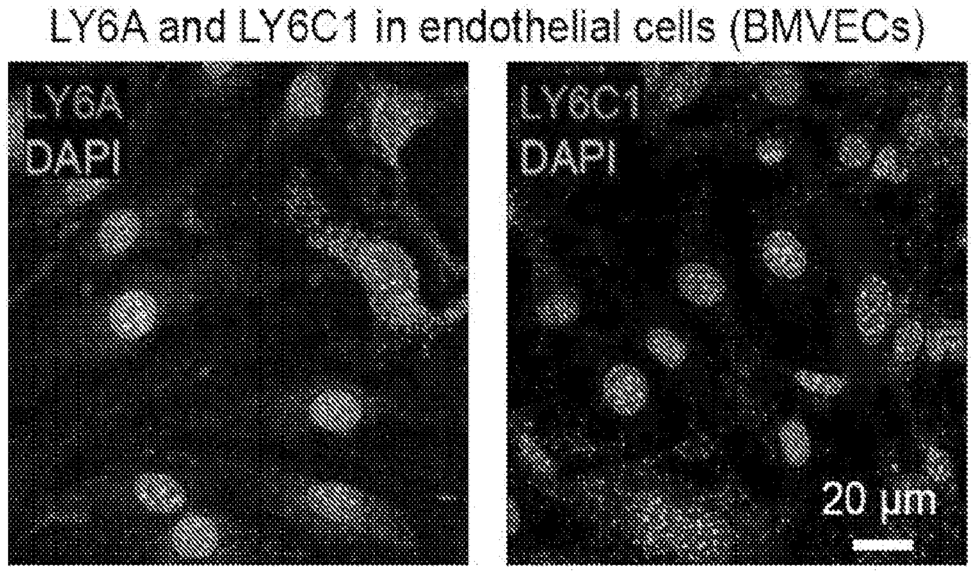
FIG. 3A shows images of LY6A (left) and LY6C1 (right) immunostaining with nuclei (dapi) in BMVECs.
Figure 3B:
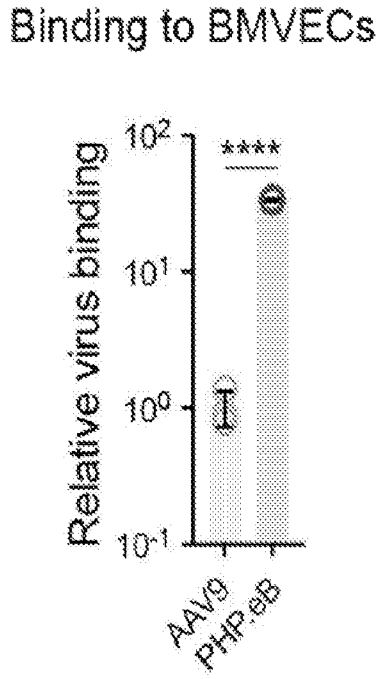
FIG. 3B shows a graph of AAV9 and AAV-PHP.eB binding of BMVECs. Binding was assessed by qPCR of the viral genome.
Figure 3C:
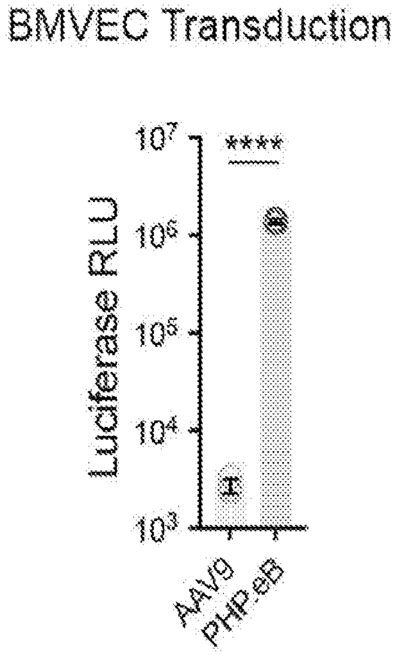
FIG. 3C shows a graph of AAV9 and AAV-PHP.eB transduction of BMVECs. Transduction was assessed by measuring Luciferase luminescence in relative light units (RLU).
Figure 3D:
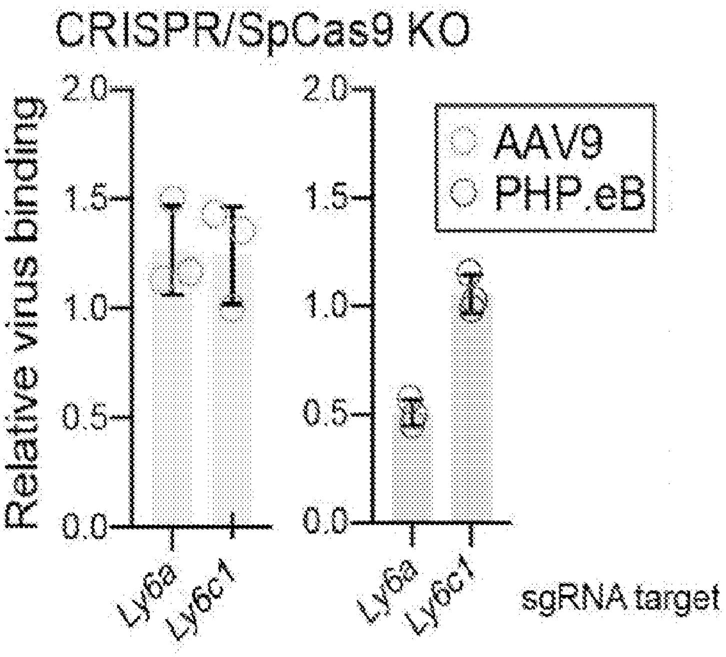
FIG. 3D shows a graph of binding (2-way ANOVA, Dunnett's multiple comparison test) by the indicated virus in cells treated with a vector containing an sgRNA to disrupt Ly6a or Ly6c1 or no sgRNA. Each data point represents cells that received a different sgRNA.
Figure 3E:
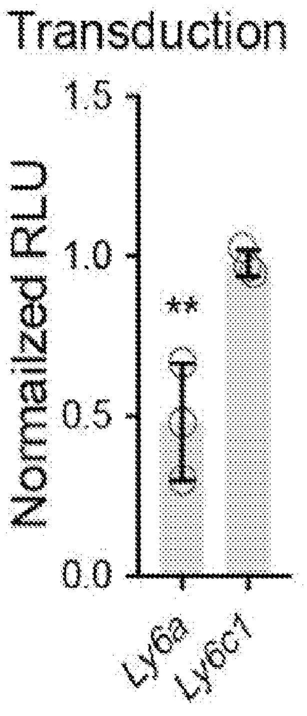
FIG. 3E shows a graph of transduction (1-way ANOVA, Sidak's post test) by the indicated virus in cells treated with a vector containing an sgRNA to disrupt Ly6a or Ly6c1 or no sgRNA. Each data point represents cells that received a different sgRNA.

Ly6 family members (0.1 μg/well) were transfected into the indicated cells (HEK293/17: $4\times10^5$/well; CHO: $2.5\times10^4$/well, BMVECs: $5\times10^3$/well) in 96-well plates (PerkinElmer, 6005680) in triplicate. 48 hours later, cells were transduced with AAV-CAG-GFP-2A-Luciferase-WPRE packaged into AAV9 or AAV-PHP.eB. Luciferase assays were performed with Britelite plus Reporter Gene Assay System (PerkinElmer, 6066766). Luciferase activity was reported as relative light units (RLU) as raw data or normalized to non-transfected control wells transduced with AAV9, or a control transduced without a sgRNA (FIG. 3E).

Statistical Analysis and Experimental Design

Figure 6:
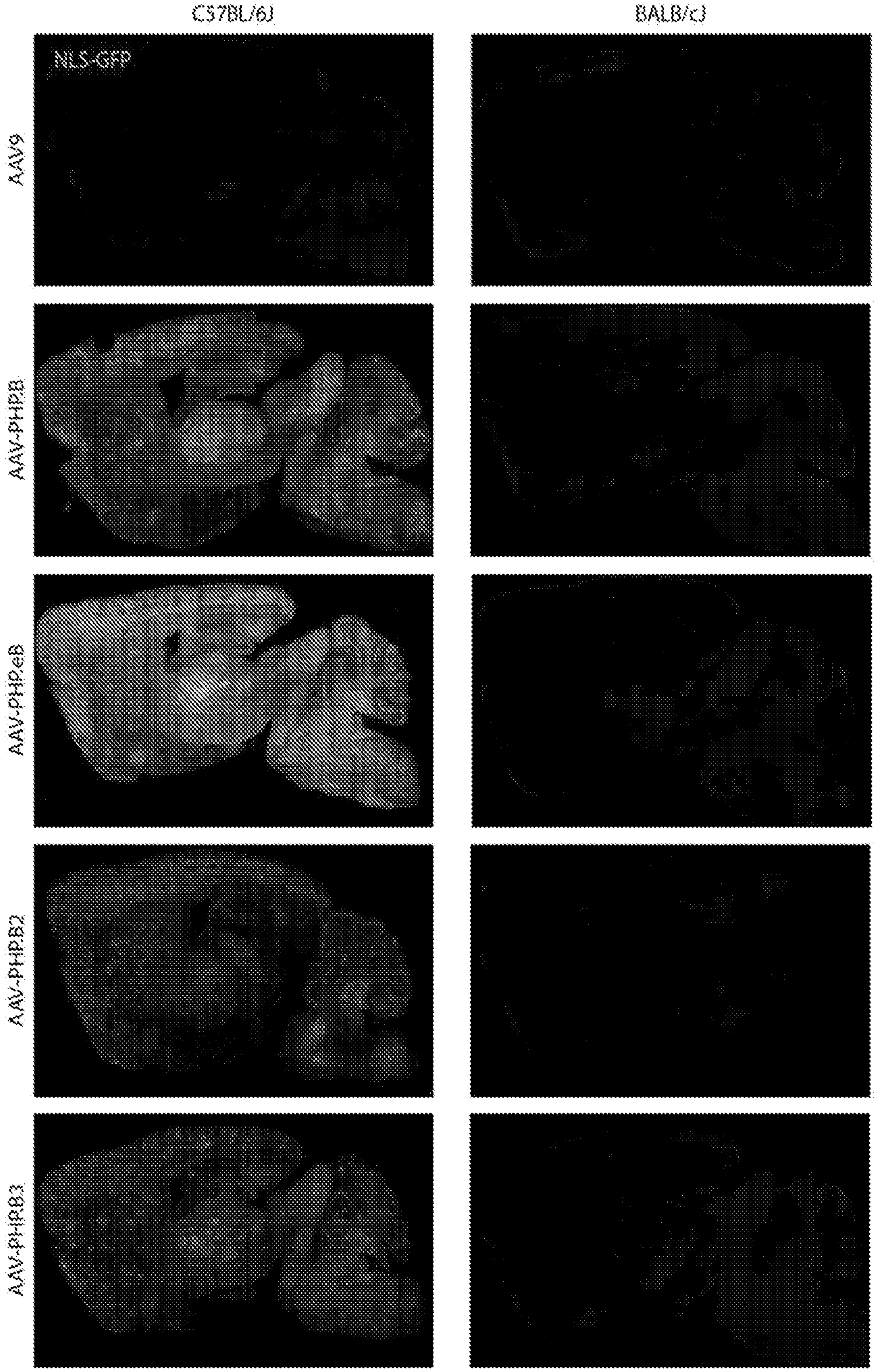
FIG. 6 shows images of GFP fluorescence in whole brain sagittal sections from C57BL/6J (left column) or BALB/cJ (right column) two weeks after intravenous injection of $1\times10^{11}$ vg/mouse AAV-CAG-NLS-GFP packaged into the indicated capsid.
Figure 8A:
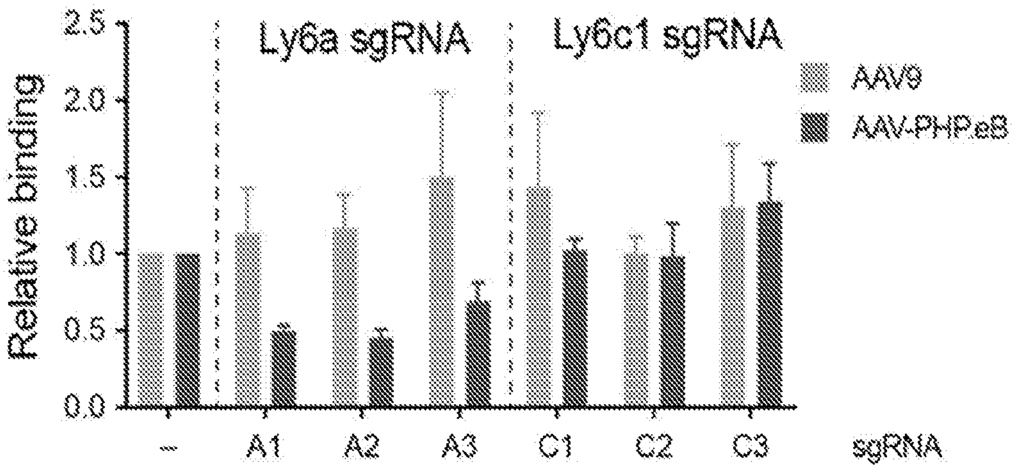
FIG. 8A shows a graph of individual sgRNA data used to generate FIG. 3D.
Figure 8B:
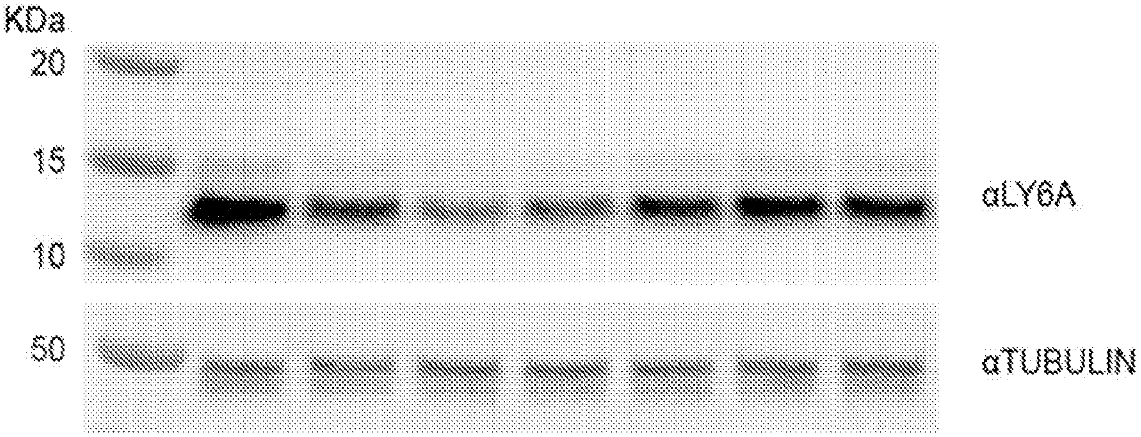
FIG. 8B shows western blots for LY6A (top) or TUBULIN (bottom) in lysates prepared from BMVECs treated with the individual sgRNAs shown in FIG. 7A.

Microsoft Excel and Prism 8 were used for data analysis. For the comparison between AAV9 and AAV-PHP.eB biodistribution, a group size of 6 per group (3 males and 3 females) was used based on prior data that indicated a large effect size (mean±SEM). No animals or samples were excluded from the analysis. FIG. 6 shows images representative of two animals per group. To evaluate AAV-PHP.eB in the 13 mouse lines, AAV9 (n=1, 1011 vg/animal) or AAV-PHP.eB (n=2; 1 per dose at $10^{11}$ and $10^{12}$ vg/animal). LY6A IHC in FIG. 6 are representative of 2 animals/line. In vitro transduction and binding experiments are means from three independent experiments. In FIGS. 3D and 3E, each data point represents a different sgRNA, each averaged from 3 independent experiments. Data were normalized to cells transduced with SpCas9 vectors without a sgRNA. FIGS. 8A-8B presents the same data as FIG. 3D separated by each individual sgRNA. Data from AAVR WT and KO mice are representative of 2 mice per genotype per time point post injection.

RNA Selection Plasmids:

To construct an adeno-associated virus (AAV) RNA expression system for the selection of functional AAV vectors and the recovery of AAV capsid transcripts, the ubiquitous promoter cytomegalovirus (CMV) was cloned into a recombinant AAV plasmid containing inverted terminal repeats from adeno-associated virus type 2 (AAV2). Downstream of the CMV promoter a synthetic intron containing a consensus donor motif (CAGGTAAGT), consensus splice motif (TTTTTTCTACAGGT) (SEQ ID NO: 30229) and branch point sequence was cloned. Downstream of the artificial intron, the AAV5 P41 promoter along with the 3' end of the AAV2 Rep gene, which includes the splice donor sequences for the capsid RNA was cloned. The capsid gene splice donor sequence in AAV2 Rep was modified from a non consensus donor sequence CAGGTACCA to a consensus donor sequence CAGGTAAGT. The wildtype adeno-associated virus serotype 9 (AAV9) capsid gene sequence was synthesized with nucleotide changes at S448 (TCA to TCT, silent mutation), K449R (AAG to AGA), and G594 (GGC to GGT, silent mutation) to introduce XbaI and AgeI restriction enzyme recognition sites for library fragment cloning. The AAV2 polyadenylation sequence was replaced with a simian virus 40 (SV40) late polyadenylation signal to terminate the capsid RNA transcript.

AAV Library Generation:

To assemble an oligonucleotide Library Synthesis Pool (oligo pool; Agilent) into an AAV genome, the oligo pool was amplified and extended using 10 ng of a DNA plasmid template containing a fragment of AAV9 and a forward primer Assembly-XbaI-F. Specifically, the reaction conditions were as follows: approximately 5 pM of the OLS pool, 0.5 μM of primer Assembly-XbaI-F for 5 cycles using Q5® High-Fidelity 2× Master Mix (NEB #M0492S) following the manufacturer's protocol. After the 5-cycle amplification and extension of the oligo pool, the reaction was spiked with 0.5 μM of primer Assembly_AgeI-R and amplified for an additional 25 cycles. The PCR product was then purified using Agencourt AMPure XP SPRI paramagnetic beads (Beckman Coulter #A63880) or column purified using a Zymo Research DNA Clean & Concentrator-5 kit (Zymo Research #D4013) following the manufacturer's protocol.

For generating 7-mer NNK libraries, the hand-mixed primer (Assembly-NNK-AAV9-588; IDT) encoding a 7mer peptide insertion between AA 588 and 589 of AAV9 was used as the reverse primer along with the Assembly-XbaI-F oligo as a forward primer in a PCR reaction using Q5® High-Fidelity 2× Master Mix (NEB #M0492S) following the manufacturer's protocol for 30 cycles with 10 ng plasmid containing AAV9 as the template. The oligo pool or 7-mer NNK PCR products were assembled into the RNA expression plasmid with previous described methods in Deverman et al. *Nature Biotechnology* 2016.

Virus Production and Purification:

Recombinant AAVs were generated and titered with previously described methods in Deverman et al. *Nature Biotechnology* 2016.

RNA Isolation:

To isolate total RNA containing AAV Cap transcripts, a RNeasy Mini Kit (Qiagen #74104), along with a QIAshredder kit (Qiagen #79654) and a RNase-Free DNase kit (Qiagen #79254) was used following the manufacturer's protocol. In some variations, TRIzol™ Reagent (Invitrogen™ #15596026) was used to isolate total RNA from homogenized tissue following the manufacturer's protocol prior to additional cleanup with the RNeasy Mini, QIAshredder and RNase-Free DNase kits listed above. Isolated RNA was resuspended in RNase free water and stored in −80 C conditions until conversion to cDNA.

RT Reaction:

RNA was reverse transcribed to cDNA using Maxima H Minus Reverse Transcriptase (Thermo Scientific™ #EP0752) following the manufacturer's protocol with an anchored oligo dT primer (IDT #51-01-15-08).

PCR Recovery of Library Sequences:

The cDNA was prepared for next-generation sequencing (NGS) with two rounds of polymerase chain reaction (PCR). In the first round of PCR (PCR1), a set of forward primers (Table 1) and reverse primers (Table 2) containing gene specific priming regions and a overhang sequence containing a portion of the Illumina Read 1 sequence (forward primers) or Illumina Read 2 sequence (reverse primers) were used to selectively amplify AAV genomes from the cDNA with Q5® High-Fidelity 2× Master Mix (NEB #M0492S), with 0.5 μM of each primer.

The forward and reverse primers contain zero or up to eight N nucleotides inserted in between the gene specific priming region and the partial Illumina Read 1 (forward primers) or Read 2 (reverse primers) overhang sequence. This is to introduce diversity into amplicon during NGS and to offset the constant region of the AAV genome to improve cluster diversity and to increase sequencing quality during Illumina NGS. The forward and reverse primers were paired to produce amplicons of the same size (i.e., SEQ1_F was paired with SEQ1_R, SEQ2_F was paired with SEQ2_R, etc.).

The number of cycles performed in PCR1 was chosen to stop before the exponential amplification phase and was determined with qPCR using FastStart Universal SYBR Green Master (Millipore Sigma #4913850001) or Q5® High-Fidelity 2× Master Mix (NEB #M0492S) with SYBR® Green I nucleic acid stain (VWR #12001-798) diluted from 10,000× to 8× per reaction. The qPCR primers used were SEQ9_F and SEQ1_R with 1 μL cDNA input.

Following PCR1, the amplified DNA was cleaned up using Agencourt AMPure XP SPRI paramagnetic beads (Beckman Coulter #A63880) or column purified using a Zymo Research DNA Clean & Concentrator-5 kit (Zymo Research #D4013) following the manufacturer's protocol. PCR1 samples were then barcoded for Illumina NGS with NEBNext Multiplex Oligos for Illumina Dual Index Primers Set 1 and 2 (NEB #E7600S and #E7780S) with 2 μL PCR1 input and amplified for 5 cycles to generate PCR2 products. The PCR2 products were again purified using Agencourt AMPure XP SPRI paramagnetic beads or column purified using a Zymo Research DNA Clean & Concentrator-5 kit (Zymo Research #D4013) following the manufacturer's protocol.

Preparation of Amplified Sequences for NGS:

The concentrations of purified PCR2 samples were determined using a Qubit™ dsDNA HS Assay Kit (Invitrogen™ #Q32854) then diluted and pooled according to the Illumina Nextseq System Denature and Dilute Libraries Guide or MiSeq System Denature and Dilute Libraries Guide along with 10-15% PhiX Control v3 (Illumina #FC-110-3001) spiked in. The pooled samples were quantified and checked for correct sizes using an Agilent High Sensitivity DNA Kit (Agilent #5067-4626) on an Agilent 2100 Electrophoresis Bioanalyzer.

Then samples were either sequenced on an Illumina NextSeq or Miseq machine using a NextSeq 500/550 High Output Kit v2.5 (150 Cycles) (Illumina #20024907), NextSeq 500/550 Mid Output Kit v2.5 (150 Cycles) (Illumina #20024904) or MiSeq Reagent Kit v3 (150-cycle) #MS-102-3001) with the indexes read from both ends after 150 read cycles.

NGS Analysis:

Following NGS, sequences were aligned to an AAV9 template with 21 N nucleotides insertion between amino acid 588 and 589 to represent the 7mer insertion using Bowtie 2. Further post processing was performed using SAMtools, Python 3, NumPy and Pandas. Briefly, the flanking regions up to the 7mer (prefix) and after the 7mer (suffix) region were clipped. The resulting sequence was checked to be 21 bp in length. The nucleotide sequences were converted to amino acid sequences and exported using Pandas. Read counts associated with each nucleotide sequence were converted to normalized read counts (reads per million) to adjust for sequencing depth differences between samples. Enrichment scores for each sequence are calculated by log 2 (normalized read count post screening/normalized read count in the initial virus library). Primersequences are listed below.

| PCR ROUND 1 FORWARD PRIMERS | SEQUENCES | SEQ ID NO: |
|---|---|---|
| SEQ1_F | CTTTCCCTACACGACGCTCTTCCGATCTNNNNNNNNCCAACGAAGAAGAAATTAAAAC TACTAACCCG | 30229 |
| SEQ2_F | CTTTCCCTACACGACGCTCTTCCGATCTNNNNNNNCCAACGAAGAAGAAATTAAAACT ACTAACCCG | 30230 |
| SEQ3_F | CTTTCCCTACACGACGCTCTTCCGATCTNNNNNNCCAACGAAGAAGAAATTAAAACTA CTAACCCG | 30231 |
| SEQ4_F | CTTTCCCTACACGACGCTCTTCCGATCTNNNNNCCAACGAAGAAGAAATTAAAACTAC TAACCCG | 30232 |
| SEQ5_F | CTTTCCCTACACGACGCTCTTCCGATCTNNNNCCAACGAAGAAGAAATTAAAACTACT AACCCG | 30233 |
| SEQ6_F | CTTTCCCTACACGACGCTCTTCCGATCTNNNCCAACGAAGAAGAAATTAAAACTACTA ACCCG | 30234 |
| SEQ7_F | CTTTCCCTACACGACGCTCTTCCGATCTNNCCAACGAAGAAGAAATTAAAACTACTAA CCCG | 30235 |
| SEQ8_F | CTTTCCCTACACGACGCTCTTCCGATCTNCCAACGAAGAAGAAATTAAAACTACTAAC CCG | 30236 |
| SEQ9 F | CTTTCCCTACACGACGCTCTTCCGATCTCCAACGAAGAAGAAATTAAAACTACTAACC CG | 30237 |

| PCR ROUND 1 REVERSE PRIMERS | SEQUENCES | SEQ ID NO: |
|---|---|---|
| SEQ1_R | GGAGTTCAGACGTGTGCTCTTCCGATCTCATCTCTGTCCTGCCAAACCATACC | 30238 |
| SEQ2_R | GGAGTTCAGACGTGTGCTCTTCCGATCTNCATCTCTGTCCTGCCAAACCATACC | 30239 |
| SEQ3_R | GGAGTTCAGACGTGTGCTCTTCCGATCTNNCATCTCTGTCCTGCCAAACCATACC | 30240 |
| SEQ4_R | GGAGTTCAGACGTGTGCTCTTCCGATCTNNNCATCTCTGTCCTGCCAAACCATACC | 30241 |
| SEQ5_R | GGAGTTCAGACGTGTGCTCTTCCGATCTNNNNCATCTCTGTCCTGCCAAACCATACC | 30242 |
| SEQ6_R | GGAGTTCAGACGTGTGCTCTTCCGATCTNNNNNCATCTCTGTCCTGCCAAACCATAC C | 30243 |
| SEQ7_R | GGACTTCAGACGTGTGCTCTTCCGATCTNNNNNNCATCTCTGTCCTGCCAAACCATA CC | 30244 |
| SEQ8_R | GGAGTTCAGACGTGTGCTCTTCCGATCTNNNNNNNCATCTCTGTCCTGCCAAACCAT ACC | 30245 |
| SEQ9_R | GGACTTCAGACGTGTCCTCTTCCGATCTNNNNNNNNCATCTCTGTCCTGCCAAACCA TACC | 30246 |

Assembly Primers

| ASSEMBLY PRIMER | SEQUENCES | SEQ ID NO: |
|---|---|---|
| Assembly-XbaI-F | CACTCATCGACCAATACTTGTACTATCTCT | 30247 |
| Assembly_AgeI-R | GTATTCCTTGGTTTTGAACCCAACCG | 30248 |
| Assembly-NNK-AAV9-588 | GTATTCCTTGGTTTTGAACCCAACCGGTCTgcgcctgtgc(M:50500000)(N:2525 2525)(N)(M)(N)(N)(M)(N)(N)(M)(N)(N)(M)(N)(N) M)(N)(N)(M)(N) (N)TTGGGCACTCTGGTGGTTTGTG | 30249 |

Ly6-Fc Fusion Protein Production

The coding regions including the signal peptide and mature protein sequences were amplified with the primers below and inserted into pCMV6-XL4 FLAG-NGRN-Fc (Addgene #115773) with EcoRV and XbaI sites.

| Protein | Sequence | SEQ ID NO: |
|---|---|---|
| Ly6A | GAGCTCGTTTAGTGAACCGTCAGATATCGCCACCATGGACACTTC | 30250 |
| | CAGGCCCCTGGAAGAGCACCTCTAGACCGCCTCCATTGGGAAC | 30251 |
| Ly6C | GAGCTCGTTTAGTGAACCGTCAGATATCGCCACCATGGACACTTC | 30252 |
| | AGGCCCCTGGAAGAGCACCTCTAGACCACCTGCAGTGGGAACTGC | 30253 |
| hCD59 | GCTCGTTTAGTGAACCGTCAGATATCGCCACCATGGGAATCCAAG | 30254 |
| | CCTGGAAGAGCACCTCTAGACCATTTTCAAGCTGTTCGTTAAAGTTACAC | 30255 |
| hLy6E | GTTTAGTGAACCGTCAGATATCGCCACCATGAAGATCTTCTTGCC | 30256 |
| | GGCCCCTGGAAGAGCACCTCTAGACCACTGAAATTGCACAGAAAGCTCTG | 30257 |

Expression and Purification of Fc-Tagged Protein in HEK293-FT Cells 26 million HEK293-FT cells were seated per 150 mm plate the day before transfection. The next day, complete media was changed to Pro293™a-CDM™ media with two brief rinses with Pro293™a-CDM™ media to remove serum. Cells were transduced with PEI and 40 ug DNA per plate a few hours after media change. The media was replaced 18 hours after transfection. At the second day post-transfection, cell supernatants containing secreted recombinant protein were passed through a 0.45-mm pore size filter and purified on Protein A-Sepharose. 200 ul Protein A-Sepharose were incubated with 100 ml cell culture supernatant overnight at 4 C with shaking. The next day, the beads were collected and washed 3 times with 10 ml of PBS, and the proteins were eluted in 200 ul of 100 mM glycine (pH2.7). Then 1/10 volume of 1M Tris (pH8.8) was added to the eluted protein fractions to neutralize the pH.

Virus Pull Down with Purified Fc-Tagged Protein 0.5 or 1 ug of purified recombinant Fc fusion proteins or Fc control protein was incubated with 10 ul magnetic Protein A beads for 4 hrs at 4 C with rotation in PBS with 0.05% Tween-20. Supernatant was removed and 1E10 vg of an AAV9 K449R 7-mer virus library in PBS was added into beads pellet and incubated overnight. The next day, after three washes, bound virus were released with Proteinase K treatment and the viral DNA genomes were purified with Agencourt AMPure XP. The viral genomes were then amplified by PCR and processed and indexed for NGS.

Example 2: Ly6 Genetic Variants Associate with the CNS Tropism of AAV-PHP.eB

Figure 1B:
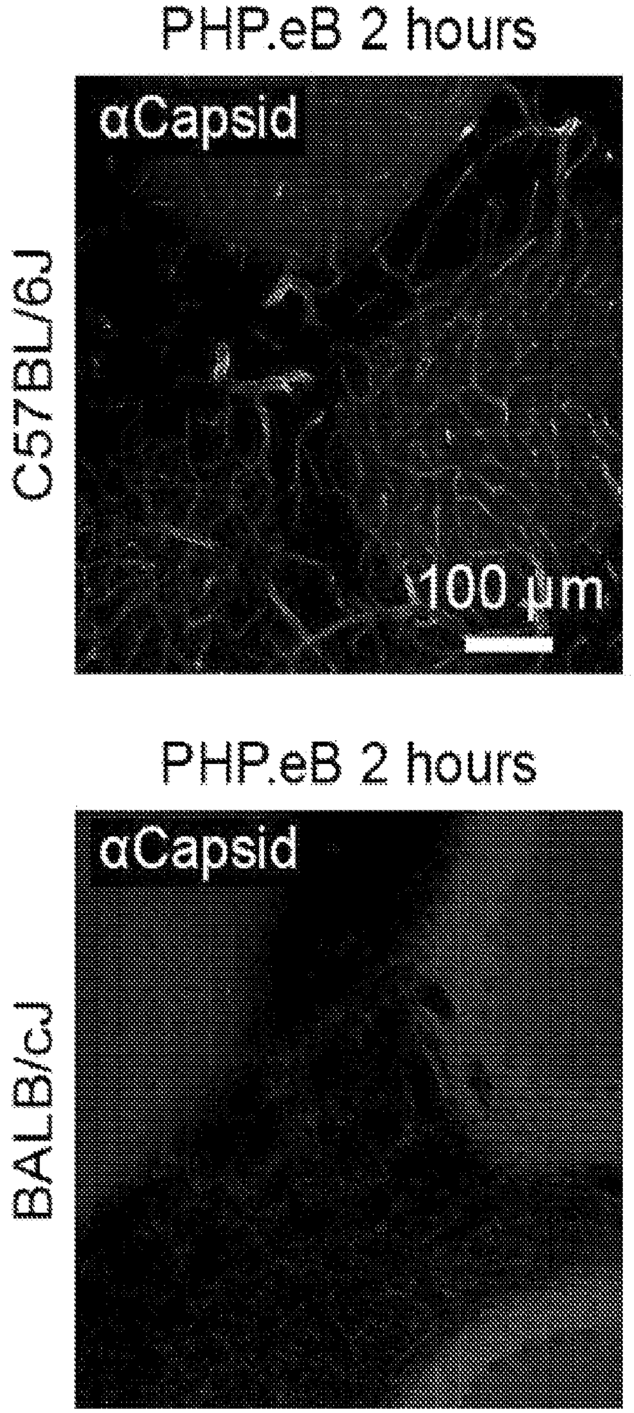
FIG. 1B shows images of AAV capsid IHC within the cerebellum one hour after intravenous injection of AAV-PHP.eB.
Figure 1C:
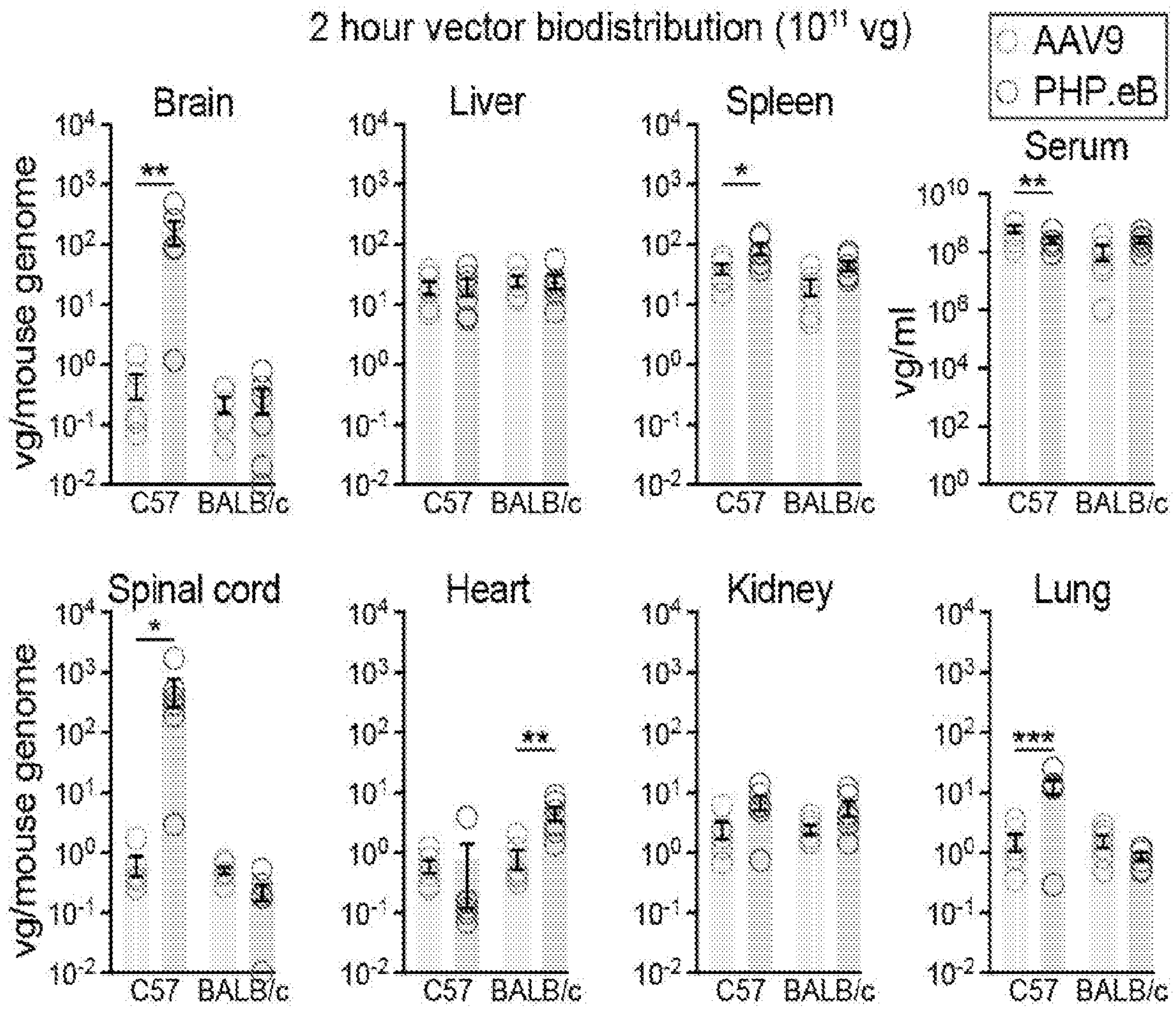
FIG. 1C shows graphs of vector genome (vg) biodistribution of AAV-PHP.eB or AAV9 two hours after intravascular administration to C57BL/6J or BALB/cJ mice (n=6/virus/line, mean±s.e.m.; 2-way ANOVA; *p<0.05, p<0.01, *p<0.001).
Figure 1D:
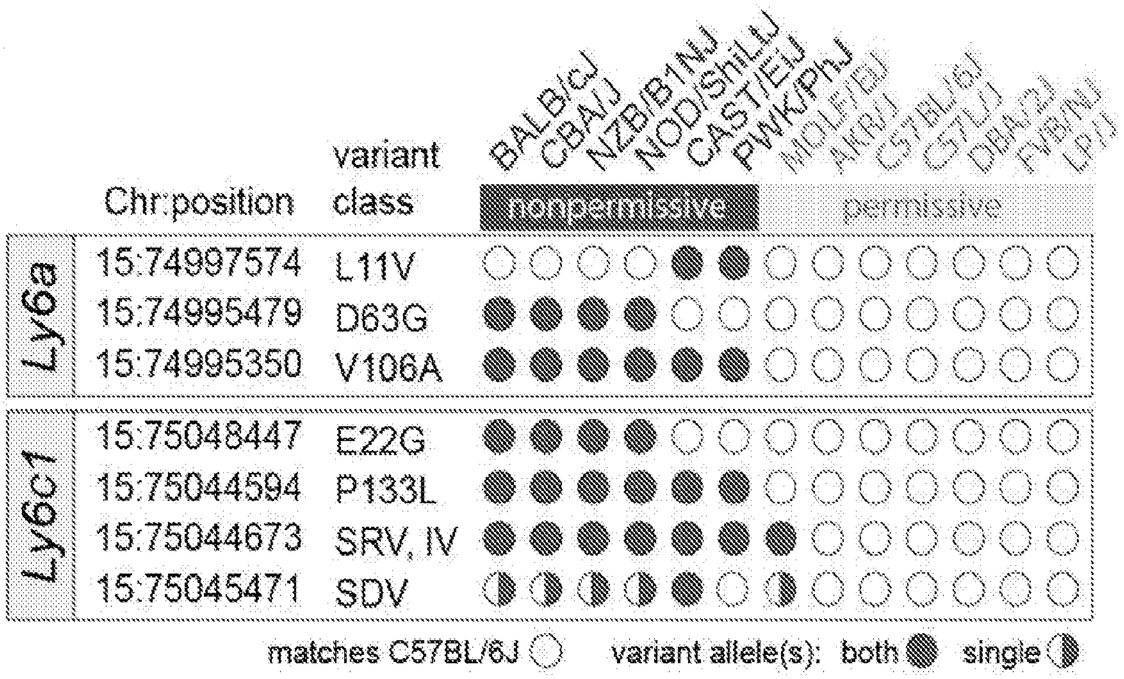
FIG. 1D shows data of Ly6a and Ly6c1 SNPs correlated with the nonpermissive phenotype. Missense SNPs relative to C57BL/6J are listed as the amino acid change. SRV, splice region variant; IV, intron variant; SDV, splice donor variant.

The dramatic difference in the CNS tropism of AAV-PHP.B in C57BL/6J versus BALB/cJ mice (19) extends to AAV-PHP.eB (FIG. 1A) and is consistent with reduced AAV-PHP.eB association with the endothelium (FIG. 1B), which partially constitutes the BBB. The increased accumulation of AAV-PHP.eB relative to AAV9 in the brain and spinal cord of C57BL/6J mice is absent in BALB/cJ mice (FIG. 1C). Two AAV-PHP.B capsids, AAV-PHP.B2 and AAV-PHP.B3 (5), were similarly unable to transduce the BALB/cJ CNS (FIG. 6).

These results prompted a search for candidate genes associated with enhanced AAV-PHP.B CNS transduction. Studies were aimed to test the AAV-PHP.B capsids across a panel of mouse lines, and harness the natural genetic variation between mice to identify the genetic variants and, subsequently, candidate gene(s) responsible for the difference in CNS transduction by AAV-PHP.eB. Using the open-source software Hail (24), a genome-wide database of variants across 36 mouse lines (25) was analyzed. Starting from millions of genetic variants, comprised of single-nucleotide polymorphisms (SNPs) as well as insertions and deletions (indels), the analysis was narrowed to variants predicted to affect expression, splicing, or protein coding regions (Table 2). As in a genetic linkage study, the aim was to rapidly identify variants whose alleles segregate across mice with the observed phenotype (permissive or non-permissive). Using a statistical simulation framework, it was estimated that 12 mouse lines would be sufficient to narrow our search to ~10 high/medium impact variants (FIG. 9, Table 2) that could feasibly be experimentally interrogated for the enhanced AAV-PHP.eB CNS tropism.

TABLE 2

The types of genetic variants included in the linkage study. The variant types, their count among all 36 mouse strains in the in the mouse genome project (4, 5) database, and their predicted impact is shown. Analysis was restricted to variant types with high or medium likelihood of impacting gene expression or coding sequence.

| Abbreviation | Variant type | Count | Impact |
|---|---|---|---|
| INT | Intron variant | 38745814 | Low |
| DWNGV | Downstream gene variant | 9820625 | Low |
| UPGV | Upstream gene variant | 9709435 | Low |
| NTV | Noncoding transcript variant | 5864559 | Low |
| NTEV | Noncoding transcript exon variant | 1041185 | Low |
| 3UTR | 3' Prime UTR variant | 823815 | Low |
| SYN | Synonymous variant | 344244 | Low |
| MS | Missense variant | 216611 | Medium |
| 5UTR | 5' UTR variant | 128375 | Low |
| NMD | NMD transcript variant | 123148 | Low |
| SRV | Splice region variant | 80431 | Medium |
| INFD | Inframe deletion | 3502 | Medium |
| FST | Frameshift variant | 2711 | High |
| SDV | Splice donor variant | 2609 | HIgh |
| INFI | Inframe insertion | 2452 | Medium |
| SG | Stop gained | 2450 | HIgh |
| SAV | Splice acceptor variant | 1922 | High |
| MIR | Mature miRNA variant | 1220 | Low |
| STPRV | Stop retained variant | 370 | Low |
| STPL | Stop lost | 332 | High |
| SRTL | Start lost | 322 | Medium |
| CSV | Coding sequence variant | 193 | Low |
| PAV | Protein altering variant | 87 | Low |
| ITCV | Incomplete terminal codon variant | 75 | Low |
| STPRV | Start retained variant | 31 | Low |

Figure 9:
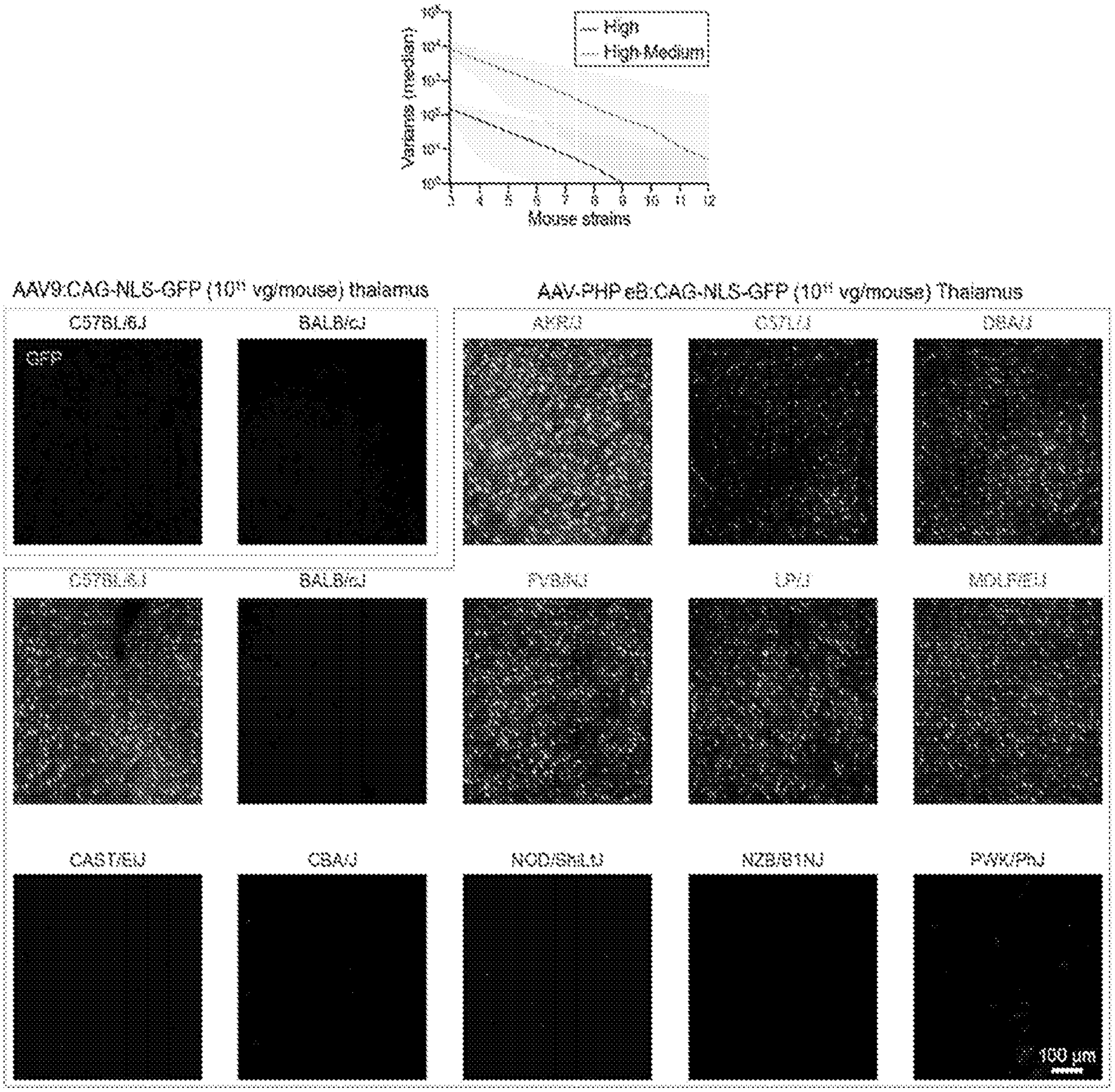
FIG. 9 shows the predicted number of mouse strains required to reduce the number of candidate gene variants associated with AAV-PHP.eB permissivity. The plotted lines depict the median number of simulated candidate variants; high (loss-of-function; blue) or high+medium (loss-of-function, missense, splicing variant; orange). Shaded regions represent 5-95$^{th}$ percentiles. Images show data of native GFP fluorescence in the mouse thalamus two weeks after intravenous injection of $1\times10^{11}$ vg/mouse CAG-NLS-GFP packaged into AAV9 (first two panels from top left) or AAV-PHP.eB.

Accordingly, mice from 13 commercially available lines were acquired, including C57BL/6J and BALB/cJ, and administered $10^{11}$ vector genomes (vg)/animal of AAV-PHP.eB, which packaged an AAV genome encoding an enhanced green fluorescent protein (GFP) with a nuclear localization signal (NLS-GFP). As observed with AAV-PHP.B, intravenous administration of AAV-PHP.eB resulted in GFP expression throughout the brain of permissive lines such as C57BL/6J, but not those of nonpermissive mice such as BALB/cJ; seven permissive and six nonpermissive lines were identified (FIG. 9).

Figure 1E:
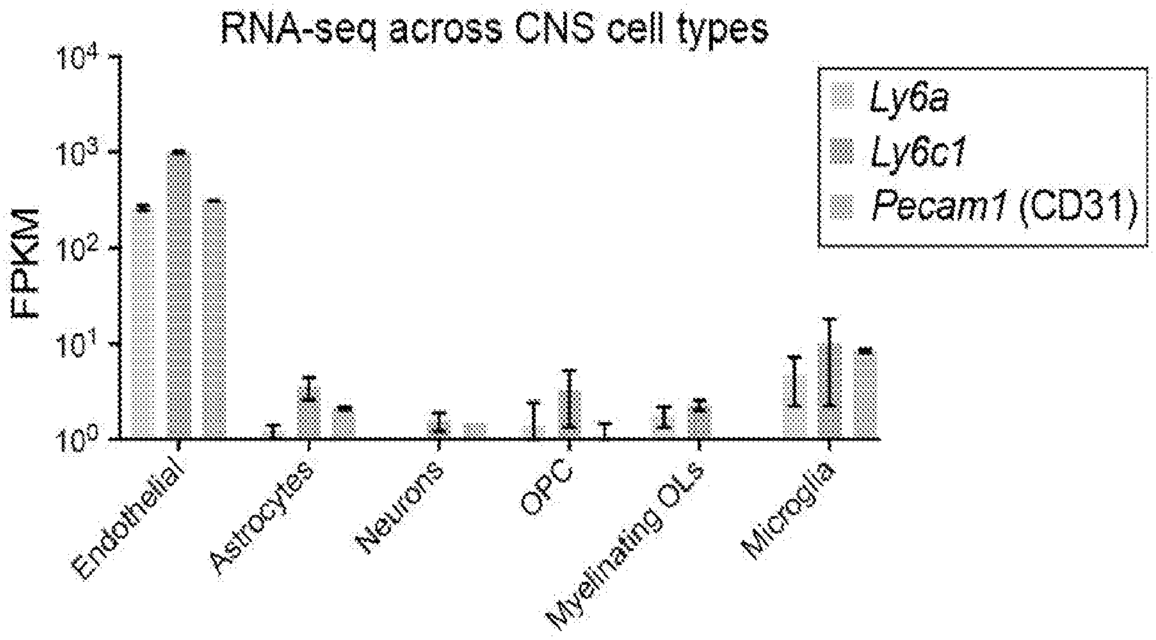
FIG. 1E shows expression data (mean fragments per kilobase-million±s.d.) for Ly6a, Ly6c1, and Pecam1 (Hail; available at github.com/hail-is/hail).

Hail analysis reduced the number of high or medium impact gene variants to missense SNPs in the related Ly6a and Ly6c1 genes (FIG. 1E). RNA sequencing data from sorted mouse brain cells (www.BrainRNAseq.org) (26) indicates that Ly6a and Ly6c1 are highly expressed in brain endothelial cells (FIG. 1F). Intriguingly, the mouse Ly6 locus has been linked to susceptibility to mouse adenovirus (MAV1) (27), which possesses a tropism for endothelial cells that causes fatal hemorrhagic encephalomyelitis in C57BL/6 but not BALB/cJ mice (28). The Ly6 gene family also influences susceptibility to infection by HIV1 (29, 30), Flaviviridae (yellow fever virus, dengue, and West Nile virus (31), Influenza A (32), and Marek's disease virus in chickens (33).

Figure 2A:
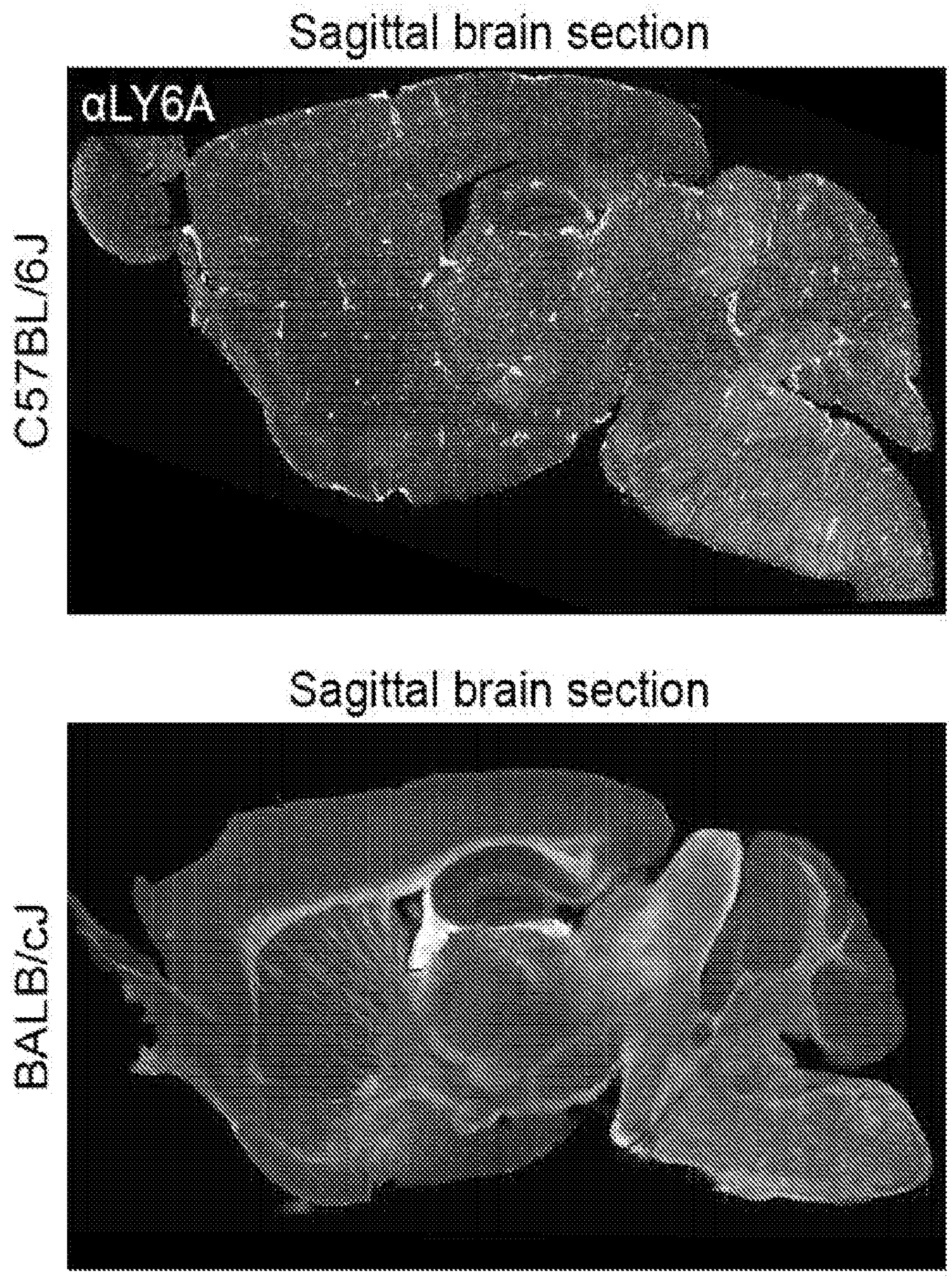
FIG. 2A shows images of LY6C$_1$ IHC in the cerebellum of C57BL/6J (top) or BALB/cJ (bottom) mice.
Figure 2B:
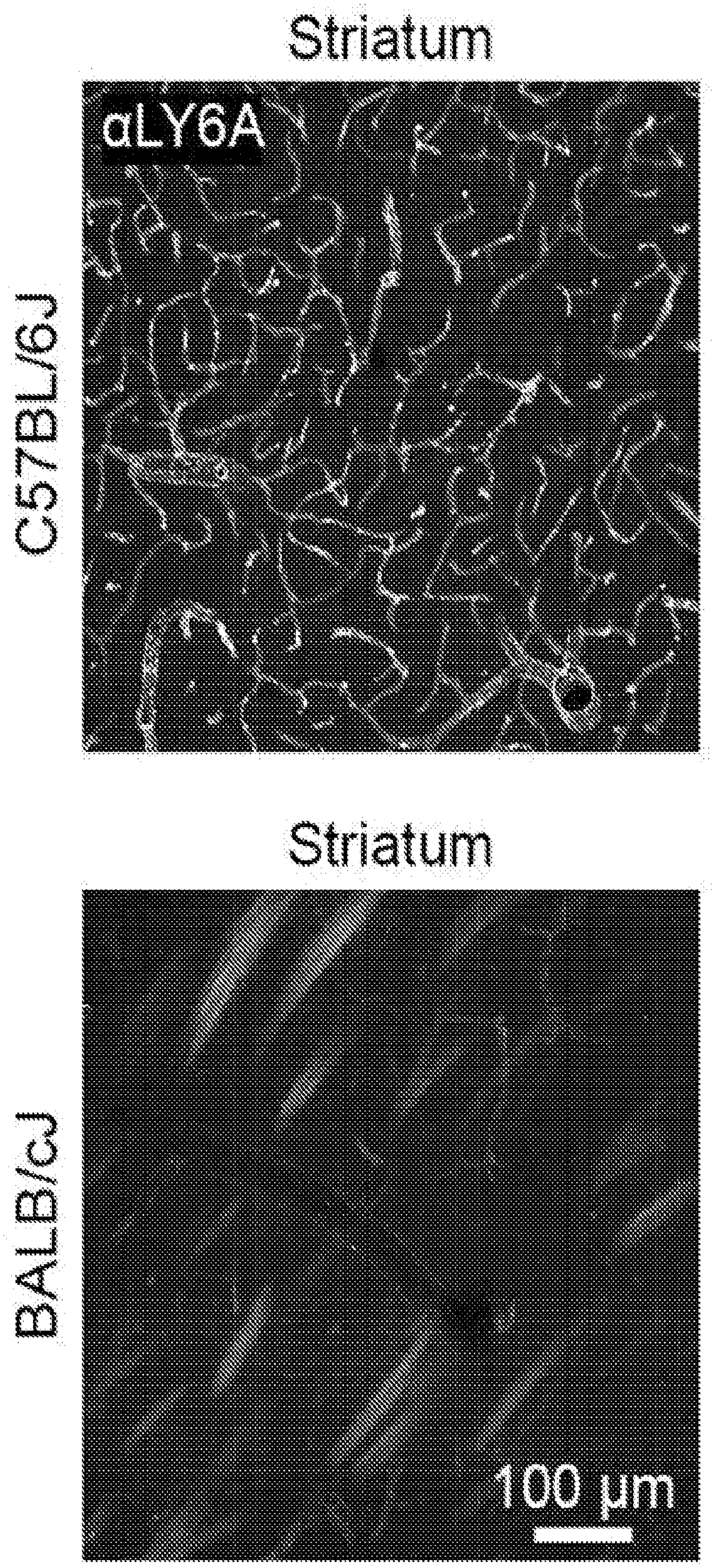
FIG. 2B shows images of LY6A IHC in the cerebellum of C57BL/6J (top) or BALB/cJ (bottom) mice.
Figure 7:
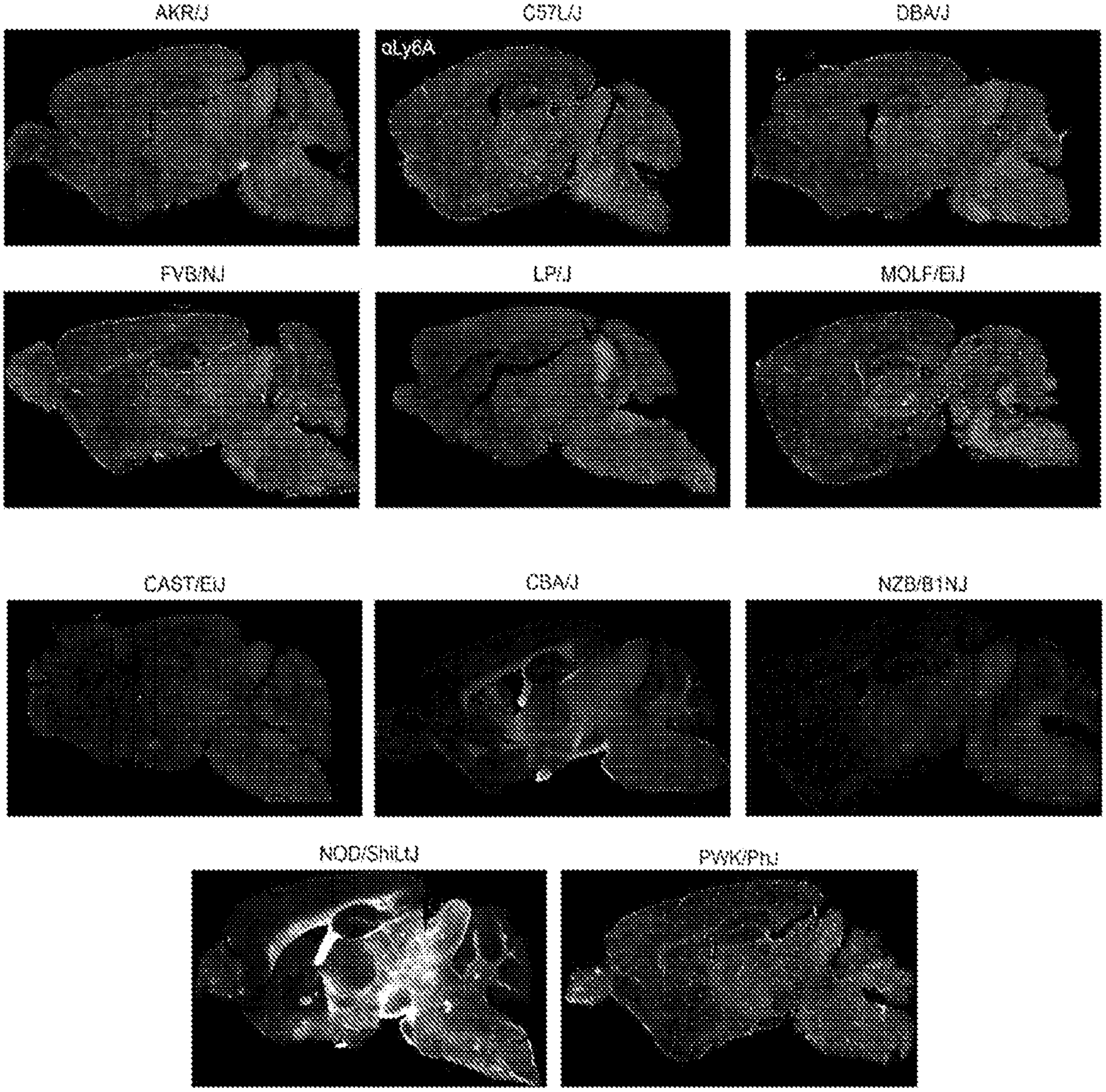
FIG. 7 shows sagittal whole brain images of LY6A IHC in several representative permissive and nonpermissive mouse lines.

Based on these findings, the possibility that genetic variation within Ly6a or Ly6c1 is associated with the differential AAV-PHP.eB tropism across mouse lines was analyzed. Immunohistochemistry (IHC) assays for LY6A and LY6C1 in C57BL/6J and BALB/cJ mice were performed to assess their expression and localization (FIG. 2B). LY6A was abundant within the CNS endothelium of C57Bl/6J mice but notably less abundant in BALB/cJ mice (FIGS. 2A-2B). The reduced LY6A on CNS vasculature correlated with the nonpermissive AAV-PHP.eB transduction phenotype across all of the tested mouse lines (FIG. 7). In contrast, Ly6c1 was expressed on the CNS endothelium of both lines (FIG. 2B). Western blotting demonstrated that LY6A is evident as multiple bands, but only the more slowly migrating band is detectable at low levels in BALB/cJ mice (FIG. 2D), suggesting that the maturation or post-translational processing differ between the two mouse lines. Interestingly, in a subset of the nonpermissive mouse lines, including BALB/cJ, LY6A immunostaining was localized to white matter tracts within the CNS (FIGS. 2A-2B). This myelin-associated immunostaining was observed with two commonly used LY6A monoclonal antibodies (D7 and E13 161-7) and has been previously reported (34, 35).

Taken together, these results suggest an association between Ly6a gene variants, the abundance of specific forms of LY6A within brain endothelial cells, and permissivity to transduction by AAV-PHP.eB.

Example 3: Ly6a is Necessary for the Enhanced CNS Transduction Phenotype of AAV-PHP.eB Whether LY6A and/or LY6C1 are necessary for the ability of AAV-PHP.eB to bind and transduce CNS endothelial cells was analyzed. To achieve this, Ly6a and Ly6c1 knockout experiments were performed in brain microvascular endothelial cells (BMVECs) from C57BL/6J mice, which express both genes and are more efficiently transduced by AAV-PHP.eB than by AAV9 (FIGS. 3A-3C). CRISPR/Sa-CAS9 (36) and Ly6a- or Ly6c1-specific sgRNAs were used to disrupt each gene. Because BMVECs are primary cells with limited expansion capabilities, assay were run on unselected cells, achieving a ~50% reduction of LY6A (FIG. 7). Nevertheless, using three different sgRNAs targeted to Ly6a, a consistent 50% reduction in binding by AAV-PHP.eB, but not AAV9 (FIG. 3D and FIGS. 8A-8B) was observed; a similar reduction in transduction by AAV-PHP.eB was observed (FIG. 3E). AAV9 transduction of BMVECs was inefficient and not included. None of the sgRNAs targeting Ly6c1 affected AAV-PHP.eB or AAV9 binding to the BMVECs (FIG. 3D). The reduction in AAV-PHP.eB binding resulting from Ly6a disruption in BMVECs, the high level of Ly6a expression within the CNS endothelium of permissive mouse lines, and the association of a V106A SNP in Ly6a with the nonpermissive phenotype, collectively suggest that LY6A functions as a receptor for AAV-PHP.eB.

Example 4: AAV-PHP.eB Directly Interacts with LY6A

Figure 3F:
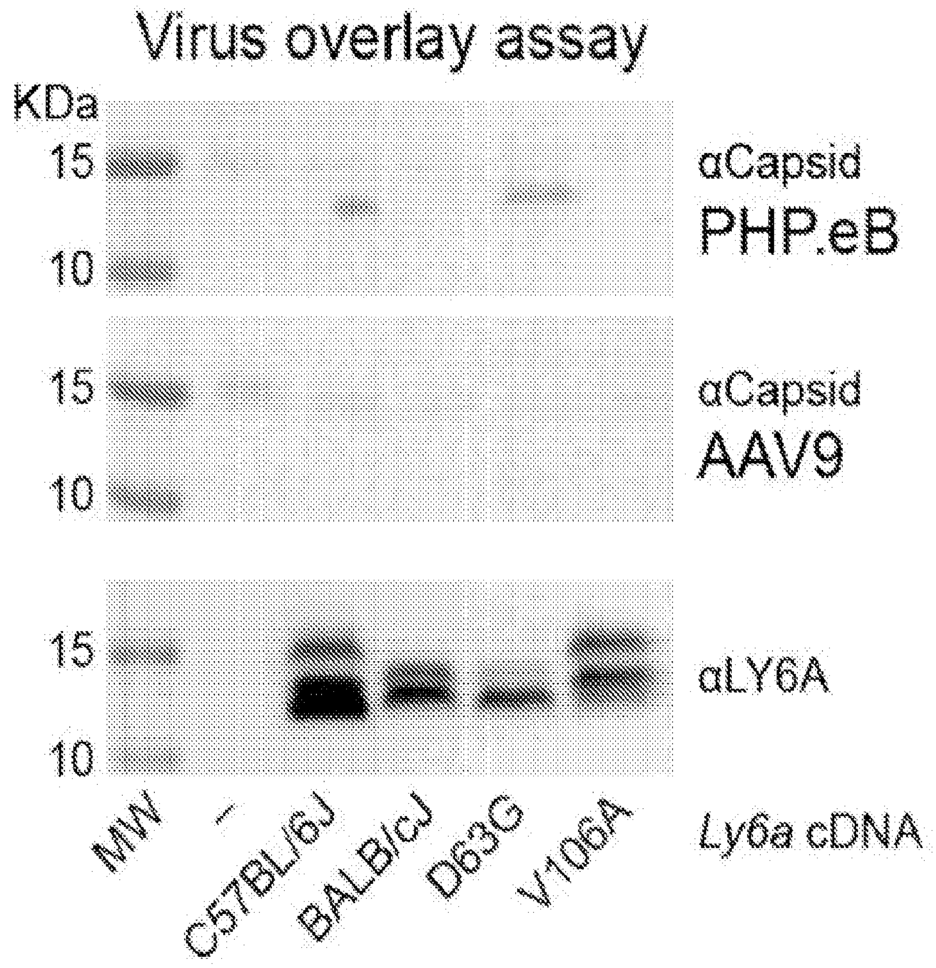
FIG. 3F shows a western blot from a virus overlay assay using lysates from HEK293T cells transfected with Ly6a cDNAs from C57BL/6J or containing one or both BALB/cJ SNPs. Panels show immunoblotting for AAV capsid proteins after overlaying with AAV-PHP.eB or AAV9. Bottom panel shows the same blot probed with αLY6A.

To determine whether AAV-PHP.eB directly binds LY6A and whether either of the missense SNPs in the BALB/cJ Ly6a gene (FIG. 1E) affect this interaction, virus overlay assays were performed (37). HEK293T cells were transfected with Ly6a cDNAs from C57BL/6J, BALB/cJ mice, or cDNAs harboring only one of the two missense SNPs (D63G or V106A). The virus overlay assays using these cell lysates revealed that AAV-PHP.eB binds a protein that co-migrates with LY6A (FIG. 3F) from cells transfected with the C57BL/6J or D63G Ly6a cDNAs, but not from cells expressing Ly6a from the BALB/cJ or V106A cDNAs. The V106A variant is located near the predicted cleavage and GPI anchoring site (w); the presence of an alanine at this position is predicted to reduce the likelihood of GPI-anchor modification (38) (Table 3).

TABLE 3

LY6A from C57Bl/6J but not BALB/cJ mice is predicted to be GPI anchored.

| Gene (strain) | co-site prediction | Specificity | Probability | Sequence | SEQ ID NO: |
|---|---|---|---|---|---|
| Ly6a (C57Bl/6J; DBA/J;AKR/J) | 110 | 100% | Highly Probable | MDTSHTTKSCLLILLVALLC AERAQGLECYQCYGVPFET SCPSITCPYPDGVCVTQEAA VIVDSQTRKVKNNLCLPICP PNIESMEILGTKVNVKTSCC QEDLCNVAVPNGGSTWTM AGVLLFSLSSVLLQTLL | 15 |
| Ly6a (CAST/EiJ; PWK/PhJ) | 110 | 0% | Not GPI-anchored | MDTSHTTKSCVLILLVALL CAERAQGLECYQCYGVPFE TSCPSITCPYPDGVCVTQEA AVIVDSQTRKVKNNLCLPIC PPNIESMEILGTKVNVKTSC CQEDLCNAAVPNGGSTWT MAGVLLFSLSSVLLQTLL | 16 |

TABLE 3-continued

| LY6A from C57Bl/6J but not BALB/cJ mice is predicted to be GPI anchored. | | | | | |
|---|---|---|---|---|---|
| Gene (strain) | co-site prediction | Specificity | Probability | Sequence | SEQ ID NO: |
| Ly6a (BALB/C; NOD/ShiLtJ) | 110 | 0% | Not GPI-anchored | MDTSHTTKSCLLILLVALLC AERAQGLECYQCYGVPFET SCPSITCPYPDGVCVTQEAA VIVGSQTRKVKNNLCLPICP PNIESMEILGTKVNVKTSCC QEDLCNAAVPNGGSTWTM AGVLLFSLSSVLLQTLL | 17 |
| Ly6c1 (C57Bl/6J) | 102 | 100% | Highly Probable | MDTSHTTKSCVLILLVALL CAERAQGLQCYECYGVPIE TSCPAVTCRASDGFCIAQNI ELIEDSQRRKLKTRQCLSFC PAGVPIRDPNIRERTSCCSE DLCNAAVPTAGSTWTMAG VLLFSLSSVVLQTLL | 18 |
| Ly6e | 107 | 100% | Highly Probable | MSATSNMRVFLPVLLAALL GMEQVHSLMCFSCTDQKN NINCLWPVSCQEKDHYCIT LSAAAGFGNVNLGYTLNK GCSPICPSENVNLNLGVASV NSYCCQSSFCNFSAAGLGL RASIPLLGLGLLLSLLALLQ LSP | 19 |

Example 5: Ly6a Expression Enhances Transduction by AAV-PHP.eB

Figure 3G:
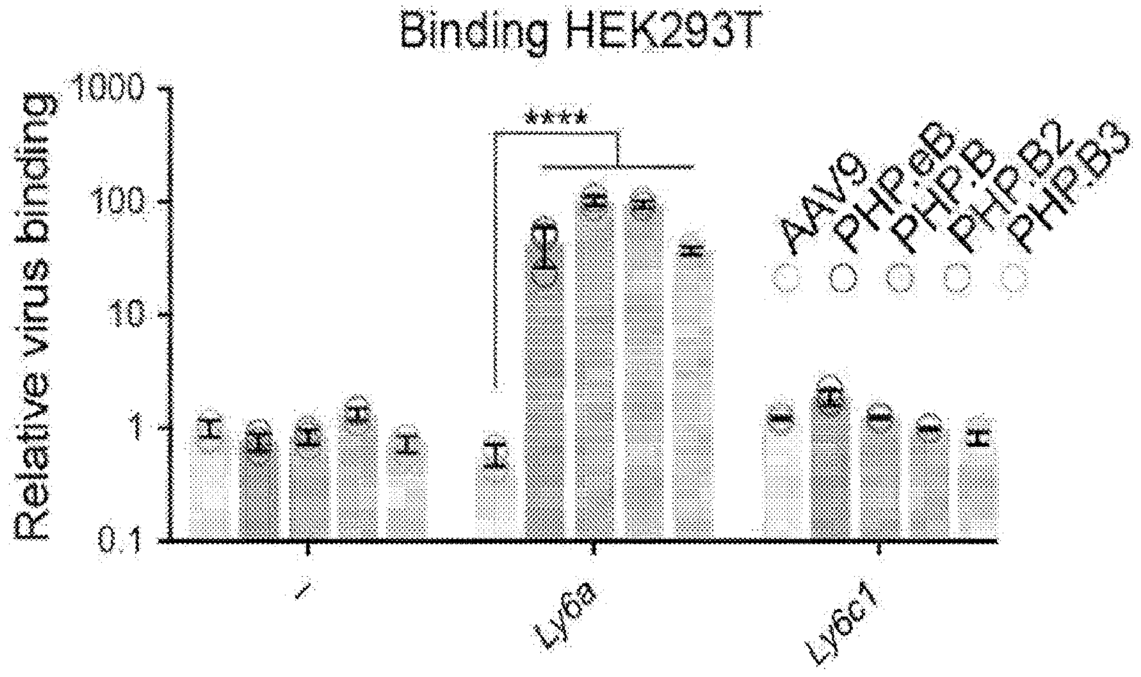
FIG. 3G shows a graph of binding of the indicated virus to HEK293T cells transfected with Ly6a. Ly6c1, or mock (−) (n=3/sgRNAs with 3 sgRNAs per gene, p<0.01, **p<0.0001; 2-way ANOVA, Tukey correction).
Figure 3H:
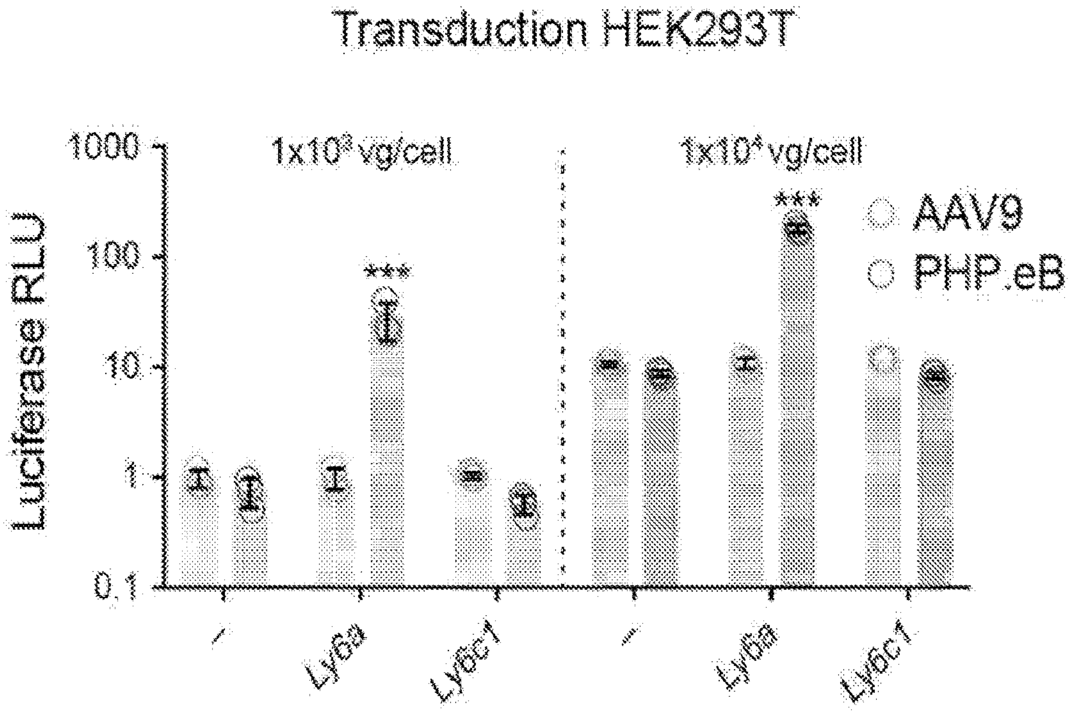
FIG. 3H shows a graph of transduction measured by Luciferase assay normalized to AAV9 on mock transfected cells (n=3, ***p<0.001, 3-way anova, Tukey correction).
Figure 3I:
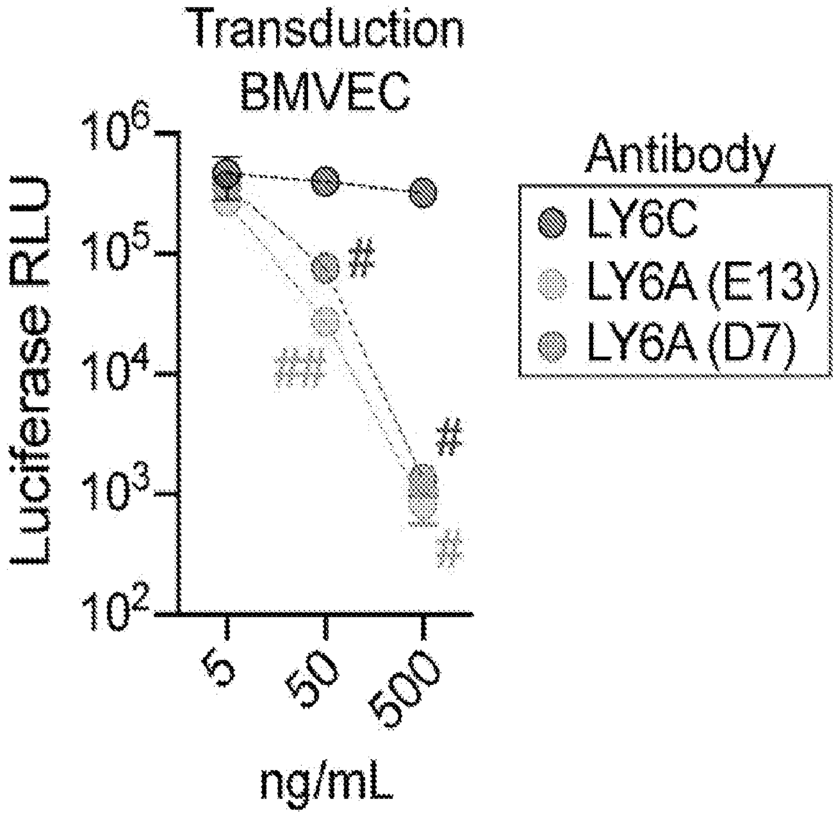
FIG. 3I shows a graph of AAV-PHP.eB-mediated transduction (Luciferase RLU) of BMVECs following the pre-incubation of cells with the indicated antibody (n=2/group, #p=0.023, ##p=0.010, *p=0.001, **p<0.0001, αLY6C vs. αLY6A, 2-way ANOVA, Tukey's correction for multiple comparisons)
Figure 3J:
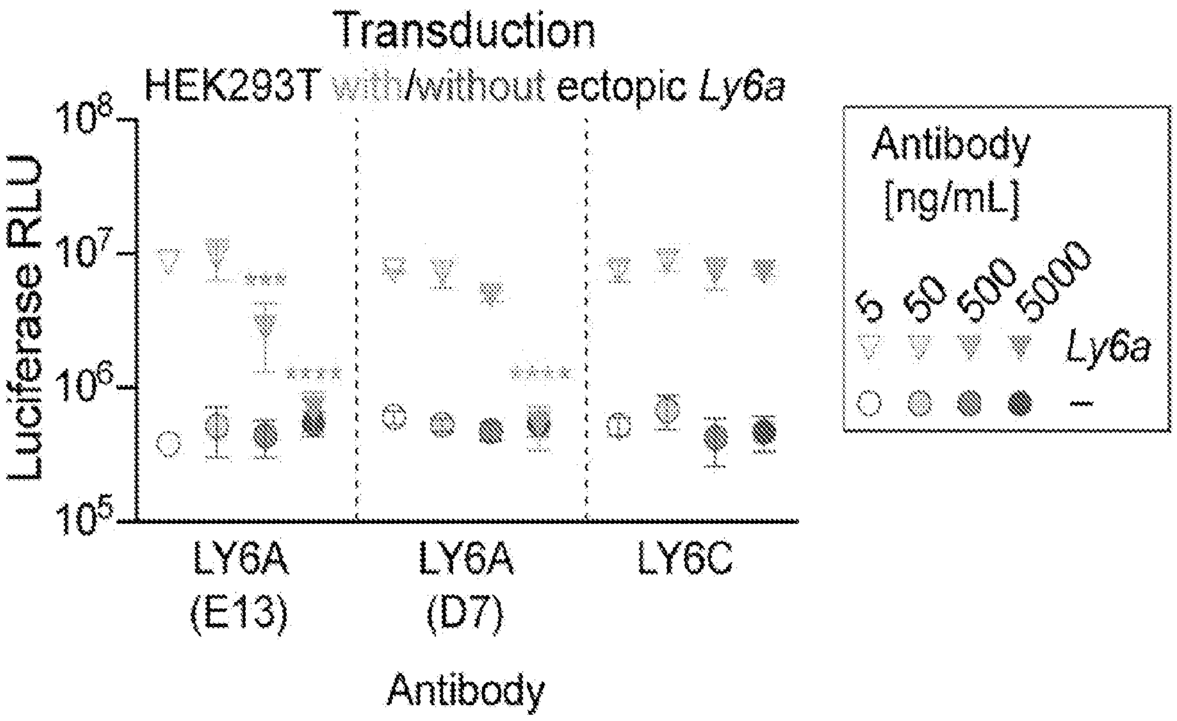
FIG. 3J shows a graph of AAV-PHP.eB-mediated transduction (Luciferase RLU) of HEK293 cells mock ransfected (—) or transfected with Ly6a (I) following the pre-incubation of cells with the indicated antibody (n=3/group, #p=0.023, ##p=0.010, *p=0.001, **p<0.0001, αLY6C vs. αLY6A, 2-way ANOVA, Tukey's correction for multiple comparisons)

Whether ectopic Ly6a expression is sufficient for increased binding and transduction by AAV-PHP.eB was investigated. HEK293T cells were transiently transfected with cDNAs encoding C57BL/6J Ly6a or Ly6c1 and the effects on binding and transduction by AAV-PHP.B capsids was evaluated. Remarkably, Ly6a expression resulted in a >50-fold increase in binding by each of the AAV-PHP.B capsids to HEK293T cells, but did not increase binding by AAV9 (FIG. 3G). Expression of Ly6a, but not Ly6c1, enhanced transduction by AAV-PHP.eB by 30-fold compared to the untransfected control (FIG. 3H).

Figure 4A:
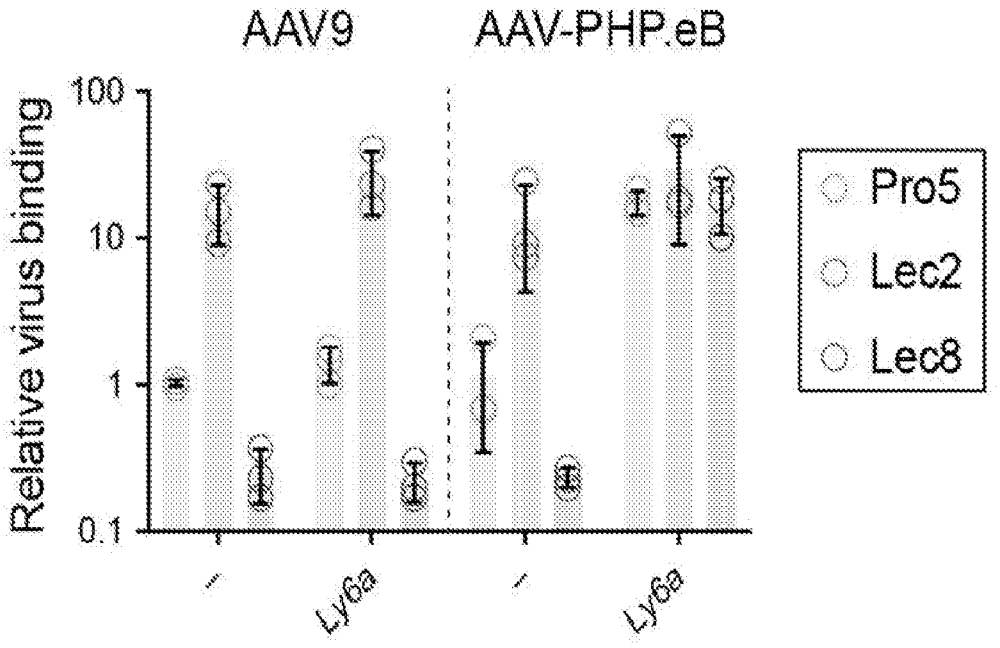
FIG. 4A shows a graph of quantification of AAV binding to CHO cell derivatives via qPCR for viral genomes. AAV-PHP.eB or AAV9 viruses were added to control Pro5 CHO cells, Lec2 CHO cells with excess galactose, or Lac8 CHO cells deficient for galactose transfer.
Figure 4B:
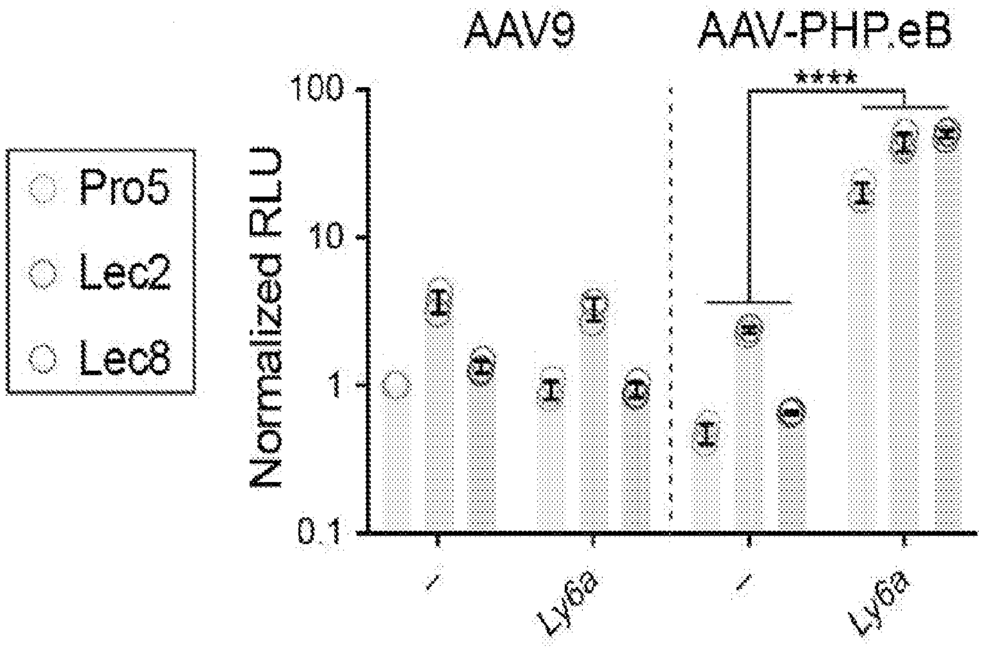
FIG. 4B shows a graph of transduction of CHO cells as measured by Luciferase assay 48 hours after virus addition, normalized to values from Pro5 cells transduced with AAV9.
Figure 4C:
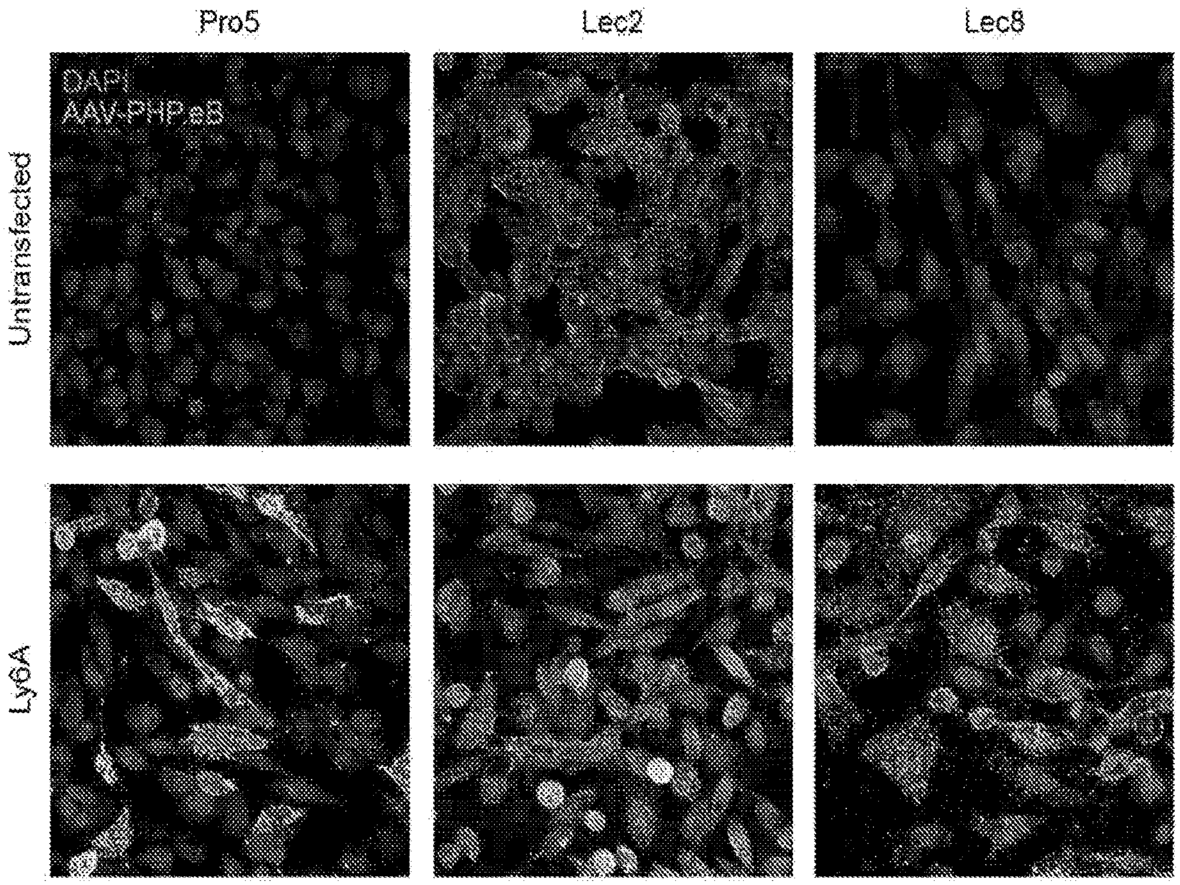
FIG. 4C shows images of AAV-PHP.eB capsid immunostaining of CHO cells that were untransfected (top row) or transfected with Ly6a (bottom row).

Example 6: LY6A Enhances AAV-PHP.eB Transduction Independently of Known AAV9 Receptors To determine whether LY6A acts solely as a primary attachment factor or has additional roles in promoting the internalization and trafficking of AAV-PHP.eB, it was explored whether AAV-PHP.eB binding and transduction are dependent on known receptor interactions. AAVs typically use a cellular receptor for attachment and secondary receptors for internalization and intracellular trafficking (39); AAV9 utilizes galactose as an attachment factor (40), and, like most AAVs, relies on the AAV receptor (AAVR) for intracellular trafficking and transduction (37). First, it was tested whether LY6A influences AAV-PHP.eB binding to Chinese Hamster ovary (CHO) cells with differing levels of galactose on their surface glycoproteins; Pro5 CHO derivative cells were previously used to map the galactose binding site on the AAV9 capsid (40). The Lec2 and Lec8 models derived from the parental Pro5 CHO cell line were utilized: Lec2 cells expose excess galactose whereas Lec8 cells are unable to add galactose to the glycoproteins (41). AAV9 and AAV-PHP.B similarly bind and transduce Lec2 cells more efficiently than Lec8 or Pro5 cells (FIGS. 4A-4B), showing that AAV-PHP.B also utilizes galactose for cell attachment. In contrast, ectopic Ly6a expression significantly increased binding of AAV-PHP.eB but not AAV9 (FIG. 4B) to Pro5 and Lec8 cells. Ly6a expression did not increase binding of AAV-PHP.eB to Lec2 cells (FIG. 4B), potentially due to the high levels of binding driven by interactions with galactose. Interestingly, Ly6a expression enhanced AAV-PHP.eB transduction of Pro5, Lec2, and Lec8 cells (FIG. 4C). The finding that Ly6a expression renders Lec8 cells as receptive to AAV-PHP.eB transduction as Pro5 cells indicates that LY6A functions as an attachment factor for AAV-PHP.eB independently of galactose. Furthermore, Ly6a expression enhances AAV-PHP.eB transduction of Lec2 cells without increasing binding, suggesting that LY6A mediates internalization and/or trafficking of AAV-PHP.eB.

Figure 4D:
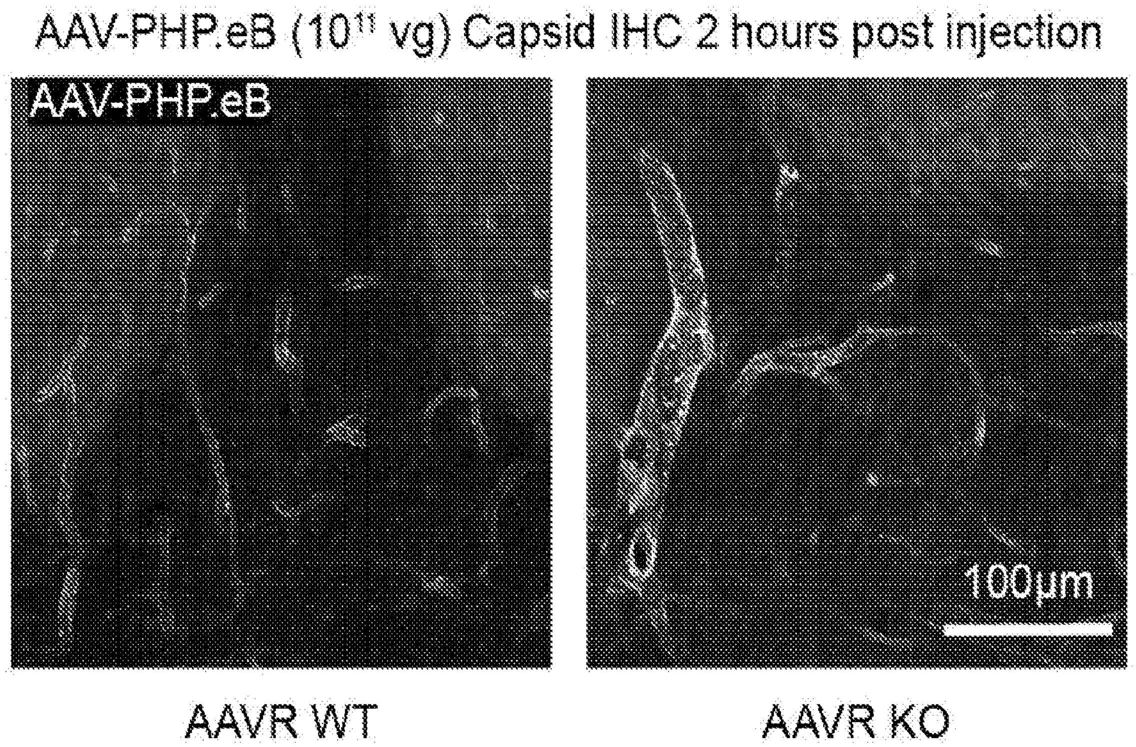
FIG. 4D shows images from AAVR WT or KO mice intravenously injected with AAV-PHP.eB:CAG-NLS-GFP ($10^{11}$ vg/mouse) and brain tissue was assessed via IHC for capsid binding at two hours.
Figure 4E:
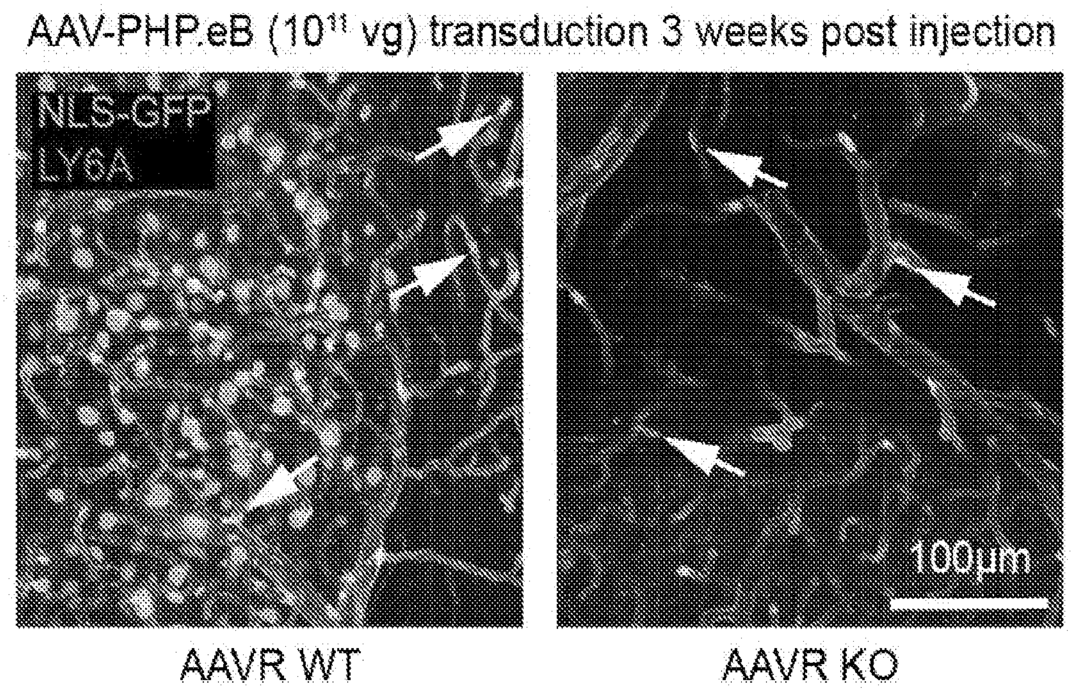
FIG. 4E shows images from AAVR WT or KO mice intravenously injected with AAV-PHP.eB:CAG-NLS-GFP ($10^{11}$ vg/mouse). Brain tissue was assessed via IHC for transduction at three weeks post injection (n=2 per group/per experiment).

However, this process may not require AAVR, which is essential for the intracellular trafficking of numerous AAV capsids including AAV9 (42). To test this possibility, AAVR WT and KO FVB/NJ mice (42) were injected with AAV-PHP.eB, and their brains were collected two hours later for capsid detection. As seen in C57BL/6J mice, AAV-PHP.eB capsids were detected along the vasculature of AAVR KO and control mice (FIG. 4D). AAV-PHP.eB transduction was assessed in a second cohort of AAVR KO and WT mice at three weeks post-administration. AAV-PHP.eB transduction of neurons and astrocytes, which do not express Ly6a, is nearly absent in the brain of AAVR KO mice. In contrast, AAV-PHP.eB transduced Ly6a-expressing endothelial cells throughout the brain (FIG. 4E) in the absence of AAVR.

Example 7: In Vitro Binding Assay for Targeted AAV Variant Discovery

Figure 5A:
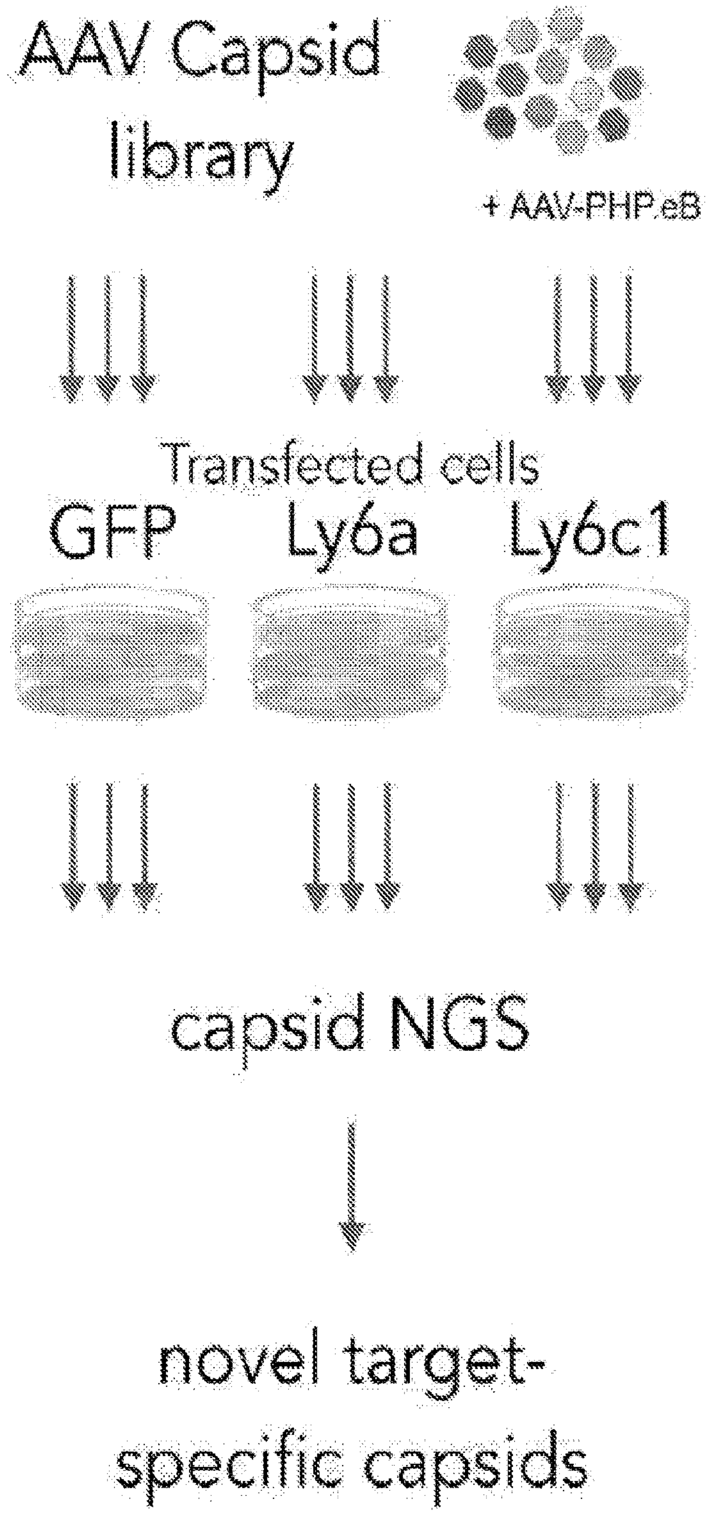
FIG. 5A shows a schematic depiction of a non-limiting example of a screening process described herein.
Figure 5B:
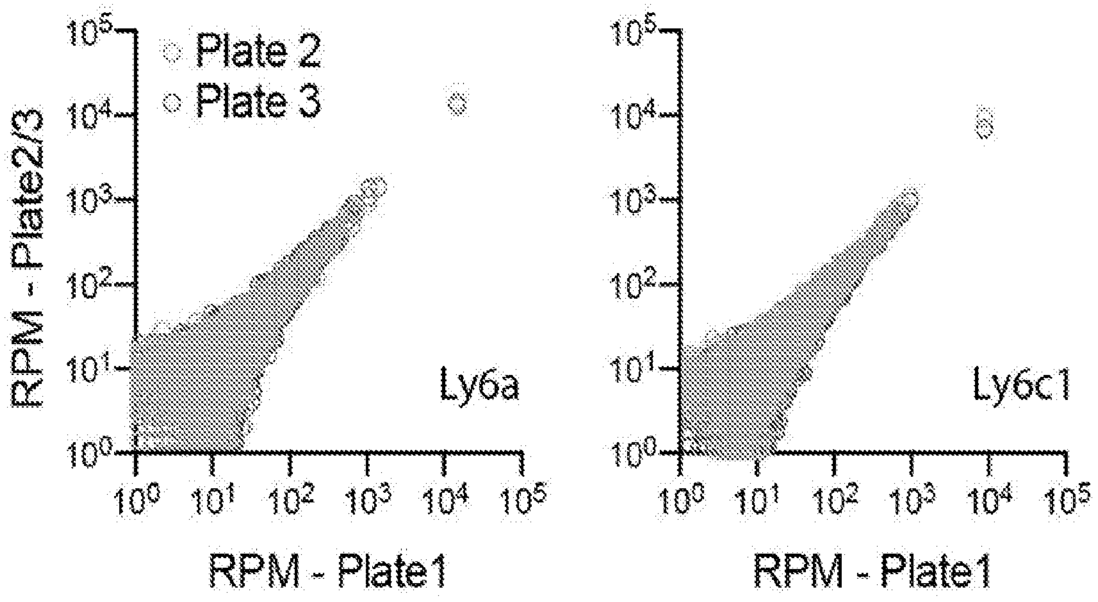
FIG. 5B shows graphs of the reads per million (RPM) correlations between replicates for the 10,000 most highly enriched capsid variants recovered from plates of cells expressing Ly6a (left) or Ly6c1 (right). Three replicates were performed for each assay with replicate 1 RPM plotted on the x-axis and replicate 2 and 3 RPMs plotted on the y-axis.
Figure 5C:
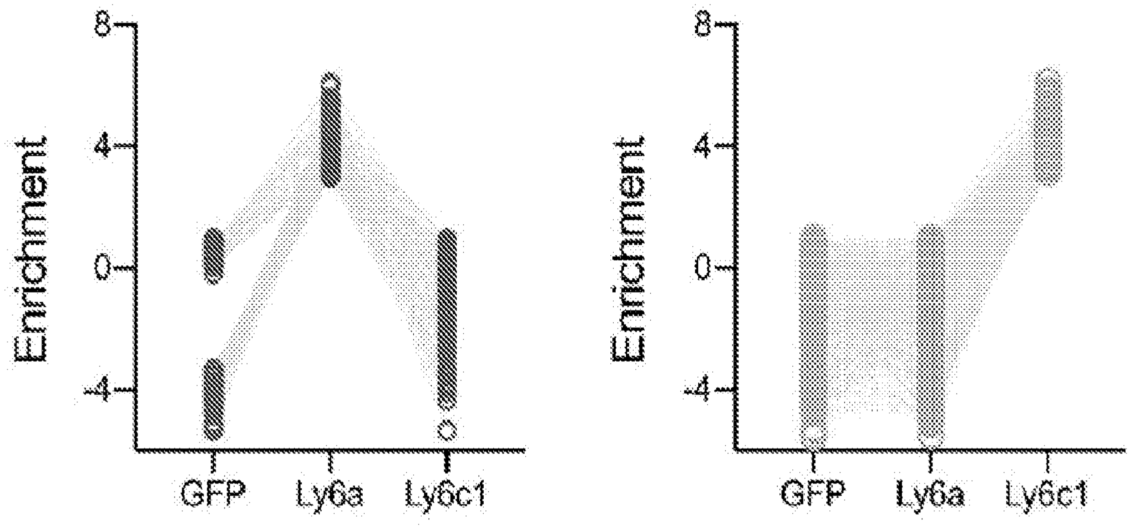
FIG. 5C shows graphs of the average enrichment scores (normalized read counts of the recovered sequence/normalized read count in the starting virus library) (log 2) on each transfected cell type for variants with enrichment scores greater than 3 on Ly6a-expressing (left) or Ly6c1-expressing (right) cells.
Figure 5D:
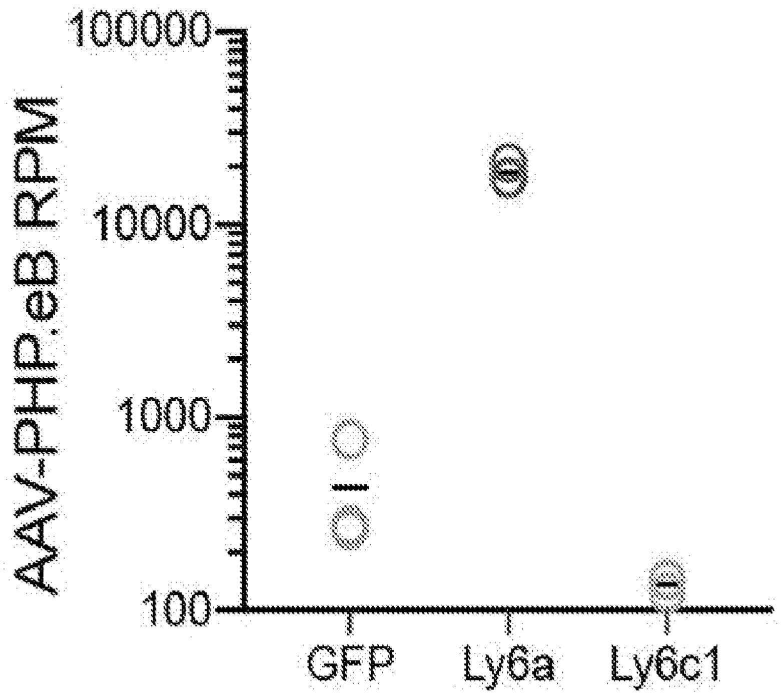
FIG. 5D shows a graph of AAV-PHP.eB that is highly enriched from an AAV library selected by binding to HEK293 cells expressing Ly6a but not cells expressing Ly6c1 or GFP.

The >30-fold increase in AAV-PHP.eB binding and transduction of cells from three different species following ectopic LY6A expression highlighted the potential application of this assay for screening or selecting novel capsids that bind to specific cell surface proteins (FIG. 5A). To test this, HEK293T/17 cells were transfected in triplicate with cDNAs for eGFP, Ly6a, or Ly6c1, and incubated the cells with an AAV9 K449R library (7-mer insertion between amino acids 588 and 589) 24-48 hours post-transfection. The viruses that remained bound to the transfected cells were isolated with TRIzol (Invitrogen) or a DNeasy Blood and Tissue Kit (Qiagen #69504) and analyzed by next generation sequencing (NGS) to quantify the enrichment of peptides that conferred upon the capsid the ability to bind cells expressing the target protein. The recovery of the top 10,000 most enriched capsid sequences bound to Ly6a or Ly6c1 transfected cells was reproducible and quantified based on the tight correlation of reads per million (RPM) between the three replicates (FIG. 5B, Pearson's correlation>0.996 or 0.994, respectively, for all pairwise correlations). Remarkably, using this assay, capsid variants were identified that were selectively enriched on either Ly6a or Ly6c1 expressing cells (FIG. 5C). As a positive control. AAV-PHP.eB was included in the library. AAV-PHP.eB was highly enriched in the screen for capsids that bind to cells transfected with Ly6A but not Ly6c1 or GFP. Furthermore, among capsids selectively enriched on Ly6a-expressing cells, additional sequences were identified that shared partial sequence similarity with AAV-PHP.B and AAV-PHP.B2 (Table 4). A distinct pattern of enriched sequences was detected among those selectively and highly enriched on Ly6c1-expressing cells (Table 5).

Taken together, these results indicate that the in vitro ectopic expression assay can rapidly and quantitatively identify binding interactions between AAV capsids and specific cell surface proteins.

TABLE 4

Sequences (7-mer) with similarity to AAV-PHP.B family peptides that specifically enhance binding to Ly6A expressing cells. The table shows sequences that conform or closely conform to the AAV-PHP.B consensus (T/S)-(L/I/V/M)-(A/x-V/x-P-F-K) (SEQ ID NO: 30225)(top). the AAV-PHP.B2 consensus (S/T)-(V/x)-(S/T/x)-(K/R)-P-F-(L/I/V/A) (SEQ ID NO: 30226) (middle), or x-x-x-F-K-(D/N)-(I/V/P) (SEQ ID NO: 30227), where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| Sequences with similarity to PHP.B (TLAVPFK) (SED ID NO: 30258) | | | | | |
|---|---|---|---|---|---|
| 7-mer | SEQ ID NO: | Nucleotide sequence | SEQ ID NO: | Ly6A | Ly6c1 |
| VAER**PFK** | 20 | GTGGCTGAGCGTCCTTTTAAG | 34 | 6.38 | 1.22 |
| **T**VMA**PFK** | 21 | ACGGTGATGGCGCCGTTTAAG | 35 | 5.53 | -0.19 |
| YVGN**PFK** | 22 | TATGTGGGGAATCCTTTTAAG | 36 | 4.53 | 0.58 |
| DMER**PFK** | 23 | GATATGGAGCGTCCGTTTAAG | 37 | 4.51 | -3.91 |
| R**I**DN**PFK** | 24 | AGGATTGATAATCCTTTTAAG | 38 | 4.48 | -1.89 |
| **T**RDL**PFK** | 25 | ACGAGGGATCTGCCTTTTAAG | 39 | 4.34 | -1.36 |
| ALHV**PFK** | 26 | GCTTTGCATGTTCCTTTTAAG | 40 | 4.11 | 0.26 |
| **TLA**Y**PFK** | 27 | ACGCTGGCGTATCCGTTTAAG | 41 | 3.93 | -0.72 |
| GVDR**PFK** | 28 | GGTGTTGATCGGCCGTTTAAG | 42 | 3.84 | -1.13 |
| **SL**TT**PFK** | 29 | AGTTTGACGACGCCGTTTAAG | 43 | 3.18 | -1.85 |
| ESTR**PFK** | 30 | GAGTCTACTAGGCCGTTTAAG | 44 | 2.87 | 0.28 |
| GDNR**PFK** | 31 | GGGGATAATAGGCCGTTTAAG | 45 | 2.65 | 0.57 |
| AISA**PFK** | 32 | GCTATTAGTGCGCCTTTTAAG | 46 | 2.56 | -0.06 |
| **T**GTS**PFK** | 33 | ACTGGGACTTCGCCGTTTAAG | 47 | 2.22 | -3.32 |
| Seq. with similarity to PHP.B2 (SVSKPFL) (SEQ ID NO: 1906) (S/T)-(V/L/I)-x-(K/R)-P-F-(L/I/V/A) (SEQ ID NO: 30226) | | | | | |
| 7-mer | SEQ ID NO: | Nucleotide sequence | SEQ ID NO: | Ly6A | Ly6c1 |
| **S**ND**RPFI** | 48 | AGTAATGATCGTCCTTTTATT | 78 | 5.43 | -1.02 |
| **S**HT**KPFA** | 49 | AGTCATACGAAGCCGTTTGCT | 79 | 4.79 | 0.97 |
| **SI**N**KPFV** | 50 | TCGATTAATAAGCCTTTTGTT | 80 | 4.74 | -0.30 |
| DKQ**KPFL** | 51 | GATAAGCAGAAGCCGTTTCTG | 81 | 4.60 | 0.94 |
| MMA**KPFL** | 52 | ATGATGGCTAAGCCTTTTCTT | 82 | 4.53 | -0.49 |
| NER**RPFL** | 53 | AATGAGCGTAGGCCTTTTCTG | 83 | 4.31 | 0.77 |

TABLE 4-continued

Sequences (7-mer) with similarity to AAV-PHP.B family peptides that specifically enhance binding to Ly6A expressing cells. The table shows sequences that conform or closely conform to the AAV-PHP.B consensus (T/S)-(L/I/V/M)-(A/x-V/x-P-F-K) (SEQ ID NO: 30225)(top). the AAV-PHP.B2 consensus (S/T)-(V/x)-(S/T/x)-(K/R)-P-F-(L/I/V/A) (SEQ ID NO: 30226) (middle), or x-x-x-F-K-(D/N)-(I/V/P) (SEQ ID NO: 30227), where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| | | | | | |
|---|---|---|---|---|---|
| TDTRPFI | 54 | ACTGATACTAGGCCTTTTATT | 84 | 4.19 | -3.32 |
| SQKTPFL | 55 | AGTCAGAAGACTCCGTTTCTG | 85 | 3.81 | -3.55 |
| GSERPFL | 56 | GGTTCTGAGAGGCCGTTTTTG | 86 | 3.78 | -4.20 |
| TSMKPFL | 57 | ACGAGTATGAAGCCTTTTCTG | 87 | 3.49 | -0.98 |
| GESRPFI | 58 | GGTGAGTCTCGTCCTTTTATT | 88 | 3.32 | -2.08 |
| NDQRPFL | 59 | AATGATCAGCGGCCTTTTCTG | 89 | 3.27 | -4.33 |
| AADRPFL | 60 | GCTGCTGATCGTCCGTTTCTG | 90 | 2.73 | -3.32 |
| DSQRPFI | 61 | GATAGTCAGCGTCCGTTTATT | 91 | 2.63 | -3.55 |
| ALAKPFI | 62 | GCTCTTGCTAAGCCTTTTATT | 92 | 1.91 | -0.19 |
| SEGRPFI | 63 | TCGGAGGGGAGGCCTTTTATT | 93 | 1.85 | -3.55 |
| ASSKPFL | 64 | GCGTCTAGTAAGCCGTTTCTT | 94 | 3.90 | 1.19 |
| SIARPFV | 65 | AGTATTGCTCGTCCGTTTGTG | 95 | 3.79 | -3.55 |
| NIIRPFA | 66 | AATATTATTCGGCCTTTTGCT | 96 | 3.23 | 0.40 |
| ESSKPFR | 67 | GAGAGTAGTAAGCCGTTTCGT | 97 | 3.15 | 1.28 |
| TSFKPFP | 68 | ACTTCTTTTAAGCCGTTTCCT | 98 | 3.11 | 0.48 |
| NMERPFR | 69 | AATATGGAGCGGCCGTTTAGG | 99 | 2.96 | 0.95 |
| TTMKPFN | 70 | ACGACGATGAAGCCTTTTAAT | 100 | 2.95 | -3.74 |
| NLKRPFA | 71 | AATTTGAAGAGGCCGTTTGCT | 101 | 2.80 | 0.85 |
| SVSKPFS | 72 | AGTGTGTCGAAGCCTTTTAGT | 102 | 2.73 | -1.53 |
| SSEKPFQ | 73 | AGTTCGGAGAAGCCGTTTCAG | 103 | 2.69 | -3.55 |
| TKSTPFI | 74 | ACTAAGTCGACTCCGTTTATT | 104 | 2.60 | -1.85 |
| YENRPFV | 75 | TATGAGAATCGTCCTTTTGTG | 105 | 2.23 | -3.32 |
| SLSKPFS | 76 | AGTTTGTCGAAGCCGTTTTCT | 106 | 2.19 | -2.08 |
| QNARPFV | 77 | CAGAATGCTCGTCCGTTTGTG | 107 | 1.52 | 1.42 |
| Sequences related to the consensus x-x-x-F-K-(D/N)-(I/V/P)(SEQ ID NO: 30227) | | | | | |
| 7-mer | SEQ ID NO: | Nucleotide sequence | SEQ ID NO: | Ly6A | Ly6c1 |
| TITFKDV | 108 | ACTATTACGTTTAAGGATGTT | 120 | 5.15 | -0.78 |
| SLDFKNI | 109 | AGTCTTGATTTTAAGAATATT | 121 | 4.61 | -1.29 |
| VAVFKNV | 110 | GTGGCTGTGTTTAAGAATGTG | 122 | 4.23 | -0.91 |
| AGSFKDI | 111 | GCTGGTTCGTTTAAGGATATT | 123 | 3.96 | -2.87 |
| PPSFKNV | 112 | CCTCCGAGTTTTAAGAATGTG | 124 | 3.69 | -4.33 |
| RSDFKDI | 113 | CGGAGTGATTTTAAGGATATT | 125 | 3.45 | -2.44 |
| STTFKDI | 114 | AGTACTACTTTTAAGGATATT | 126 | 3.44 | -3.32 |
| KDKFKDI | 115 | AAGGATAAGTTTAAGGATATT | 127 | 3.38 | -2.08 |
| QTLFKNI | 116 | CAGACGTTGTTTAAGAATATT | 128 | 3.07 | -0.72 |

TABLE 4-continued

Sequences (7-mer) with similarity to AAV-PHP.B family peptides that specifically enhance binding to Ly6A expressing cells. The table shows sequences that conform or closely conform to the AAV-PHP.B consensus (T/S)-(L/I/V/M)-(A/x-V/x-P-F-K) (SEQ ID NO: 30225)(top). the AAV-PHP.B2 consensus (S/T)-(V/x)-(S/T/x)-(K/R)-P-F-(L/I/V/A) (SEQ ID NO: 30226) (middle), or x-x-x-F-K-(D/N)-(I/V/P) (SEQ ID NO: 30227), where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| | | | | | |
|---|---|---|---|---|---|
| RLS**FKDV** | 117 | CGGCTTAGTTTTAAGGATGTG | 129 | 2.39 | -1.62 |
| HNV**FKNP** | 118 | CATAATGTGTTTAAGAATCCT | 130 | 2.09 | 0.33 |
| KTQ**FKDV** | 119 | AAGACGCAGTTTAAGGATGTG | 131 | 2.09 | -3.55 |

TABLE 5

Sequences (7-mer) with the consensus x-(K/R/Y)-(x/R/K/Y/F)-(G/Y/K/R/x)-(Y/W/F/L/M)-(S/A)-(S/T/A/Q) (SEQ ID NO: 30228) are enriched on cells expressing Ly6c1. The table lists example 7-mer peptides that match closely match the above consensus sequence, where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| 7-mer | SEQ ID NO: | Nucleotide sequence | SEQ ID NO: | Ly6A | Ly6c1 |
|---|---|---|---|---|---|
| V**R**P**GWST** | 132 | GTGCGTCCGGGGTGGTCGACG | 219 | 1.02 | 5.89 |
| TQQ**GYSS** | 133 | ACTCAGCAGGGGTATAGTTCT | 220 | -0.92 | 5.80 |
| **TK**S**GYST** | 134 | ACGAAGTCTGGTTATAGTACT | 221 | 0.68 | 5.71 |
| **TR**N**GYST** | 135 | ACTCGTAATGGTTATAGTACG | 222 | 0.82 | 5.58 |
| ID**RGYS**V | 136 | ATTGATCGGGGTTATAGTGTG | 223 | -1.04 | 5.30 |
| P**Y**Q**GASS** | 137 | CCTTATCAGGGGGCGAGTAGT | 224 | -0.53 | 5.24 |
| S**Y**Q**GYSS** | 138 | AGTTATCAGGGTTATAGTAGT | 225 | 1.47 | 5.21 |
| VN**RGYSS** | 139 | GTGAATCGTGGGTATAGTTCG | 226 | 0.89 | 5.18 |
| L**R**TA**YSS** | 140 | CTTAGGACGGCTTATAGTAGT | 227 | 1.13 | 5.12 |
| SYI**GASS** | 141 | AGTTATATTGGGGCGTCGAGT | 228 | -1.01 | 5.08 |
| NG**YKGST** | 142 | AATGGTTATAAGGGTTCGACG | 229 | 1.24 | 4.98 |
| EI**RGYSS** | 143 | GAGATTAGGGGGTATTCTAGT | 230 | 0.75 | 4.92 |
| DV**KYGSS** | 144 | GATGTGAAGTATGGGTCTTCG | 231 | -0.36 | 4.92 |
| GG**RG**L**SS** | 145 | GGGGGGAGGGGGCTTTCTAGT | 232 | 2.00 | 4.90 |
| **FR**I**GGSS** | 146 | TTTAGGATTGGTGGTTCTAGT | 233 | 1.34 | 4.89 |
| L**KYG**T**ST** | 147 | TTGAAGTATGGTACGTCTACG | 234 | 1.24 | 4.88 |
| KQ**Y**Q**GST** | 148 | AAGCAGTATCAGGGGTCTACT | 235 | 1.54 | 4.88 |
| N**Y**T**GYSS** | 149 | AATTATACTGGTTATTCTTCT | 236 | 0.44 | 4.83 |
| RAT**GYSS** | 150 | CGTGCTACTGGGTATTCTTCG | 237 | 2.49 | 4.75 |
| ES**RGFSS** | 151 | GAGAGTAGGGGTTTTAGTTCT | 238 | -0.58 | 4.70 |
| QH**F**GQ**SS** | 152 | CAGCATTTTGGTCAGAGTTCT | 239 | -0.37 | 4.68 |
| **TR**T**GYST** | 153 | ACGAGGACGGGTTATAGTACG | 240 | 0.89 | 4.63 |
| A**K**A**GYAS** | 154 | GCGAAGGCGGGTTATGCTAGT | 241 | -0.03 | 4.54 |
| N**R**G**GYAS** | 155 | AATAGGGGGGGGTATGCTAGT | 242 | -0.18 | 4.53 |
| SI**Y**L**GSQ** | 156 | AGTATTTATCTGGGTTCTCAG | 243 | -0.76 | 4.47 |

TABLE 5-continued

Sequences (7-mer) with the consensus x-(K/R/Y)-(x/R/K/Y/F)-(G/Y/K/R/x)-(Y/W/F/L/M)-(S/A)-(S/T/A/Q) (SEQ ID NO: 30228) are enriched on cells expressing Ly6c1. The table lists example 7-mer peptides that match closely match the above consensus sequence, where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| | | | | | |
|---|---|---|---|---|---|
| YLKGYSA | 157 | TATCTTAAGGGGTATAGTGCT | 244 | 0.15 | 4.46 |
| EKKQYSS | 158 | GAGAAGAAGCAGTATAGTAGT | 245 | 0.89 | 4.45 |
| NYTGYSS | 159 | AATTATACTGGGTATTCTTCT | 246 | -0.46 | 4.44 |
| SKTGYST | 160 | TCTAAGACGGGTTATAGTACG | 247 | -3.55 | 4.43 |
| TEKWTSS | 161 | ACTGAGAAGTGGACGTCGAGT | 248 | 0.98 | 4.43 |
| DRIHGYS | 162 | GATCGGATTCATGGTTATAGT | 249 | -0.11 | 4.34 |
| TRFGAST | 163 | ACTCGTTTTGGTGCTAGTACT | 250 | 0.00 | 4.32 |
| GKHFSST | 164 | GGGAAGCATTTTAGTTCGACG | 251 | 2.64 | 4.25 |
| TKYMHSS | 165 | ACTAAGTATATGCATAGTTCG | 252 | 1.35 | 4.24 |
| VKVGFSS | 166 | GTTAAGGTTGGTTTTTCGTCG | 253 | -2.25 | 4.22 |
| LRMGASS | 167 | CTGAGGATGGGGGCGTCTTCT | 254 | 0.91 | 4.17 |
| LNRGSST | 168 | TTGAATCGGGGTAGTTCTACG | 255 | 1.72 | 4.15 |
| LYAGRSS | 169 | CTTTATGCGGGTCGGAGTTCG | 256 | 1.03 | 4.13 |
| DTKWSSS | 170 | GATACTAAGTGGAGTAGTAGT | 257 | 0.53 | 4.11 |
| SSTGYSS | 171 | TCGTCTACTGGTTATAGTAGT | 258 | -1.93 | 4.00 |
| MRTFGSA | 172 | ATGCGTACGTTTGGTAGTGCG | 259 | 1.00 | 3.97 |
| LAHTYSS | 173 | CTGGCTCATACTTATAGTTCG | 260 | 0.04 | 3.97 |
| LTKWEST | 174 | CTTACTAAGTGGGAGAGTACT | 261 | 0.82 | 3.91 |
| LWAKGST | 175 | TTGTGGGCGAAGGGTAGTACG | 262 | 1.42 | 3.90 |
| GKTHGYS | 176 | GGTAAGACGCATGGTTATTCG | 263 | 1.65 | 3.87 |
| MRTLMSS | 177 | ATGCGGACGCTTATGTCGTCT | 264 | -0.52 | 3.85 |
| TRTSGAS | 178 | ACGAGGACGAGTGGTGCGTCG | 265 | 0.43 | 3.85 |
| MERYGSS | 179 | ATGGAGCGTTATGGGAGTTCT | 266 | -2.28 | 3.83 |
| TYKSGSS | 180 | ACGTATAAGTCGGGTTCGAGT | 267 | 1.95 | 3.78 |
| TRFGSST | 181 | ACTAGGTTTGGTAGTTCGACT | 268 | 1.29 | 3.63 |
| DKAWGST | 182 | GATAAGGCTTGGGGGTCGACT | 269 | 0.19 | 3.56 |
| VPRYGSS | 183 | GTTCCGCGTTATGGTTCGAGT | 270 | -1.01 | 3.55 |
| LSKGLSS | 184 | CTTAGTAAGGGTCTTTCGAGT | 271 | -3.55 | 3.55 |
| STRGYSA | 185 | AGTACTAGGGGGTATAGTGCT | 272 | 1.08 | 3.55 |
| IRVGYST | 186 | ATTAGGGTGGGGTATTCTACT | 273 | -3.55 | 3.46 |
| GNENFSS | 187 | GGTAATTTTAATTTTAGTTCT | 274 | -1.43 | 3.45 |
| DKYNFSS | 188 | GATAAGTATAATTTTAGTAGT | 275 | -0.13 | 3.43 |
| EDHRYSS | 189 | GAGGATCATCGGTATAGTAGT | 276 | 0.17 | 3.40 |
| VKGGYSS | 190 | GTGAAGGGGGGTTATTCTAGT | 277 | 0.07 | 3.30 |
| VTHGYSS | 191 | GTTACTCATGGTTATAGTAGT | 278 | -0.84 | 3.25 |
| MVRNYST | 192 | ATGGTGAGGAATTATTCGACT | 279 | -0.94 | 3.25 |
| HKTHYSS | 193 | CATAAGACGCATTATTCTAGT | 280 | 0.86 | 3.24 |

TABLE 5-continued

Sequences (7-mer) with the consensus x-(K/R/Y)-(x/R/K/Y/F)-(G/Y/K/R/x)-(Y/W/F/L/M)-(S/A)-(S/T/A/Q) (SEQ ID NO: 30228) are enriched on cells expressing Ly6c1. The table lists example 7-mer peptides that match closely match the above consensus sequence, where x is any amino acid. AA that match the consensus are shown in bold. The Ly6A and Ly6c1 columns provide the fold enrichment (log2) for each sequence following screening on Ly6a- or Ly6c1-transfected cells relative to the abundance in the prescreened virus library.

| | | | | | |
|---|---|---|---|---|---|
| IV**RGLSS** | 194 | ATTGTTCGTGGTCTGAGTTCG | 281 | -1.14 | 3.24 |
| TVT**GYSS** | 195 | ACTGTTACGGGTTATTCGTCT | 282 | -3.91 | 3.22 |
| NKV**GYST** | 196 | AATAAGGTGGGGTATTCTACG | 283 | -3.74 | 3.13 |
| NSP**GWSS** | 197 | AATAGTCCGGGTTGGTCGAGT | 284 | -0.93 | 3.08 |
| HEHR**YST** | 198 | CATGAGCATAGGTATAGTACT | 285 | -4.06 | 3.06 |
| LSM**GYST** | 199 | CTGTCTATGGGGTATAGTACT | 286 | -3.91 | 2.97 |
| LL**RGASS** | 200 | CTTTTGCGTGGTGCGAGTTCT | 287 | -0.33 | 2.96 |
| LKK**GYST** | 201 | TTGAAGAAGGGGTATAGTACT | 288 | 1.72 | 2.96 |
| **GKTGYST** | 202 | GGGAAGACTGGGTATTCGACG | 289 | -3.32 | 2.93 |
| W**RQGYAS** | 203 | TGGAGGCAGGGGTATGCGAGT | 290 | -0.09 | 2.89 |
| L**RGGYST** | 204 | TTGAGGGGTGGGTATAGTACG | 291 | -3.32 | 2.88 |
| D**RKGYSA** | 205 | GATCGTAAGGGGTATAGTGCT | 292 | -0.39 | 2.77 |
| LKT**GMSS** | 206 | TTGAAGACGGGGATGTCTAGT | 293 | -0.66 | 2.74 |
| SKGS**YST** | 207 | TCTAAGGGGAGTTATAGTACT | 294 | 1.54 | 2.74 |
| I**RQGYSS** | 208 | ATTCGTCAGGGGTATTCGAGT | 295 | -1.28 | 2.61 |
| QD**KGYSS** | 209 | CAGGATAAGGGTTATAGTTCG | 296 | -3.55 | 2.61 |
| QSA**GYST** | 210 | CAGTCGGCTGGGTATTCTACG | 297 | -1.58 | 2.55 |
| **FLPGYSS** | 211 | TTTCTGCCGGGGTATTCGTCG | 298 | -2.29 | 2.54 |
| GS**YGYSS** | 212 | GGGAGTTATGGTTATTCGTCG | 299 | -3.32 | 2.48 |
| MNI**GYSA** | 213 | ATGAATATTGGGTATAGTGCG | 300 | -1.48 | 2.40 |
| HTQ**GYST** | 214 | CATACGCAGGGGTATAGTACG | 301 | -3.32 | 2.26 |
| V**YPGYST** | 215 | GTTTATCCTGGTTATAGTACG | 302 | -3.32 | 2.21 |
| IAT**GYSQ** | 216 | ATTGCTACTGGTTATAGTCAG | 303 | -3.74 | 2.18 |
| SKS**GYSA** | 218 | TCTAAGAGTGGTTATAGTGCG | 304 | -3.32 | 2.14 |
| **TYGGYSQ** | 218 | ACGTATGGGGGTTATTCTCAG | 305 | -0.34 | 2.02 |

Example 8: Novel AAVs that Interact with Ly6a and Ly6c are Enriched in a High-Throughput In Vivo Screening Assay for AAVs that Express the Capsid Transgene To validate and test 7-mer modified AAV vectors that selectively bind HEK293T cells that express Ly6a, Ly6c1, marmoset CD59, or human CD59, a new synthetic oligo pool library was generated. The oligo pool (Agilent) library comprised 7-mer-modified AAV variants that were specifically enriched on HEK293T expressing one of the above genes. In addition, in cases where motifs were found within the enriched sequences, 7-mers that maintained the motif but introduced diversity adjacent to the motif were also generated. For example, X-(K/R)-(A/D/E/F/G/H/I/L/M/N/P/Q/S/T/V/W/Y)-G-Y-S-(Q/S/T) (SEQ ID NO: 30259) was generated, where X is any amino acid, based on a common motif identified through screening for 7-mer modified capsids that were selectively enriched on HEK293T cells expressing Ly6c1. Single site-saturation mutagenesis was also used to explore which amino acids within the 7-mer are critical for the selected activity of several highly enriched sequences that did not share an obvious motif with other enriched sequences. Sequences were pooled into a single oligo pool library along with several reference sequences with characterized tropisms (e.g., AAV-PHP.B2: SVSKPFL (SEQ ID NO: 1906); AAV-PHP.B3: FTLTTPK (SEQ ID NO: 1908); AAV-PHP.A: YTLSQGW (SEQ ID NO: 10689). Two copies of each 7-mer were synthesized using different codon sets. The library contained just under 60,000 unique oligos.

Figure 2C:
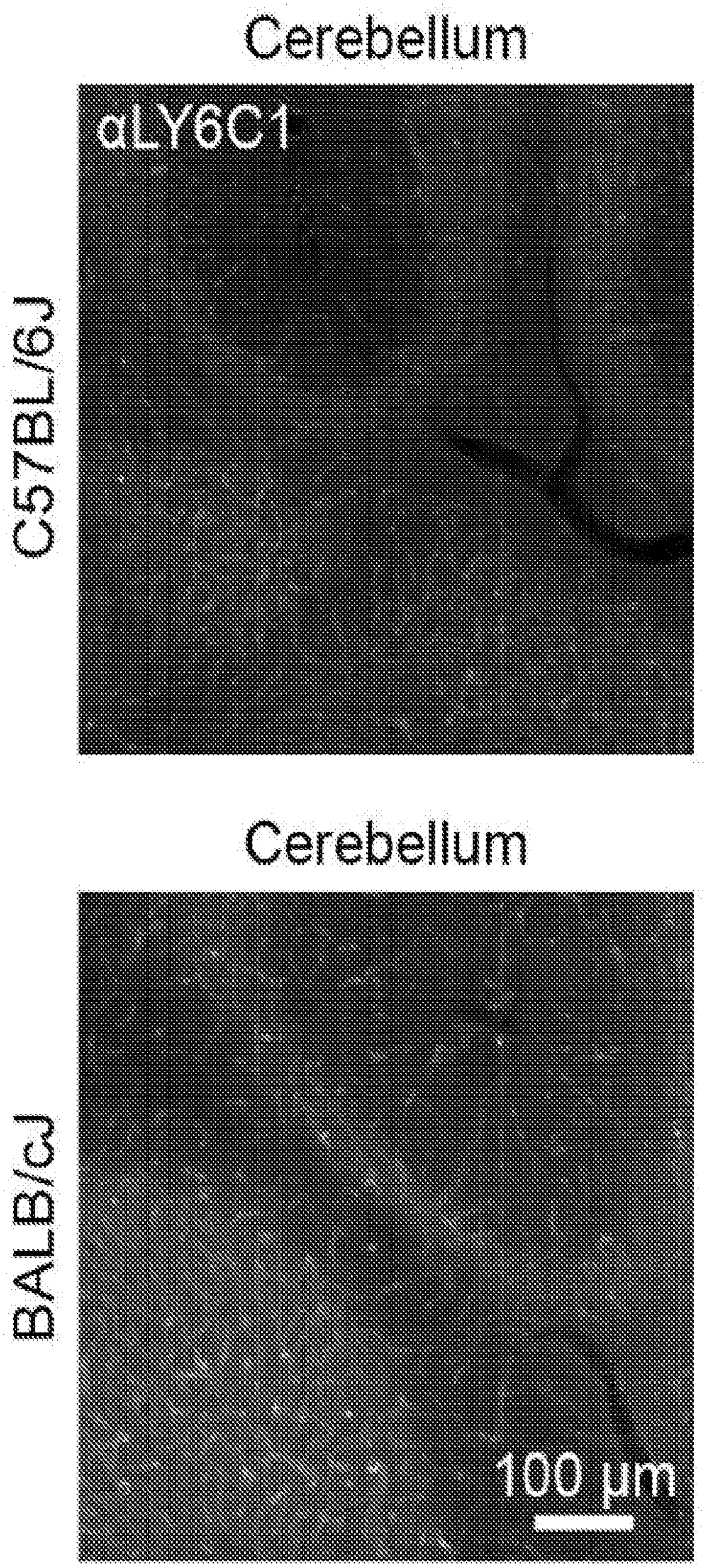
FIG. 2C shows images of whole sagittal LY6A IHC in C57BL/6J (top) or BALB/cJ (bottom) mice.
Figure 2D:
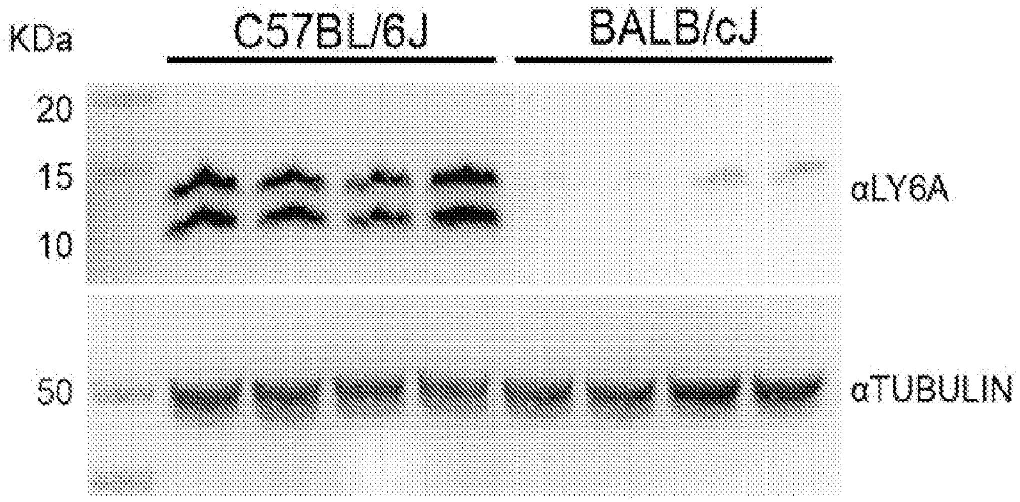
FIG. 2D shows a western blot of LY6A and αTubulin (αTUB) control from forebrain lysates providing LY6A abundance and protein states in each mouse line.
Figure 5E:
FIG. 5E shows images of the indicated AAV variants screened for binding to LY6C1 in vitro packaged into an ssAAV-CAG-NLS-GFP reporter vector and delivered to adult C57BL/6J (top row) or BALB/cJ (bottom row) at $10^{11}$ vg/animal. Transduction was assessed two weeks later.
Figure 13:
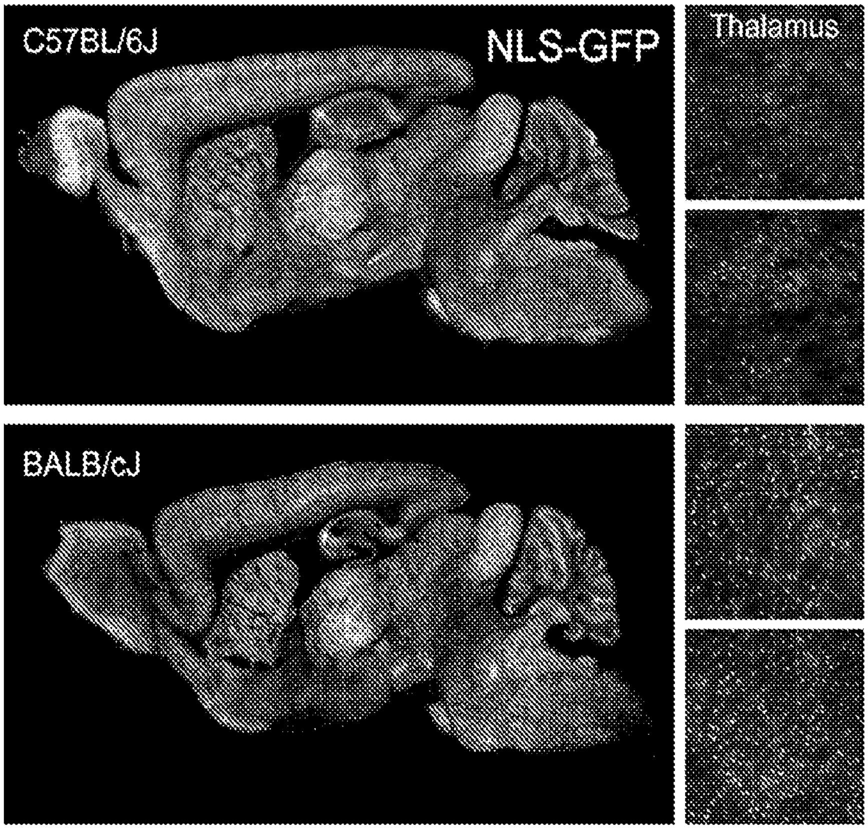
FIG. 13 shows images of GFP fluorescence in whole brain sagittal sections from C57BL/6J (top) or BALB/cJ (bottom), ten days after intravenous injection of AAV-BI28:CAG-NLS-GFP-W-pA $1\times10^{12}$ vg/mouse to 6-week-old mice. Images on the right show NLS-GFP expression in the thalamus in two replicate animals.
Figure 14:
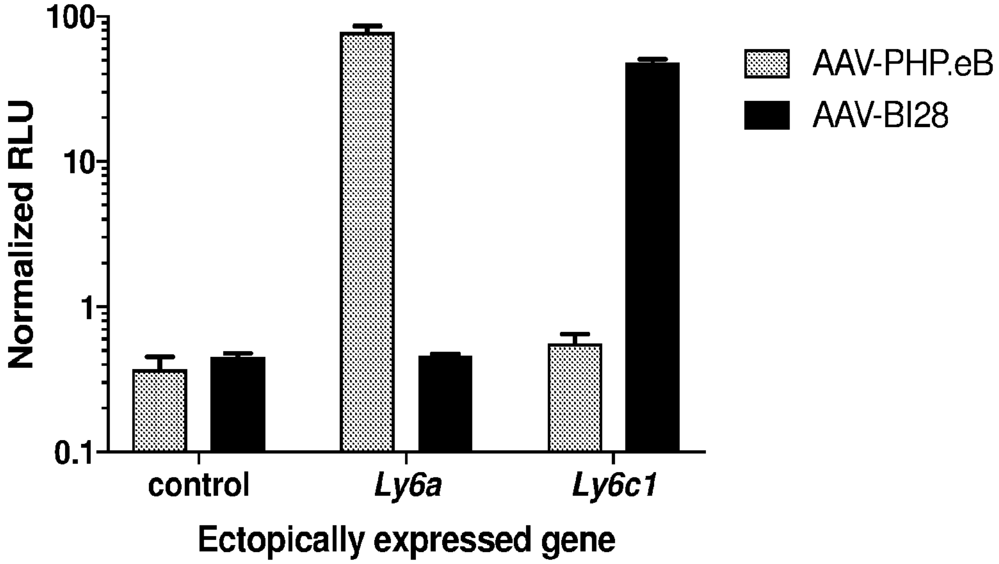
FIG. 14 is a graph showing ectopic expression of Ly6a or Ly6c1 sensitizes human brain endothelial cells to transduction by AAV-PHP.eB and AAV-BI-28, respectively. Human brain endothelial cells (hCMEC/D3) were transduced in triplicate with no virus (untransduced control), a control AAV (AAV-CAG-NLS-mScarlet), a virus encoding mouse Ly6a (AAV-CAG-Ly6a), or a virus encoding mouse Ly6c1 (AAV-CAG-Ly6c1). Viruses were delivered at $10^5$ vg/cell. Two days later, the cells were transduced with either a LY6A-specific virus (AAV-PHP.eB:CAG-GFP-2A-Luc) or a LY6C1-specific virus (AAV-BI28). 24 hours later, transduction was assessed by a firefly luciferase assay using Britelite plus kit as directed by the manufacturer (PerkinElmer). AAV-PHP.eB and AAV-BI28 were delivered at $10^4$ vg/cell.

The oligo pool was used to generate a PCR fragment that was cloned (as described in Deverman et al NBT 2016) into a novel AAV capsid selection plasmid. This AAV genome provides selective pressure for functional AAV variants (i.e., those that transcribe the viral capsid gene in vivo). In between the CMV enhancer and AAV p41 promoter contains a synthetic intron with a consensus donor motif (CAGGTAAGT), consensus splice motif (TTTTTTCTA-CAGGT) and branch point sequence. This library vector comprises a CMV enhancer upstream of the AAV p41 promoter and Cap gene. The AAV-capsid library expresses the AAV capsid gene both during virus production as well as following transduction in cultured cells and in vivo. To recover the functional capsids, cellular/tissue RNA was isolated, the capsid RNA was reverse transcribed into cDNA, and the capsid sequence containing the 7-mer was amplified by PCR. By recovering and sequencing viral RNAs, this approach applied selective pressure for functional, transcriptionally active AAV vectors.

transduction phenotype, unlike Ly6A, it remains highly expressed on endothelial cells of non-permissive strains (FIG. 2C). Therefore, the question of whether AAV capsids engineered to bind LY6C1 could transduce cells within the mouse CNS was investigated. GFP reporter viruses were generated that were packaged in five of the LY6C1-binding AAV variants and one control variant that was selected for enhanced binding to HEK293 cells. Remarkably, four of the five in vitro screened variants displayed either endothelial cell transduction and/or transduction of neurons and glia throughout the CNS of both C57BL/6J and BALB/cJ mice; in contrast, only sparse transduction was seen with the control variant (FIG. 5E; Table 6). The most potent of these variants, AAV-BI-28 is highly effective at crossing the BBB in both strains of mice (FIG. 13).

TABLE 6

Characteristics of AAV capsids comprising 7-mer sequences screened on Ly6c1 expressing cells in vivo.

| Variant | 7-mer | SEQ ID NO: | Nucleotide sequence | SEQ ID NO: | Ly6A | Ly6c | C57BL/6J | BALB/cJ | Characteristics |
|---|---|---|---|---|---|---|---|---|---|
| C1 | KSAGSIY | 306 | AAGAGTGCTGGTTCGATTTAT | 311 | 1.41 | 6.12 | ++ | + | Increased transcytosis |
| C2 | TQQGYSS | 307 | ACTCAGCAGGGGTATAGTTCT | 312 | -0.92 | 5.8 | ++++ | ++++ | Strongly increased transcytosis |
| C3 | WGTPPRG | 308 | TGGGGGACGCCTCCGAGGGGG | 313 | 1.01 | 6.35 | ++++ | + | Mostly endothelial |
| C5 | ELYKLPT | 309 | GAGCTGTATAAGCTTCCGACG | 314 | -2.26 | 5.38 | +++ | +++ | Increased transcytosis and regional variation |
| C6 | TRNGYST | 310 | ACTCGTAATGGTTATAGTACG | 315 | 0.186 | 4.05 | + | + | — |
| C28 | KSVGSVY | 10669 | AAGTCAGTAGGCTCAGTATAC | 11564 | -1.24 | 3.59 | +++++ | +++++ | Strongly increased transcytosis |

An AAV library was generated from this oligo pool library and delivered it intravenously to two C57BL/6J and two BALB/cJ mice. It was found that more than 100 of the sequences screened on Ly6a or Ly6c1 expressing cells (or sequences derived from those sequences as described above) that were enriched in at least one of the CNS RNA samples. Furthermore, the sequences that were found to bind Ly6a expressing cells were selectively enriched in the CNS of C57BL/6J mice while many of the sequences found to bind Ly6c1 expressing cells were enriched in both C57BL/6J and BALB/cJ mice. This differential tropism is consistent with the finding that genetic changes in the BALB/cJ Ly6a gene prevent it from functioning as a receptor for AAV capsids engineered to bind Ly6a (Huang et al, bioRxiv 2019). These data provide additional validation that a significant fraction of the 7-mer modified capsids that were screened for selective binding to HEK293T cells ectopically expressing Ly6a or Ly6c exhibited the predicted enhanced tropism in vivo.

Example 9: Novel AAV Capsids Screened on Ly6c1-Expressing Cells In Vitro Transduce or Transcytose the Mouse Brain Endothelium Although SNPs in Ly6c1 identified this gene as a potential factor associated with the nonpermissive AAV-PHP.eB These results demonstrate several findings. First, like LY6A, LY6C1 has the ability to traffic engineered viruses into the CNS, raising the possibility that additional Ly6 proteins and the wider class of GPI-anchored proteins may also facilitate CNS-wide gene delivery in other species including humans. Second, the novel ectopic expression and in vitro binding assay developed herein can enable the development of multiple AAV capsid variants that bind to specific proteins. Third, protein targets known to be present on specific cell populations of interest (e.g., brain endothelial cells) can be harnessed to enhance the transduction of those cells in vivo. This assay could enable the rapid development of capsids that are able to transduce target cell populations more efficiently and with greater specificity. Importantly, because the precise target receptor is known, the method and findings will be more translational to human gene therapy as compared to existing capsid engineering methods that rely on in vivo selections in model organisms and often result in the development of AAV capsids with species-specific tropisms.

Example 10: Purified Fc-Fusion Proteins can be Used to Identify Novel AAV Capsids that Bind to Specific Receptors To identify AAV capsids that selectively bind specific LY6 proteins, a purified protein pull down assay was used. To do this, a screen for viruses that interact with purified LY6A-, LY6C- or human CD59-fusion proteins was performed. This assay proved highly sensitive and resulted in the development of thousands of 7-mer modified capsid variants that selectively bind LY6A-Fc or LY6C1-Fc, but not a control Fc protein (Tables 11 and 15). A smaller number of sequences was found to specifically bind hCD59-Fc (Table 18). Encouragingly, for all three LY6-Fc fusions, a significant number of novel sequences were identified that matched motifs previously identified through HEK293T cell ectopic receptor assays and in vivo screening for each receptor (LY6A: Table 12; LY6C1: Table 16; hCD59: Table 18).

Example 11: Ectopic Expression of Ly6a or Ly6c1 can be Used to Sensitize Cells to Transduction by AAVs Engineered to Interact with LY6A or LY6C1

AAV vectors are commonly used to deliver genes in vivo because of their ability to provide long-term expression. In addition, many AAV vectors are able to transverse vascular barriers after intravenous administration and deliver genes to the cells throughout numerous tissues, including but not limited to the brain, heart, liver, skeletal muscle, lungs, bone, cartilage, bone marrow, adrenal gland, retina, pancreas, adipose tissue and kidney. However, it remains challenging to develop AAV vectors that target specific cell types or specific organs in humans.

Previously, nanoparticle and other novel delivery modalities were developed and directed toward the vasculature of specific organs (Sago et al., Proc Natl Acad Sci USA. 2018 Oct. 16; 115(42):E9944-E9952; Sago et al., J Am Chem Soc. 2018 Dec. 12; 140(49): 17095-17105.; Järvinen et al., Int J Mol Sci. 2015 Sep. 30; 16(10):23556-71.). While such nanoparticles can be developed to preferentially deliver siRNAs and mRNAs to endothelial cells in specific organs, it remains challenging to use nanoparticles or other nonviral delivery vehicles to deliver DNA to the nucleus for long-term gene therapeutic applications or to achieve gene delivery across vasculature barriers to reach parenchymal cells within the target tissue(s).

In the present disclosure, a two-step delivery method that overcomes these challenges is described. The first step involves the expression, preferably transient, of an ectopic receptor for an engineered virus in the target cell population of a patient. The second step involves the administration of an AAV that specifically interacts with the ectopic receptor to the same patient during the window of receptor expression. This approach is attractive because it breaks down the process of achieving stable gene expression in the cells of specific organs into two steps. The first step requires only transient delivery or expression of a receptor in the target organ endothelium, which could be achieved by delivery of an mRNA carried by a nanoparticle, a RNA or DNA virus (e.g. a recombinant lentivirus, SV40, anellovirus, or adenovirus) or protein with a targeting motif or conjugate. It is not necessary nor preferred that the delivery system achieves persistent gene expression or traverses the vascular barrier. The second step uses an engineered AAV, such as those presented here within, to efficiently target the cells that ectopically express the receptor for the modified AAV. The ectopic receptor then mediates the transcytosis of the engineered AAV across the vasculature where it can subsequently transduce cells within the target organ and provide durable transgene expression from the recombinant viral genome.

In step one, the receptor, which is absent or expressed at a level that limits transduction in the target cell population, is ectopically expressed in, or delivered to, the target cell population of a patient. The delivery of the receptor can be achieved with a nanoparticle carrying an mRNA for the receptor or a viral vector carrying RNA or DNA encoding the receptor, or targeted to cells through the administration of the purified protein. Preferably, the receptor is not otherwise found or expressed in the human patient. Preferably, the delivery of the receptor protein or the nucleic acid encoding the receptor results in transient delivery of the receptor protein or expression of the receptor in the target population of interest.

In step two, the AAV vector that exhibits selectively enhanced binding to, and transduction of, cells expressing the receptor is administered during the window of ectopic receptor expression. Preferably, the AAV vector is delivered to a patient through the intravascular route. However, the receptor-selective AAV can be delivered through any route that provides access to the cells expressing the receptor. Ideally the expression of Ly6a or Ly6c would be transient and the delivery of the AAV vector that transduces cells though binding to LY6A or LY6C1 would be delivered during the window of time that LY6A or LY6C is present within the target cell population of interest.

Figure 10:
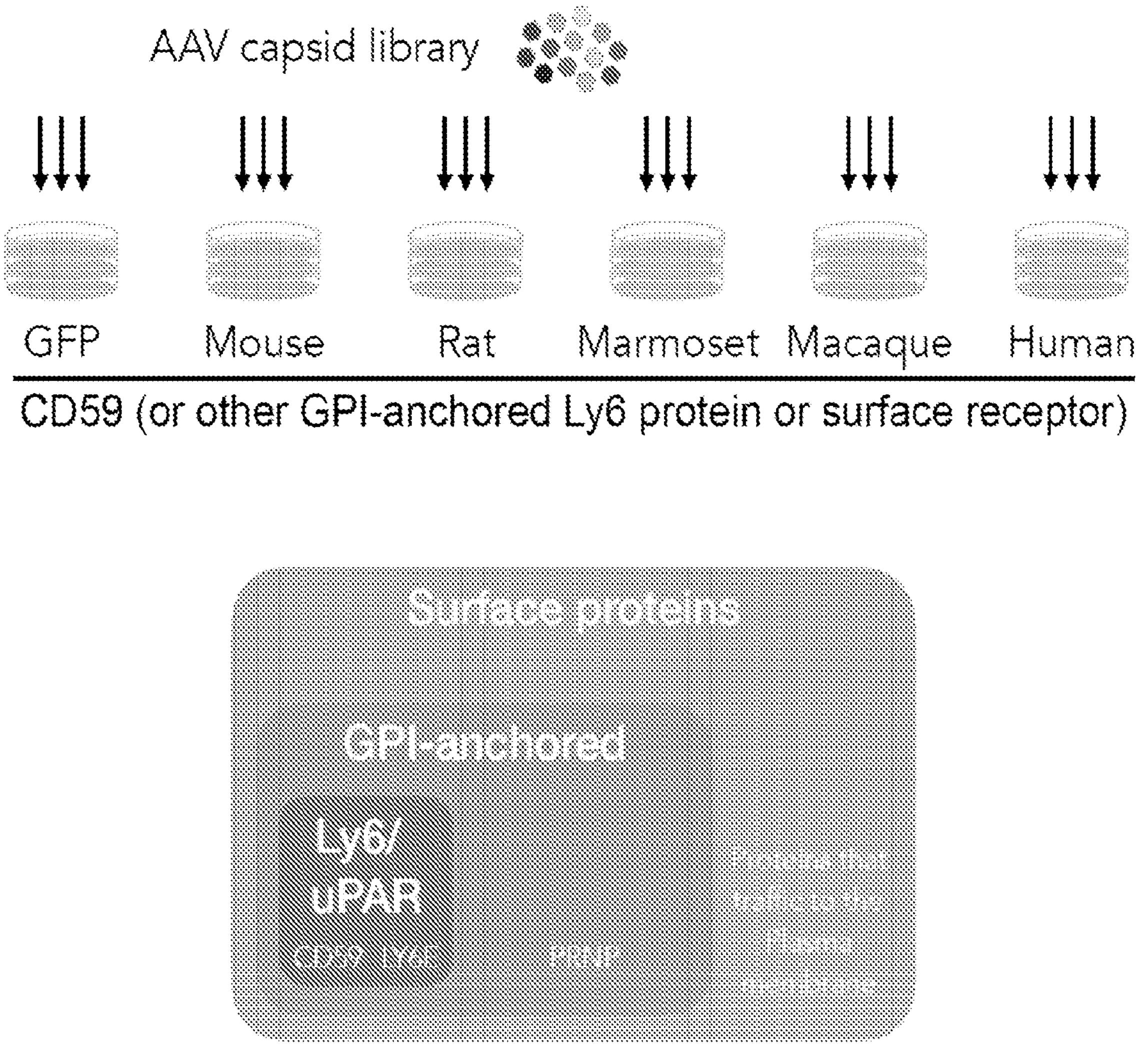
FIG. 10 shows a schematic depiction of a non-limiting example of a cell-based binding and transduction assay for high-throughput screening of capsid sequences that interact with specific target proteins.

Provided within are examples of receptor-modified AAV pairs that can be used for the above two-step delivery approach. Examples are provided of AAV capsids that have been screened for binding to and transduction of human cells that ectopically express mouse Ly6a (Tables 4, 9, 10) and Ly6c1 (Tables 5, 12, 13) or to purified LY6A-Fc or LY6C1-Fc proteins (Table 11 and 15, respectively). These receptors are attractive as ectopic AAV receptors for several reasons: (1) No homologs of these genes exist in humans or other primates. (2) These receptors are highly expressed on mouse CNS vasculature and have a demonstrated ability to efficiently transfer a subset of 7-mer modified AAVs across the vascular barrier (i.e., the BBB) and into the CNS where they can then transduce neurons and glia (Huang et al. 2019: FIG. 13). (3) These receptors can be ectopically expressed on human cells, and can be used as an assay to identify novel modified AAV capsids that selectively interact with these receptors (FIG. 10). It was found that many of these modified capsids mediate enhanced transduction of CNS vasculature and/or enhanced transduction of neural cells in the CNS after intravenous administration as demonstrated by their enrichment during in vivo Capsid mRNA-based screening assays (Table 10 and Table 14) and through the testing of the CNS tropism of individual variants (Table 6).

Example 12: Ectopic Ly6a or Ly6c1 Expression can be Used to Redirect the Tropism of Modified AAVs It was found that Ly6a expression in human HEK293T cells results in a >50-fold increase in binding by the AAV-PHP.B caspids (AAV-PHP.B, AAV-PHP.eB, AAV-PHP.B2 and AAV-PHP.B3) as compared to control cells not expressing Ly6a, but did not increase binding to the control AAV9 (Huang et al. (2019) BioRxiv, FIG. 3G). Importantly, it was also shown that ectopic expression of Ly6a in HEK293T cells enhanced the transduction by AAV-PHP.eB by 30-fold compared to cells lacking Ly6a.

To determine whether ectopic receptor expression can be used to render human endothelial cells more sensitive to transduction by viruses engineered to bind specific receptors, Ly6a, Ly6c1, or a control (mScarlet) was expressed in human hCMEC cells using a 7-mer modified AAV, AAV-BI-13, that efficiently transduces several human cultured cell types including hCMEC cells. The hCMEC cells expressing Ly6a, Ly6c1 or mScarlet were then exposed to AAV vectors that specifically interact with LY6A (represented by AAV-PHP.eB; Table 1-4) or LY6C1 (represented by AAV-BI-28; Tables 5-8). Expression of Ly6a or Ly6c1 made hCMEM cells approximately 2-logs (base 10) more sensitive to transduction by AAV-PHP.eB or AAV-BI-28, respectively. Importantly, the increased efficiency is highly specific—Ly6a expression selectively improved transduction by AAV-PHP.eB and Ly6c1 expression selectively improved transduction by AAV-BI-28. No increased transduction was observed for either vector in the cells expressing mScarlet.

Figure 11A:
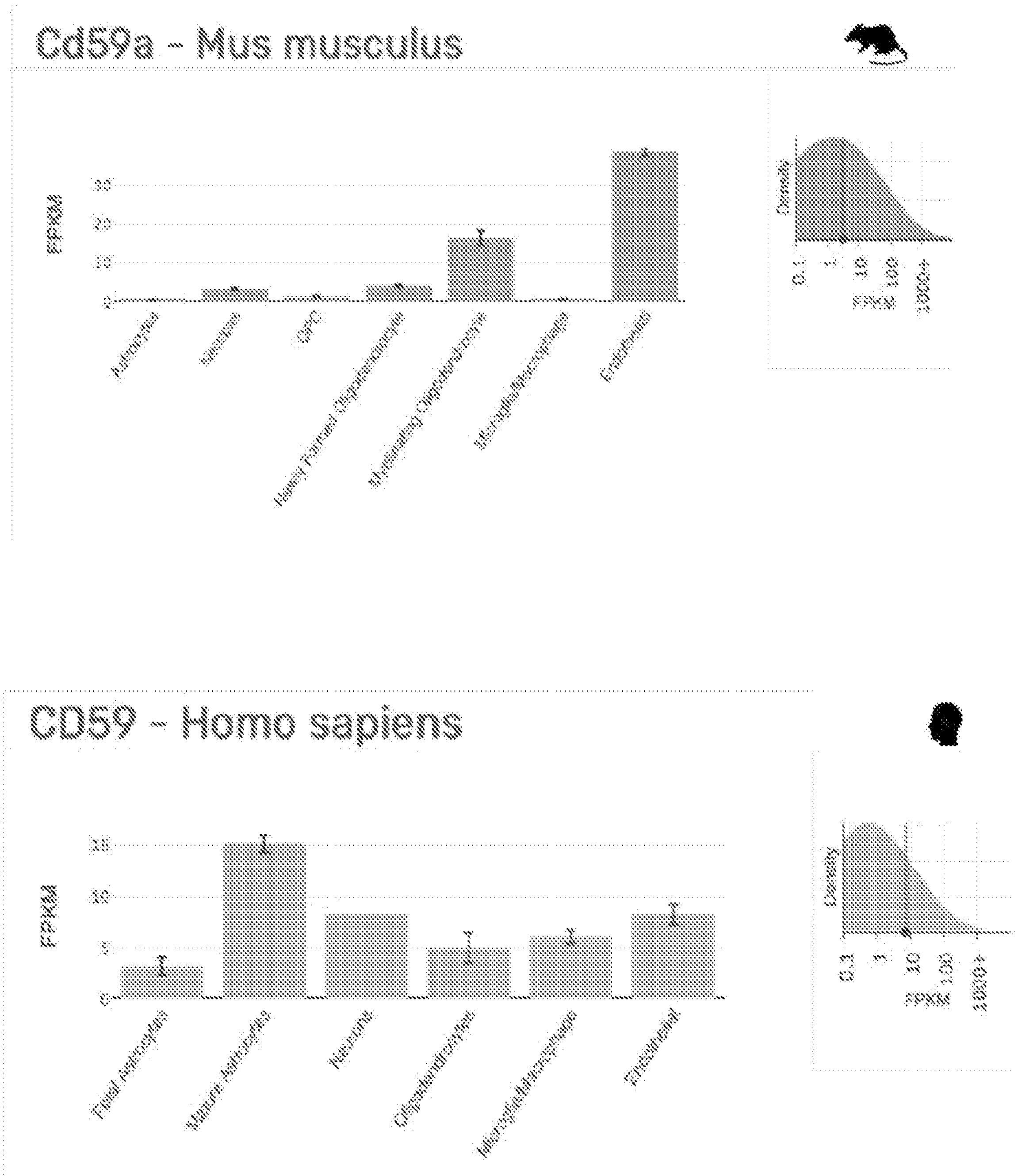
FIG. 11A shows data of CD59 expression from mouse (top) and human (below).
Figure 11B:
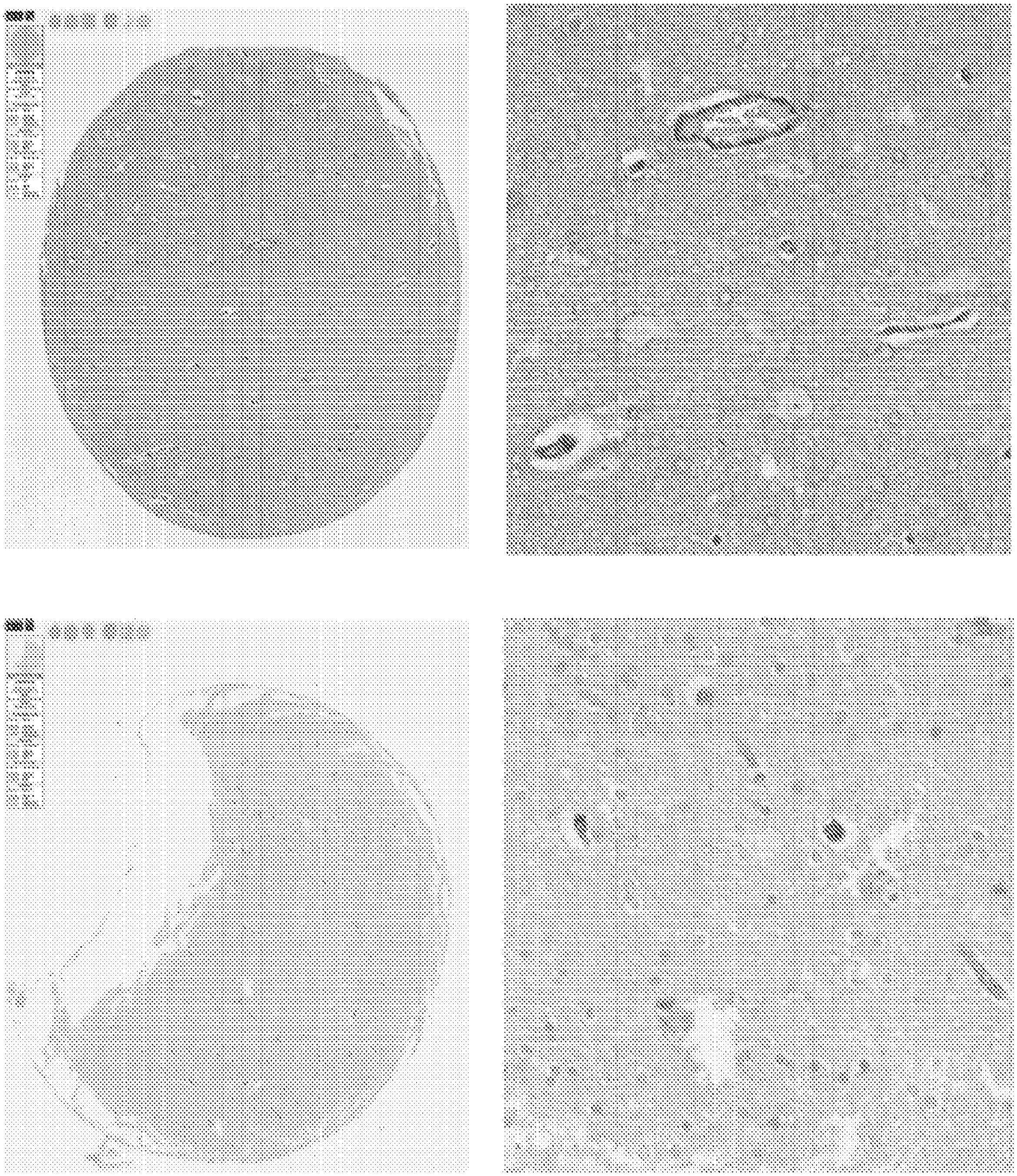
FIG. 11B shows data of CD59 expression on human brain vasculature.

Example 13: Identifying AAV Capsids that Target CD59, a LY6 Protein that is Conserved Between Mouse and Humans, and Expressed in CNS Endothelial Cells Using the in vitro binding assay, novel AAV capsids were identified that selectively bind cells overexpressing the human, marmoset, and/or mouse CD59 gene (FIG. 10 and Table 7) but not control cells expressing GFP. CD59 is a Ly6 family member that functions as a complement inhibitor and is expressed on brain vasculature. Brain RNA sequence data was obtained from Brain RNA-seq (www.BrainRNAseq.org) (FIG. 11A). CD59 tissue staining was obtained from Human Protein Atlas (www.proteinatlas.org) (FIG. 11B).

Example 14: The Use of AAV-PHP.B for Improved Efficiency of BBB Crossing Capabilities The development of AAV-PHP.B capsids provided proof-of-concept that AAV vectors with dramatically enhanced BBB crossing capabilities can be engineered, without a priori mechanistic knowledge [4,5]. AAV-PHP.B and AAV-PHP.eB are now widely used vectors for mouse neuroscience studies. However, the species-specific tropism of the AAV-PHP.B capsids reduces their appeal for human CNS gene therapy and highlights the shortcomings of performing selections and screens in model systems—the enhanced features of the identified capsids may not extend beyond the context (the genetic background) in which the selective pressure was applied. Accordingly, as compared to efforts in mice, selections in nonhuman primates (NHPs) are predicted to result in the identification of capsids whose enhanced features better translate to humans. Nonetheless, such efforts to develop clinically relevant vectors may likewise be thwarted by the identification of species- or model-specific capsids. Therefore, the pursuit of a vector that crosses the human BBB with AAV-PHP.eB-like efficiency gains will be aided by a mechanistic understanding of how naturally isolated and engineered capsids cross the BBB.

In the present disclosure, a single missense varian was rapidly identified tin Ly6a, out of a starting pool of millions of genetic variants, which segregates with efficient CNS transduction by AAV-PHP.eB. This was accomplished by first narrowing down candidates to genetic variants with a predicted high or medium impact and eliminating the bulk of the variants that did not segregate with the permissivity phenotype. This segregation study was achieved by leveraging Hail [26], the Mouse Genomes Project dataset [27], and 13 commercially available mouse lines; the code was implemented and run end-to-end on WGS data within hours, harnessing Hail's ability to scale computation across a large compute cluster, and the in vivo screening was completed in three weeks. The speed and small number of animals required for this approach is unprecedented compared to the conventional approaches of using diversity outbred lines or breeding generations of mice to determine the approximate genomic loci that segregates with a given phenotype.

After narrowing down the perfectly segregating genetic variants to two missense SNPs in two genes, molecular and biochemical studies were used to identify and validate Ly6a as the gene encoding the receptor for the AAV-PHP.B capsids. Because this approach was restricted to high and medium impact variants, the present disclosure does not rule out the possibility that other perfectly segregating noncoding variants present within Ly6a or other sites within the genome may contribute to the CNS transduction phenotype. In addition, it is possible that other genetic variants present in a subset of the nonpermissive strains within and surrounding Ly6a contribute to the nonpermissive phenotype. It is possible that one or more of these variants may influence Ly6a expression and contribute to the variation in LY6A levels and localization observed across nonpermissive strains.

The finding that Ly6a expression increases binding by the top three AAV-PHP.B variants, harboring unique peptide insertions (TLAVPFK, SVSKPFL, and FTLTTPK), identified using CREATE [5] suggests that LY6A has properties that make it an ideal receptor to engage for efficient transcytosis across the C57BL/6J BBB. Indeed, LY6A facilitates binding and transduction by AAV-PHP.eB in cells lacking either of the known AAV9 receptors, galactose and AAVR. Furthermore, ectopic expression of Ly6a is sufficient to render both human and hamster cells permissive to the enhanced binding and transduction of AAV-PHP.eB. Importantly, these findings demonstrate that AAVs can be engineered to utilize entirely new cell entry/transduction mechanisms rendering the novel capsids less dependent on interactions with the receptors that natural AAV serotypes rely on for transduction. Although there is no direct Ly6a homolog in primates, other cellular factors that share key properties with LY6A such as abundant luminal surface exposure on brain endothelium, localization within lipid micro-domains through GPI anchoring, or specific recycling/intracellular trafficking capabilities, may be prime molecular targets for gene delivery vectors in mice, NHPs, and humans. Notably, other LY6 proteins with homologs in primates are present within the CNS endothelium and can be explored and potentially harnessed for AAV capsid engineering. Developing capsids and/or other biologicals that target these receptors can open up new therapeutic avenues for treating a wide range of currently intractable neurological diseases.

```
Adeno-associated virus AAV9 capsid sequence
                                        (SEQ ID NO: 730)
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVIITSTR
```

-continued

```
IWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFIDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSKTINGSGQNQQTLKFSVAGPSNMAVQGRNYIPGPSYRQQRVS

TIVTQNNNSEFAWPGASSWALNGRNSLMNPGPAMASHKEGEDRFFPLSG

SLIFGKQGTGRDNVDADKVMITNEEEIKTTNPVATESYGQVATNHQSAQ

AQAQTGWVQNQGILPGMVWQDRDVYLQGPIWAKIPHTDGNFHPSPLMGG

FGMKHPPPQILIKNIPVPADPPTAFNKDKLNSFITQYSTGQVSVEIEWE

LQKENSKRWNPEIQYTSNYYKSNNVEFAVNTEGVYSEPRPIGTRYLTRN

L
```

Adeno-associated virus AAV9 capsid sequence AAV9 K449R (SEQ ID NO: 731)

```
MAADGYLPDWLEDNLSEGIREWWALKPGAPQPKANQQHQDNARGLVLPG

YKYLGPGNGLDKGEPVNAADAAALEHDKAYDQQLKAGDNPYLKYNHADA

EFQERLKEDTSFGGNLGRAVFQAKKRLLEPLGLVEEAAKTAPGKKRPVE

QSPQEPDSSAGIGKSGAQPAKKRLNFGQTGDTESVPDPQPIGEPPAAPS

GVGSLTMASGGGAPVADNNEGADGVGSSSGNWHCDSQWLGDRVITTSTR

TWALPTYNNHLYKQISNSTSGGSSNDNAYFGYSTPWGYFDFNRFHCHFS

PRDWQRLINNNWGFRPKRLNFKLFNIQVKEVTDNNGVKTIANNLTSTVQ

VFTDSDYQLPYVLGSAHEGCLPPFPADVFMIPQYGYLTLNDGSQAVGRS

SFYCLEYFPSQMLRTGNNFQFSYEFENVPFHSSYAHSQSLDRLMNPLID

QYLYYLSRTINGSGQNQQTLKFSVAGPSNMAVQGRNYIPGPSYRQQRVS

TIVIQNNNSEFAWPGASSWALNGRNSLMNPGPAMASHKEGEDRFFPLSG

SLIFGKQGTGRDNVDADKVMITNEEEIKTTNPVATESYGQVATNHQSAQ

AQAQTGWVQNQGILPGMVWQDRDVYLQGPIWAKIPHTDGNFHPSPLMGG

FGMKHPPPQILIKNTPVPADPPTAFNKDKLNSFITQYSTGQVSVEIEWE

LQKENSKRWNPEIQYTSNYYKSNNVEFAVNTEGVYSEPRPIGTRYLTRN

L
```

REFERENCES

1. J. R. Mendell et al., Single-Dose Gene-Replacement Therapy for Spinal Muscular Atrophy. *N. Engl. J. Med.* 377, 1713-1722 (2017).
2. B. Ravina et al., Intraputaminal AADC gene therapy for advanced Parkinson's disease: interim results of a phase 1b Trial [abstract]. *Human Gene Therapy.* 28, A6 (Dec. 1, 2017).
3. A. C. Nathwani, A. M. Davidoff, E. G. D. Tuddenham, Advances in Gene Therapy for Hemophilia. *Hum. Gene Ther.* 28, 1004-1012 (2017).
4. K. Y. Chan et al., Engineered AAVs for efficient noninvasive gene delivery to the central and peripheral nervous systems. *Nat. Neurosci.* 20, 1172-1179 (2017).
5. B. E. Deverman et al., Cre-dependent selection yields AAV variants for widespread gene transfer to the adult brain. *Nat. Biotechnol.* 34, 204-209 (2016).
6. O. J. Müller et al., Random peptide libraries displayed on adeno-associated virus to select for targeted gene therapy vectors. *Nat. Biotechnol.* 21, 1040-1046 (2003).
7. D. S. Ojala et al., In Vivo Selection of a Computationally Designed SCHEMA AAV Library Yields a Novel Variant for Infection of Adult Neural Stem Cells in the SVZ. *Mol. Ther.* 26, 304-319 (2018).
8. D. G. R. Tervo et al., A Designer AAV Variant Permits Efficient Retrograde Access to Projection Neurons. *Neuron.* 92, 372-382 (2016).
9. M. A Kotterman, D. V. Schaffer, Engineered AAV vectors for improved central nervous system gene delivery. *Neurogenesis.* 2, e1122700 (2015).
10. K. J. D. A. Excoffon et al., Directed evolution of adeno-associated virus to an infectious respiratory virus. *Proc. Natl. Acad. Sci. U.S.A* 106, 3865-3870 (2009).
11. D. Dalkara et al., In vivo-directed evolution of a new adeno-associated virus for therapeutic outer retinal gene delivery from the vitreous. *Sci. Transl. Med.* 5, 189ra76 (2013).
12. L. Lisowski et al., Selection and evaluation of clinically relevant AAV variants in a xenograft liver model. *Nature.* 506, 382-386 (2014).
13. J. Körbelin et al., A brain microvasculature endothelial cell-specific viral vector with the potential to treat neurovascular and neurological diseases. *EMBO Mol. Med.* 8, 609-625 (2016).
14. M. Zelikowsky et al., The Neuropeptide Tac2 Controls a Distributed Brain State Induced by Chronic Social Isolation Stress. *Cell.* 173, 1265-1279.e19 (2018).
15. D. Hillier et al., Causal evidence for retina-dependent and -independent visual motion computations in mouse cortex. *Nat. Neurosci.* 20, 960-968 (2017).
16. A. L. Gibson et al., Adeno-Associated Viral Gene Therapy Using PHP.B:NPC1 Ameliorates Disease Phenotype in Mouse Model of Niemann-Pick C1 Disease (conference paper). American Society of Gene and Cell Therapy Annual Meeting. Washington, DC, USA. (May 10-13, 2017).
17. Y. Gao, L. Geng, V. P. Chen, S. Brimijoin, Therapeutic Delivery of Butyrylcholinesterase by Brain-Wide Viral Gene Transfer to Mice. *Molecules.* 22 (2017), doi: 10.3390/molecules22071145.
18. G. Morabito et al., AAV-PHP.B-Mediated Global-Scale Expression in the Mouse Nervous System Enables GBA1 Gene Therapy for Wide Protection from Synucleinopathy. *Mol. Ther.* 25, 2727-2742 (2017).
19. R. D. Dayton, M. S. Grames, R. L. Klein, More expansive gene transfer to the rat CNS: AAV PHP.EB vector dose-response and comparison to AAV PHP.B. *Gene Ther.* 25, 392-400 (2018).
20. K. L. Jackson, R. D. Dayton, B. E. Deverman, R. L. Klein, Better Targeting, Better Efficiency for Wide-Scale Neuronal Transduction with the Synapsin Promoter and AAV-PHP.B. *Front. Mol. Neurosci.* 9, 116 (2016).
21. J. Hordeaux et al., The Neurotropic Properties of AAV-PHP.B Are Limited to C57BL/6J Mice. *Mol. Ther.* 26, 664-668 (2018).
22. Y. Matsuzaki et al., Intravenous administration of the adeno-associated virus-PHP.B capsid fails to upregulate transduction efficiency in the marmoset brain. *Neurosci. Lett.* 665, 182-188 (2018).
23. Sah, D., Safety and Increased Transduction Efficiency in the Adult Nonhuman Primate Central Nervous System with Intravenous Delivery of Two Novel Adeno-Associated Virus Capsids [abstract O661]. American Society of Gene and Cell Therapy Annual Meeting. Chicago, IL, USA. *Molecular Therapy*. (May 16-19, 2018).
24. C. N. Bedbrook, B. E. Deverman, V. Gradinaru, Viral Strategies for Targeting the Central and Peripheral Nervous Systems. *Annu. Rev. Neurosci.* 41, 323-348 (2018).
25. W. E. Allen et al., Global Representations of Goal-Directed Behavior in Distinct Cell Types of Mouse Neocortex. *Neuron.* 94, 891-907.e6 (2017).
26. Hail, (available at github.com/hail-is/hail).
27. T. M. Keane et al., Mouse genomic variation and its effect on phenotypes and gene regulation. *Nature.* 477, 289-294 (2011).
28. B. Yalcin et al., Sequence-based characterization of structural variation in the mouse genome. *Nature.* 477, 326-329 (2011).
29. Y. Zhang et al., An RNA-sequencing transcriptome and splicing database of glia, neurons, and vascular cells of the cerebral cortex. *J. Neurosci.* 34, 11929-11947 (2014).
30. K. R. Spindler et al., The major locus for mouse adenovirus susceptibility maps to genes of the hematopoietic cell surface-expressed LY6 family *J. Immunol.* 184, 3055-3062 (2010).
31. J. D. Guida, G. Fejer, L. A. Pirofski, C. F. Brosnan, M. S. Horwitz, Mouse adenovirus type 1 causes a fatal hemorrhagic encephalomyelitis in adult C57BL/6 but not BALB/c mice. *J. Virol.* 69, 7674-7681(1995).
32. C. Loeuillet et al., In vitro whole-genome analysis identifies a susceptibility locus for HIV-1. *PLoS Biol.* 6, e32 (2008).
33. A. L. Brass et al., Identification of host proteins required for HIV infection through a functional genomic screen. *Science.* 319, 921-926 (2008).
34. M. N. Krishnan et al., RNA interference screen for human genes associated with West Nile virus infection. *Nature.* 455, 242-245 (2008).
35. K. B. Mar et al., LY6E mediates an evolutionarily conserved enhancement of virus infection by targeting a late entry step. *Nat. Commun.* 9, 3603 (2018).
36. H.-C. Liu, M. Niikura, J. E. Fulton, H. H. Cheng, Identification of chicken lymphocyte antigen 6 complex, locus E (LY6E, alias SCA2) as a putative Marek's disease resistance gene via a virus-host protein interaction screen. *Cytogenet. Genome Res.* 102, 304-308 (2003).
37. C. Cray, R. W. Keane, T. R. Malek, R. B. Levy, Regulation and selective expression of Ly-6A/E, a lymphocyte activation molecule, in the central nervous system. *Molecular Brain Research.* 8, 9-15 (1990).
38. M. van de Rijn, S. Heimfeld, G. J. Spangrude, I. L. Weissman, Mouse hematopoietic stem-cell antigen Sca-1 is a member of the Ly-6 antigen family. *Proc. Natl. Acad. Sci. U.S.A.* 86, 4634-4638 (1989).
39. F. A. Ran et al. In vivo genome editing using *Staphylococcus aureus* Cas9. *Nature.* 520, 186-191 (2015).
40. C. Summerford, J. S. Johnson, R. J. Samulski, AAVR: A Multi-Serotype Receptor for AAV. *Mol. Ther.* 24, 663-666 (2016).
41. M. Kikkert et al., Binding of Tomato Spotted Wilt Virus to a 94-kDa Thrips Protein. *Phytopathology.* 88, 63-69 (1998).
42. S. Pillay et al., AAV serotypes have distinctive interactions with domains of the cellular receptor AAVR. *J. Virol.* (2017), doi:10.1128/JVI.00391-17.
43. A. Pierleoni, P. L. Martelli, R. Casadio, PredGPI: a GPI-anchor predictor. *BMC Bioinformatics.* 9, 392 (2008).
44. L.-Y. Huang, S. Halder, M. Agbandje-McKenna, Parvovirus glycan interactions. *Curr. Opin.* Virol. 7, 108-118 (2014).
45. S. Shen, K. D. Bryant, S. M. Brown, S. H. Randell, A. Asokan, Terminal N-Linked Galactose Is the Primary Receptor for Adeno-associated Virus 9. *J. Biol. Chem.* 286, 13532-13540 (2011).
46. C. L. Bell, B. L. Gurda, K. Van Vliet, M. Agbandje-McKenna, J. M. Wilson, Identification of the galactose binding domain of the adeno-associated virus serotype 9 capsid. *J. Virol.* 86, 7326-7333 (2012).
47. S. Pillay et al., An essential receptor for adeno-associated virus infection. *Nature.* 530, 108-112 (2016).
48. S. L. Deutscher, C. B. Hirschberg, Mechanism of galactosylation in the Golgi apparatus. A Chinese hamster ovary cell mutant deficient in translocation of UDP-galactose across Golgi vesicle membranes. *J. Biol. Chem.* 261, 96-100 (1986).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

Lengthy table referenced here

US12773462-20261027-T00001

Please refer to the end of the specification for access instructions.

Lengthy table referenced here

US12773462-20261027-T00002

Please refer to the end of the specification for access instructions.

Lengthy table referenced here

US12773462-20261027-T00003

Please refer to the end of the specification for access instructions.

Lengthy table referenced here

US12773462-20261027-T00004

Please refer to the end of the specification for access instructions.

Lengthy table referenced here

US12773462-20261027-T00005

Please refer to the end of the specification for access instructions.

Lengthy table referenced here

US12773462-20261027-T00006

Please refer to the end of the specification for access instructions.

Lengthy table referenced here

US12773462-20261027-T00007

Please refer to the end of the specification for access instructions.

Lengthy table referenced here

US12773462-20261027-T00008

Please refer to the end of the specification for access instructions.

Lengthy table referenced here

US12773462-20261027-T00009

Please refer to the end of the specification for access instructions.

Lengthy table referenced here

US12773462-20261027-T00010

Please refer to the end of the specification for access instructions.

Lengthy table referenced here

US12773462-20261027-T00011

Please refer to the end of the specification for access instructions.

Lengthy table referenced here

US12773462-20261027-T00012

Please refer to the end of the specification for access instructions.

Lengthy table referenced here

US12773462-20261027-T00013

Please refer to the end of the specification for access instructions.

LENGTHY TABLES

The patent contains a lengthy table section. A copy of the table is available in electronic form from the USPTO web site (https://seqdata.uspto.gov/docdetail?docId=US12773462B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/docdetail?docId=US12773462B2). An electronic copy of the sequence listing will also be available from the USPTO upon request and payment of the fee set forth in 37 CFR 1.19(b)(3).

The invention claimed is:

1. A method comprising:

providing an adeno-associated virus (AAV) capsid protein;

contacting the AAV capsid protein with a cell that expresses a protein of the lymphocyte antigen-6 (Ly6)/urokinase-type plasminogen activator receptor (uPAR) protein family attached to the surface of the cell; and selecting the AAV capsid protein if it specifically binds to the protein of the Ly6/uPAR protein family attached to the surface of the cell; wherein the protein of the Ly6/uPAR protein family is expressed recombinantly in the cell, and wherein the protein of the Ly6/uPAR protein family is CD59A.

2. The method of claim 1, wherein the AAV capsid protein is an AAV9 capsid protein.

3. The method of claim 2, wherein the AAV9 capsid protein contains an insertion between amino acids 586-592 of SEQ ID NO: 730.

4. The method of claim 1, wherein the protein of the Ly6/uPAR protein family is expressed in the central nervous system.

5. The method of claim 1, wherein the method comprises contacting the AAV capsid protein with a cell that expresses a GPI-anchored protein.

6. The method of claim 1, wherein the AAV capsid protein comprises at least 4 contiguous amino acids of SEQ ID NO: 316.

7. The method of claim 3, wherein the AAV9 capsid protein contains an insertion between amino acids 588-589 of SEQ ID NO: 730.

8. The method of claim 1, wherein the AAV capsid protein is part of an AAV1, AAV2, AAV3, AAV4, AAV5, AAV6, AAV7, AAV8, AAV10 or AAV11.

9. The method of claim 1, wherein the protein of the Ly6/uPAR protein family forms a dimer.

10. The method of claim 1, wherein the method is conducted in vitro.

11. The method of claim 1, wherein the AAV capsid protein comprises SEQ ID NO: 316.

* * * * *